United States Patent
Kim et al.

(10) Patent No.: US 9,682,622 B2
(45) Date of Patent: Jun. 20, 2017

(54) DRIVER MONITORING SYSTEM

(71) Applicant: LG ELECTRONICS INC., Seoul (KR)

(72) Inventors: Sunghyun Kim, Seoul (KR); Sungwook Hong, Seoul (KR); Joomin Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 14/672,520

(22) Filed: Mar. 30, 2015

(65) Prior Publication Data

US 2015/0328985 A1 Nov. 19, 2015

(30) Foreign Application Priority Data

May 15, 2014 (KR) .................. 10-2014-0058583

(51) Int. Cl.
*A61B 5/18* (2006.01)
*B60K 28/06* (2006.01)
(Continued)

(52) U.S. Cl.
CPC .............. *B60K 28/066* (2013.01); *A61B 5/18* (2013.01); *A61B 5/746* (2013.01); *B60W 40/08* (2013.01); *B60W 50/14* (2013.01); *B60W 50/16* (2013.01); *G08B 21/06* (2013.01); *H04N 5/23229* (2013.01); *A61B 5/0261* (2013.01); *A61B 5/0402* (2013.01); *A61B 5/0488* (2013.01); *A61B 5/0496* (2013.01); *A61B 5/0533* (2013.01); *A61B 5/681* (2013.01); *A61B 5/6803* (2013.01); *B60W 2040/0827* (2013.01); *B60W 2050/0089* (2013.01);
(Continued)

(58) Field of Classification Search
CPC .......... A61B 5/18; A61B 5/746; G08B 21/06; B60W 40/08; B60W 50/14; B60W 2040/0827
See application file for complete search history.

(56) References Cited

U.S. PATENT DOCUMENTS 6,265,978 B1 7/2001 Atlas
7,821,409 B2 10/2010 Ishida
(Continued)

FOREIGN PATENT DOCUMENTS

DE 10210130 9/2003
DE 102005048542 4/2007
(Continued)

OTHER PUBLICATIONS

Korean Office Action dated Jul. 9, 2015 for Korean Application No. 10-2014-0058583, 6 Pages.
(Continued)

*Primary Examiner* — Faye M Fleming
(74) *Attorney, Agent, or Firm* — Fish & Richardson P.C.

(57) ABSTRACT

A driver state monitoring (DSM) system includes an image obtainment apparatus configured to obtain image information of a user driving a vehicle; a biological information obtainment unit configured to be worn on a specific portion of the user's body and to obtain biological information from the specific portion of the user's body; and a controller configured to detect a dangerous driving-state in which the user drives the vehicle, based on the image information and the biological information of the user.

16 Claims, 20 Drawing Sheets

(51) Int. Cl.
*H04N 5/232* (2006.01)
*B60W 50/14* (2012.01)
*B60W 50/16* (2012.01)
*B60W 40/08* (2012.01)
*G08B 21/06* (2006.01)
*A61B 5/00* (2006.01)
*B60W 50/00* (2006.01)
*A61B 5/026* (2006.01)
*A61B 5/0402* (2006.01)
*A61B 5/0488* (2006.01)
*A61B 5/0496* (2006.01)
*A61B 5/053* (2006.01)

(52) U.S. Cl.
CPC . *B60W 2050/143* (2013.01); *B60W 2050/146* (2013.01); *B60W 2420/42* (2013.01); *B60W 2540/22* (2013.01); *B60W 2540/28* (2013.01)

(56) References Cited

U.S. PATENT DOCUMENTS

| | | | |
|---|---|---|---|
| 8,786,448 B2 | 7/2014 | Oguri | |
| 2004/0233060 A1* | 11/2004 | Mohri | A61B 5/1103 340/575 |
| 2005/0052348 A1* | 3/2005 | Yamazaki | G02B 27/01 345/44 |
| 2005/0195079 A1* | 9/2005 | Cohen | G08B 25/10 340/539.12 |
| 2006/0250256 A1* | 11/2006 | Power | G08B 21/06 340/575 |
| 2008/0238694 A1 | 10/2008 | Ishida | |
| 2010/0090839 A1 | 4/2010 | Omi | |
| 2011/0295086 A1 | 12/2011 | Nakada et al. | |
| 2012/0105234 A1 | 5/2012 | Oguri | |
| 2014/0368336 A1* | 12/2014 | Felix | H04W 4/008 340/539.13 |
| 2015/0002808 A1* | 1/2015 | Rizzo, III | A61F 9/08 351/158 |
| 2015/0327803 A1* | 11/2015 | Fujita | A61B 5/11 340/576 |
| 2015/0351681 A1* | 12/2015 | Lee | A61B 5/4806 600/595 |
| 2016/0039424 A1* | 2/2016 | Hong | B60W 40/08 701/2 |
| 2016/0131905 A1* | 5/2016 | Takahashi | G02B 27/017 345/8 |

FOREIGN PATENT DOCUMENTS

| | | |
|---|---|---|
| DE | 102012201802 | 8/2013 |
| DE | 102012020901 | 4/2014 |
| EP | 2 453 427 A1 | 5/2012 |
| EP | 2821978 | 1/2015 |
| JP | 2002-183900 A | 6/2002 |
| JP | 2008-242602 A | 10/2008 |
| JP | 2009-018765 A | 1/2009 |
| JP | 2011-183005 A | 9/2011 |
| KR | 10-2012-0046230 A | 5/2012 |
| WO | 2013/128920 | 9/2013 |

OTHER PUBLICATIONS

Natasha J., "Introducing a Breakthrough Scout Feature Road Rage Detection BETA", http://blog.scout.me/introducing-a-breakthrough-scout-feature-road-rage-detection-beta/; Apr. 1, 2013, 3 pages.
Extended European Search Report issued in European Application No. 15001394.4 on Jan. 20, 2016, 13 pages.
Partial European Search Report issued in European Application No. 15001394.4 on Oct. 20, 2015, 8 pages.

* cited by examiner

DRIVER MONITORING SYSTEM

CROSS-REFERENCE TO RELATED APPLICATION

Pursuant to 35 U.S.C. §119(a), this application claims the benefit of an earlier filing date and right of priority to Korean Application No. 10-2014-0058583, filed on May 15, 2014, the contents of which are incorporated by reference herein in their entirety.

TECHNICAL FIELD

This application relates to a driver monitoring system and particularly, to a mobile terminal and a vehicle control apparatus that determine whether a driver of a vehicle is driving in a dangerous driving state.

BACKGROUND

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs. Efforts are ongoing to support and increase the functionality of mobile terminals. Such efforts include software and hardware improvements, as well as changes and improvements in the structural components.

SUMMARY

In one aspect, a driver state monitoring (DSM) system includes an image obtainment apparatus configured to obtain image information of a user driving a vehicle; a biological information obtainment unit configured to be worn on a specific portion of the user's body and to obtain biological information from the specific portion of the user's body; and a controller configured to detect a dangerous driving-state in which the user drives the vehicle, based on the image information and the biological information of the user.

In some implementations, the controller is configured to, based on the image information and the biological information, determine whether the dangerous driving-state corresponds to a drowsy driving state, a distracted driving-state, or a stressful driving-state.

In some implementations, the controller is configured to, based on the image information and the biological information, generate information on a danger level indicating an extent of danger corresponding to the determined dangerous driving-state.

In some implementations, the controller is configured to generate the information on the determined danger level by applying a weighting factor to at least one of the image information or the biological information.

In some implementations, the applied weighting factor differs depending on whether the dangerous driving-state corresponds to the drowsy driving state, the distracted driving-state, or the stressful driving-state.

In some implementations, the controller is configured to output the generated information on the determined danger level through an output unit.

In some implementations, the controller is configured to adjust an output strength of the information on the danger level as the information on the danger level changes, and wherein the information on the danger level is output according to the adjusted output strength.

In some implementations, the output unit is provided in a mobile terminal and is configured to output the information on the danger level in the form of a vibration output or an audio output.

In some implementations, the controller is configured to adjust the output strength by changing at least one of a frequency of the vibration output, an amplitude of the vibration output, an output period of the vibration output, an amplitude of the audio output, contents of the audio output, or an output period of the audio output.

In some implementations, the output unit is provided in the vehicle, and a vehicle control apparatus provided in the vehicle is configured to control the output unit to output the information on the danger level in the form of an image output or an audio output. Furthermore, the output unit is at least one of an emergency light, a light emitting diode (LED) installed in a dashboard of the vehicle, a vibration-enabled seat of the vehicle, or a vibration-enabled wheel steering apparatus of the vehicle.

In some implementations, the controller is configured to adjust the output strength by changing at least one of an output period of the emergency light, a light color of the LED, an output period of the LED, a vibration frequency of the vibration-enabled seat or of the vibration-enabled wheel steering apparatus, an amplitude of the vibration, or an output period of the vibration.

In some implementations, the biological information includes at least one of sleep-state information or biorhythm information of the user that is measured before the user drives the vehicle.

In some implementations, the dangerous driving-state corresponds to a drowsy driving-state, and the controller is configured to generate a drowsiness trend line over time for the user, based on at least one of the sleep-state information or the biorhythm information, and to detect the dangerous driving-state, based on the generated drowsiness trend line and the image information.

In some implementations, the controller is configured to generate a driving-state learning model for determining the user's dangerous driving-state based on past image information and past biological information of the user, and to detect the dangerous driving-state based on the image information, the biological information, and the generated driving-state learning model.

In some implementations, the system further includes a mobile terminal configured to be worn on the specific portion of the user's body. The mobile terminal includes the biological information obtainment unit, and a communication unit that receives the image information from an image obtainment apparatus provided in the vehicle.

In some implementations, the mobile terminal further includes the controller.

In another aspect, a vehicle control apparatus is configured to be installed in a vehicle. The vehicle control apparatus includes a communication unit configured to perform communication with a mobile terminal that is configured to be wearable on a specific portion of a user's body. The vehicle control apparatus also includes an image obtainment unit configured to obtain image information of a user. The vehicle control apparatus also includes a controller. The controller is configured to control the communication unit to receive, from the mobile terminal, biological information of the user that is obtained from a specific portion of the user's body on which the mobile terminal is worn, and is also configured to detect a dangerous driving-state in which the user drives, based on the image information and the biological information of the user.

In some implementations, the controller is configured to, based on the image information and the biological information, determine whether the dangerous driving-state corresponds to a drowsy driving state, a distracted driving-state, or a stressful driving-state; and wherein based on the image information and the biological information, the controller is configured to generate information on a danger level indicating an extent of danger corresponding to the dangerous driving-state.

In some implementations, the controller is configured to generate the information on the danger level by applying a weighting factor to at least one of the image information or the biological information.

In some implementations, the applied weighting factor differs depending on whether the dangerous driving-state corresponds to the drowsy driving state, the distracted driving-state, or the stressful driving-state.

In some implementations, the controller is configured to output the generated information on the determined danger level through an output unit.

In some implementations, the controller is configured to adjust an output strength of the information on the danger level as the information on the danger level changes, and wherein the information on the danger level is output according to the adjusted output strength.

In some implementations, an output unit is provided in the mobile terminal and is configured to output the information on the danger level in the form of an image output or an audio output, and an output unit is provided in the vehicle and includes at least one of an emergency light of the vehicle, a light emitting diode (LED) installed in a dashboard of the vehicle, a vibration-enabled seat of the vehicle, or a vibration-enabled wheel steering apparatus of the vehicle.

In some implementations, the controller is configured to adjust the output strength by changing at least one of an output period of the emergency light, a light color of the LED, an output period of the LED, a vibration frequency of the vibration-enabled seat or of the vibration-enabled wheel steering apparatus, an amplitude of the vibration, or an output period of the vibration.

In some implementations, the mobile terminal is configured to output the information on the danger level in the form of a vibration output or an audio output, and is configured to adjust the output strength by changing at least one of a frequency of the vibration output, an amplitude of the vibration output, a period of the vibration output, an amplitude of the audio output, contents of the audio output, or a period of the audio output.

In some implementations, the biological information includes at least one of sleep-state information or biorhythm information of the user that is measured before the user drives the vehicle.

In some implementations, the dangerous driving-state corresponds to a drowsy driving-state, and the controller is configured to create a drowsiness trend line over time for the user, based on at least one of the sleep-state information or the biorhythm information, and to detect the dangerous driving-state, based on the generated drowsiness trend line and the image information.

In some implementations, the controller is configured to generate a driving-state learning model for determining the user's dangerous driving-state based on past image information and past biological information of the user, and to detect the dangerous driving-state based on the image information, the biological information, and the driving-state learning model.

All or part of the features described throughout this application can be implemented as a computer program product including instructions that are stored on one or more non-transitory machine-readable storage media, and that are executable on one or more processing devices. All or part of the features described throughout this application can be implemented as an apparatus, method, or electronic system that can include one or more processing devices and memory to store executable instructions to implement the stated functions.

The details of one or more implementations are set forth in the accompanying drawings and the description below. Other features will be apparent from the description and drawings, and from the claims. The description and specific examples below are given by way of illustration only, and various changes and modifications will be apparent.

DETAILED DESCRIPTION

Figure 1:
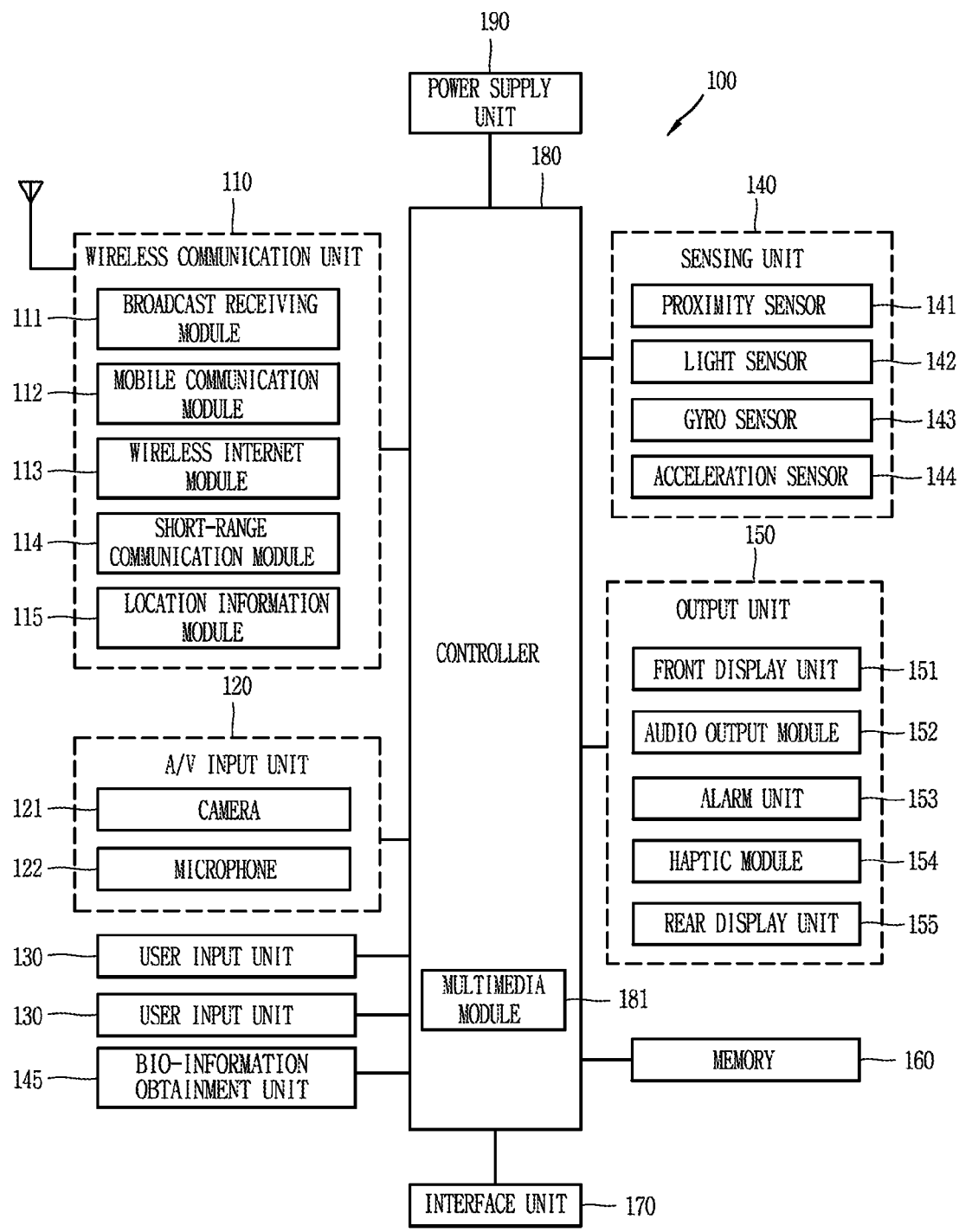
FIG. 1 is a block diagram illustrating an example of a mobile terminal.

A system obtains biological information and/or image information of a user who is driving a vehicle, determines whether the user is driving in a dangerous driving-state. The system may also provide feedback to the user regarding a detected dangerous driving-state. In some implementations, a mobile terminal (e.g., a smart watch and/or digital eye glasses) is worn by the user and collects biological information about the user. An image obtainment unit (e.g., a camera) may be provided to capture image information of the user. A controller, which may be provided either on the mobile terminal or in the vehicle, uses the biological information and/or the image information to determine whether the user is driving the vehicle in a dangerous driving state. Examples of dangerous driving states include a drowsy driving state, a distracted driving-state, and a stressful driving-state.

In some implementations, the system may obtain historical data collected about the user prior to the user driving the vehicle, and use the historical data in addition (or as an alternative) to the biological information and image information to determine a dangerous driving state of the user. For example, the system may utilize data regarding sleeping pattern to determine an initial value of a drowsy driving state, when the user first enters the vehicle. The system may also use historical information regarding a user to create a baseline from which to compare measured sensor values while the user is driving the vehicle.

The system may thus use various types of sensor information to automatically detect and alert a driver (or alert another person) regarding a dangerous driving state of the driver. In some implementations, a sensor may be provided in a mobile terminal (e.g., a smart watch or wearable smart glasses) that is worn by a user, and the mobile terminal may continuously or periodically collect information regarding the user.

Various types of mobile terminals may be utilized with user convenience in mind. Among them, wearable devices may include various types of electronic devices that are wearable on a user's body or user's clothes. Such wearable devices may include, for example, a smart watch, a wearable computer, digital eye glasses, a Bluetooth headset, and other smart wear.

To perform various functions, the wearable devices may be realized as multimedia devices. For example, the smart watch function may function as a watch, and may also capture a static image or record a moving image with a camera built into it and reproduce multimedia content with a display unit formed in the main body of the watch. In addition, the smart watch may receive incoming messages over a wireless network and connect to a social network with various plug-ins that enable communication (e.g., via e-mail).

Various functions may be possible with a mobile terminal or a wearable device (hereinafter collectively referred to as a "mobile terminal," although this is not intended to limit a device to which the technology disclosed in the present specification is applied) in order to provide a user with more convenience.

In particular, implementations described herein provide a technology that makes it possible to determine whether a driver drives a vehicle in a dangerous state (including a drowsy state, a distracted state, a stressful state and like) using various pieces of biological information on the driver of the vehicle that is obtained by the mobile terminal when the driver carrying the mobile terminal rides in the vehicle.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices, and the like. By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

A vehicle control apparatus according to some implementations is applied to various pieces of equipment and apparatuses, such as a telematics terminal, a navigation terminal, audio video navigation (AVN) terminal, a television set, a 3D television set, an audio/video (A/V) system, an information providing center, and a call center.

In addition, the vehicle control apparatus according to some implementations is configured to be also in the form of a mobile terminal that is connected to the vehicle in a wired or wireless manner. In this case, like the mobile terminal described above, the vehicle control apparatuses may include a mobile phone, a smart phone, a laptop computer, a digital-broadcast-dedicated terminal, a personal digital assistant (PDA), a portable multimedia player (PMP), a navigation system, a slate PC, a tablet PC, a subnotebook computer, or a wearable device and the like.

A singular representation may include a plural representation as far as it represents a definitely different meaning from the context. Terms 'include' or 'has' used herein should be understood that they are intended to indicate an existence of several components or several steps, disclosed in the specification, and it may also be understood that part of the components or steps may not be included or additional components or steps may further be included.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element.

Some examples of implementations will be described below in detail with reference to the accompanying drawings where those components are rendered the same reference number that are the same or are in correspondence, regardless of the figure number, and redundant explanations are omitted.

Mobile Terminal

Hereinafter, a mobile terminal according to some implementations will be explained in more detail with reference to FIGS. 1 to 5B.

FIG. 1 is a block diagram of an example of a mobile terminal according to some implementations.

As shown in FIG. 1, the mobile terminal 100 includes a radio communication unit 110, an A/V (Audio/Video) input unit 120, a user input unit 130, a sensing unit 140, a biological information obtainment unit 145, an output unit 150, a memory 160, an interface unit 170, a controller 180, and a power supply unit 190. FIG. 1 shows the mobile terminal 100 having various components, but it is understood that implementing all of the illustrated components is not a requirement. The mobile terminal 100 may be implemented by greater or fewer components.

Hereinafter, each of the above components will be explained.

The radio communication unit 110 typically includes one or more components to provide radio communication between the mobile terminal 100 and a radio communication unit system or a network in which the mobile terminal 100 is located. For example, the radio communication unit 110 may include a broadcast receiving module 111, a mobile communication module 112, a wireless Internet module 113, a short range communication module 114, a location information module 115, etc.

The broadcast receiving module 111 receives broadcast signals and/or broadcast associated information from an external broadcast management server (or other network entity) via a broadcast channel.

The broadcast channel may include a satellite channel and/or a terrestrial channel. The broadcast management server may be a server that generates and transmits a broadcast signal and/or broadcast associated information or a server that receives a previously generated broadcast signal and/or broadcast associated information and transmits the same to a terminal. The broadcast signal may include a TV broadcast signal, a radio broadcast signal, a data broadcast signal, and the like. Also, the broadcast signal may further include a broadcast signal combined with a TV or radio broadcast signal.

The broadcast associated information may refer to information associated with a broadcast channel, a broadcast program or a broadcast service provider. The broadcast associated information may also be provided via a mobile communication network. In this case, the broadcast associated information may be received by the mobile communication module 112.

The broadcast associated information may exist in various forms. For example, it may exist in the form of an electronic program guide (EPG) of digital multimedia broadcasting (DMB), electronic service guide (ESG) of digital video broadcast-handheld (DVB-H), and the like.

The broadcast receiving module 111 may be configured to receive signals broadcast by using various types of broadcast systems. In particular, the broadcast receiving module 111 may receive a digital broadcast by using a digital broadcast system such as multimedia broadcasting-terrestrial (DMB-T), digital multimedia broadcasting-satellite (DMB-S), digital video broadcast-handheld (DVB-H), the data broadcasting system known as media forward link only (MediaFLO®), integrated services digital broadcast-terrestrial (ISDB-T), etc. The broadcast receiving module 111 may be configured to be suitable for abroad cast system that provides a broadcast signal as well as the above-mentioned digital broadcast systems.

Broadcast signals and/or broadcast-associated information received via the broadcast receiving module 111 may be stored in the memory 160.

The mobile communication module 112 transmits and/or receives radio signals to and/or from at least one of a base station, an external terminal and a server. Such radio signals may include a voice call signal, a video call signal or various types of data according to text and/or multimedia message transmission and/or reception.

The mobile communication module 112 may implement a video call mode and a voice call mode. The video call mode indicates a state of calling with watching a callee's image. The voice call mode indicates a state of calling without watching the callee's image. The wireless communication module 112 may transmit and receive at least one of voice and image in order to implement the video call mode and the voice call mode.

The wireless Internet module 113 supports wireless Internet access for the mobile terminal. This module may be internally or externally coupled to the mobile terminal 100. Examples of such wireless Internet access may include Wireless LAN (WLAN) (Wi-Fi), Wireless Broadband (Wibro), Worldwide Interoperability for Microwave Access (Wimax), High Speed Downlink Packet Access (HSDPA) and the like.

The short-range communication module 114 denotes a module for short-range communications. Suitable technologies for implementing this module may include BLUETOOTH™, Radio Frequency IDentification (RFID), Infrared Data Association (IrDA), Ultra-WideBand (UWB), ZigBee™, Near Field Communication (NFC), and the like.

The location information module 115 denotes a module for detecting or calculating a position of a mobile terminal. An example of the location information module 115 may include a Global Position System (GPS) module or a Wireless Fidelity (Wi-Fi) module.

Still referring to FIG. 1, the A/V input unit 120 is configured to provide audio or video signal input to the mobile terminal. The A/V input unit 120 may include a camera 121 and a microphone 122. The camera 121 receives and processes image frames of still pictures or video obtained by image sensors in a video call mode or a capturing mode. The processed image frames may be displayed on a display unit 151.

The image frames processed by the camera 121 may be stored in the memory 160 or transmitted to the exterior via the wireless communication unit 110. Also, user's position information and the like may be calculated from the image frames acquired by the camera 121. Two or more cameras 121 may be provided according to the configuration of the mobile terminal.

The microphone 122 may receive an external audio signal while the mobile terminal is in a particular mode, such as a phone call mode, a recording mode, a voice recognition mode, or the like. This audio signal is processed into digital data. The processed digital data is converted for output into a format transmittable to a mobile communication base station via the mobile communication module 112 in case of the phone call mode. The microphone 122 may include assorted noise removing algorithms to remove noise generated in the course of receiving the external audio signal.

The user input unit 130 may generate input data input by a user to control the operation of the mobile terminal. The user input unit 130 may include a keypad, a dome switch, a touchpad (e.g., static pressure/capacitance), a jog wheel, a jog switch and the like.

The sensing unit 140 provides measurements by one or more sensors that are communicative with the mobile terminal 100. For example, such sensors may be configured to detect various conditions of the mobile terminal and/or various conditions (e.g., biological information) of a user who utilizes the mobile terminal.

For example, the sensing unit 140 may detect various conditions of a mobile terminal, such as an open/close status of the mobile terminal, a change in a location of the mobile terminal 100, a presence or absence of user contact with the mobile terminal 100, the location of the mobile terminal 100, acceleration/deceleration of the mobile terminal 100, and the like, so as to generate a sensing signal for controlling the operation of the mobile terminal 100. For example, regarding a slide-type mobile terminal, the sensing unit 140 may sense whether a sliding portion of the mobile terminal is open or closed. Other examples include sensing functions, such as the sensing unit 140 sensing the presence or absence of power provided by the power supply 190, the presence or absence of a coupling or other connection between the interface unit 170 and an external device. As shown in the example of FIG. 1, the sensing unit 140 may include various sensors, such as a proximity sensor 141, a stereoscopic touch sensing unit 142, an ultrasound sensing unit 143, and a camera sensing unit 144.

The mobile terminal 100 may include one or more proximity sensors (e.g., proximity sensor 141) to detect proximity of different body parts of a user to different portions of the mobile terminal 100. As examples, in some implementations, the proximity sensor 141 may be used to detect proximity of a user's finger (or stylus, or other object used for pointing) to a display screen of the mobile terminal 100. An example of using a proximity sensor to detect proximity of a user's pointer to a display screen will be described below, in the context of controlling a display unit.

In some implementations, a mobile terminal may also include sensors that detect biological information regarding a user. In the example of FIG. 1, the mobile terminal 100 includes a biological information obtainment unit 145 that obtains biological information through a user's specific body portion. In some implementations, the biological information obtainment unit 145 may be separate from the sensing unit 140 (as shown in FIG. 1). Alternatively, in some implementations, the biological information obtainment unit 145 may be part of the sensing unit 140.

The biological information obtainment unit 145 may include one or more sensors that measure a bio-signal that is generated by physiological potential in the human body. For example, a sensor may sense a state of a user's skin or a signal of a user's living body. The sensor may be configured to include at least one among a pulse plethyamography (PPG) sensor, an electro-cardiogram (ECG) sensor, a galvanic skin reflex (GSR) sensor, an electro-encephalogram (EEG) sensor, an electro-myogram (EMG) sensor, and an electro-oculography (EOG) sensor. These sensors measure a pulse blood flow, an electrocardiogram, a galvanic skin reflex, an electro-encephalogram, an electro-myogram, and a bio-signal by eye movements.

The biological information obtainment unit 145 may also include a sensor that senses a movement of a user's muscle. For example, one or more muscle sensors may contact the skin surface of the user's wrist region and detect muscle movement. An example of a muscle sensor is described with reference to FIG. 3B, below.

Still referring to FIG. 1, the output unit 150 is configured to output an audio signal, a video signal or a tactile signal. The output unit 150 may include a display unit 151, an audio output module 153, an alarm unit 154 and a haptic module 155.

The display unit 151 may output information processed in the mobile terminal 100. For example, when the mobile terminal is operating in a phone call mode, the display unit 151 will provide a User Interface (UI) or a Graphic User Interface (GUI), which includes information associated with the call. As another example, if the mobile terminal is in a video call mode or a capturing mode, the display unit 151 may additionally or alternatively display images captured and/or received, UI, or GUI.

The display unit 151 may be implemented using, for example, at least one of a Liquid Crystal Display (LCD), a Thin Film Transistor-Liquid Crystal Display (TFT-LCD), an Organic Light-Emitting Diode (OLED), a flexible display, a three-dimensional (3D) display and an e-ink display.

Some of such displays 151 may be implemented as a transparent type or an optical transparent type through which the exterior is visible, which is referred to as 'transparent display'. A representative example of the transparent display may include a Transparent OLED (TOLED), and the like. The rear surface of the display unit 151 may also be implemented to be optically transparent. Under this configuration, a user can view an object positioned at a rear side of a terminal body through a region occupied by the display unit 151 of the terminal body.

The display unit 151 may be implemented in two or more in number according to a configured aspect of the mobile terminal 100. For instance, a plurality of the displays 151 may be arranged on one surface to be spaced apart from or integrated with each other, or may be arranged on different surfaces.

The display unit 151 may also be implemented as a stereoscopic display unit 152 for displaying stereoscopic images.

In some implementations, the stereoscopic image may be a three-dimensional (3D) stereoscopic image, and the 3D stereoscopic image is an image refers to an image making a viewer feel that a gradual depth and reality of an object on a monitor or a screen corresponds to a reality space. A 3D stereoscopic image is implemented by using binocular disparity. Binocular disparity refers to disparity made by the positions of two eyes. When two eyes view different 2D images, the images are transferred to the brain through the retina and combined in the brain to provide the perception of depth and reality sense.

The stereoscopic display unit 152 may employ a stereoscopic display scheme such as stereoscopic scheme (a glass scheme), an auto-stereoscopic scheme (glassless scheme), a projection scheme (holographic scheme), or the like. Stereoscopic schemes commonly used for home television receivers, or the like, include Wheatstone stereoscopic scheme, or the like.

The auto-stereoscopic scheme includes, for example, a parallax barrier scheme, a lenticular scheme, an integral imaging scheme, or the like. The projection scheme includes a reflective holographic scheme, a transmissive holographic scheme, or the like.

In general, a 3D stereoscopic image is comprised of a left image (a left eye image) and a right image (a right eye image). According to how left and right images are combined into a 3D stereoscopic image, the 3D stereoscopic imaging method is divided into a top-down method in which left and right images are disposed up and down in a frame, an L-to-R (left-to-right, side by side) method in which left and right images are disposed left and right in a frame, a checker board method in which fragments of left and right images are disposed in a tile form, an interlaced method in which left and right images are alternately disposed by columns and rows, and a time sequential (or frame by frame) method in which left and right images are alternately displayed by time.

Also, as for a 3D thumbnail image, a left image thumbnail and a right image thumbnail are generated from a left image and a right image of the original image frame, respectively, and then combined to generate a single 3D thumbnail image. In general, thumbnail refers to a reduced image or a reduced still image. The thusly generated left image thumbnail and the right image thumbnail are displayed with a horizontal distance difference there between by a depth corresponding to the disparity between the left image and the right image on the screen, providing a stereoscopic space sense.

As illustrated, a left image and a right image for implementing a 3D stereoscopic image is displayed on the stereoscopic display unit 152 by a stereoscopic processing unit. The stereoscopic processing unit may receive the 3D image and extract the left image and the right image, or may receive the 2D image and change it into a left image and a right image.

In some implementations, if the display unit 151 and a touch sensitive sensor (referred to as a touch sensor) have a layered structure there between (referred to as a 'touch screen'), the display unit 151 may be used as an input device as well as an output device. The touch sensor may be implemented as a touch film, a touch sheet, a touchpad, and the like.

The touch sensor may be configured to convert changes of a pressure applied to a specific part of the display unit 151, or a capacitance occurring from a specific part of the display unit 151, into electric input signals. Also, the touch sensor may be configured to sense not only a touched position and a touched area, but also touch pressure. In some implementations, a touch object is an object to apply a touch input onto the touch sensor. Examples of the touch object may include a finger, a touch pen, a stylus pen, a pointer or the like.

When touch inputs are sensed by the touch sensors, corresponding signals are transmitted to a touch controller. The touch controller processes the received signals, and then transmits corresponding data to the controller 180. Accordingly, the controller 180 may sense which region of the display unit 151 has been touched. Various sensors may be used to allow the display unit 151 to function as an input device, such as the sensors in the sensing unit 140 of FIG. 1.

Still referring to FIG. 1, a proximity sensor (e.g., proximity sensor 141) may be arranged at an inner region of the mobile terminal 100 covered by the touch screen, or near the touch screen. The proximity sensor 141 may be provided as one example of the sensing unit 140. The proximity sensor 141 indicates a sensor to sense presence or absence of an object approaching to a surface to be sensed, or an object disposed near a surface to be sensed, by using an electromagnetic field or infrared rays without a mechanical contact. The proximity sensor 141 may, in some implementations, have a longer lifespan and a more enhanced utility than a contact sensor.

The proximity sensor 141 may include a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and so on. When the touch screen is implemented as a capacitance type, proximity of a pointer to the touch screen is sensed by changes of an electromagnetic field. In this case, the touch screen (touch sensor) may be categorized into a proximity sensor.

Hereinafter, for the sake of brief explanation, a status that the pointer is positioned to be proximate onto the touch screen without contact will be referred to as 'proximity touch', whereas a status that the pointer substantially comes in contact with the touch screen will be referred to as 'contact touch'. For the position corresponding to the proximity touch of the pointer on the touch screen, such position corresponds to a position where the pointer faces perpendicular to the touch screen upon the proximity touch of the pointer.

The proximity sensor 141 senses proximity touch, and proximity touch patterns (e.g., distance, direction, speed, time, position, moving status, etc.). Information relating to the sensed proximity touch and the sensed proximity touch patterns may be output onto the touch screen.

When a touch sensor is overlaid on the stereoscopic display unit 152 in a layered manner (hereinafter, referred to as 'stereoscopic touch screen'), or when the stereoscopic display unit 152 and a 3D sensor sensing a touch operation are combined, the stereoscopic display unit 152 may also be used as a 3D input device.

As examples of the three dimensional sensor, the sensing units 140 is configured to include a proximity sensor 141, a three dimensional touch sensing unit 142, a ultrasound sensing unit 143, a camera sensing unit 144, and a biological information obtainment unit 145.

The proximity sensor 141 measures a distance between a sensing target object (for example, a user's finger or a stylus pen) with which a touch is applied without mechanical contact and a sensing surface using the strength of an electromagnetic field or infrared light. The terminal recognizes which part of a stereoscopic image is touched on using the distance. Particularly, a touch screen is a capacitive type, a proximity extent of the sensing target object is sensed with a change in an electric field due to the proximity of the sensing target object. The touch screen is configured in such a manner as to recognize a three dimensional touch using the proximity extent.

The three dimensional touch sensing unit 142 is configured to sense the strength of the touch that is applied to a touch screen or the time for which the touch is applied to the touch screen. For example, the three dimensional touch sensing unit 142 senses a pressure of the applied touch. The three dimensional touch sensing unit 142 determines that the higher the pressure of the touch being applied to an object is, the farther the object is positioned away from the touch screen.

The ultrasound sensing unit 143 is configured in such a manner that positional information on the sensing target object is recognized using ultrasound.

The ultrasound sensing unit 143, for example, is configured from an optical sensor and multiple ultrasound sensors. The optical sensor is formed in such a manner as to sense light, and the ultrasound sensor is formed in such a manner to sense ultrasound. Because light is faster than ultrasound, the time it takes for the light to arrive at the optical sensor is shorter than the time it takes the ultrasound to arrive at the ultrasound sensor. Therefore, a position of a source from which a wave originates is calculated using a difference in arrival time between the light and the ultrasound.

The camera sensing unit 144 includes at least one of a camera, a photo sensor, and a laser sensor.

For example, the camera and the laser sensor may be combined to detect a touch of the sensing object with respect to a 3D stereoscopic image. When distance information detected by a laser sensor is added to a 2D image captured by the camera, 3D information can be obtained.

In another example, a photo sensor may be laminated on the mobile terminal. The photo sensor is configured to scan a movement of the sensing object in proximity to the touch screen. In detail, the photo sensor includes photo diodes and transistors at rows and columns to scan content mounted on the photo sensor by using an electrical signal changing according to the quantity of applied light. Namely, the photo sensor calculates the coordinates of the sensing object according to variation of light to thus obtain position information of the sensing object.

The audio output module 153 may convert and output as sound audio data received from the wireless communication unit 110 or stored in the memory 160 in a call signal reception mode, a call mode, a record mode, a voice recognition mode, a broadcast reception mode, and the like. Also, the audio output module 153 may provide audible outputs related to a particular function performed by the mobile terminal 100 (e.g., a call signal reception sound, a message reception sound, etc.). The audio output module 153 may include a speaker, a buzzer or the like.

The alarm unit 154 outputs a signal for informing about an occurrence of an event of the mobile terminal 100. Events generated in the mobile terminal may include call signal reception, message reception, key signal inputs, a touch input etc. In addition to video or audio signals, the alarm unit 154 may output signals in a different manner, for example, using vibration to inform about an occurrence of an event. The video or audio signals may be also outputted via the audio output module 153, so the display unit 151 and the audio output module 153 may be classified as parts of the alarm unit 154.

A haptic module 155 generates various tactile effects the user may feel. A typical example of the tactile effects generated by the haptic module 155 is vibration. The strength and pattern of the haptic module 155 can be controlled. For example, different vibrations may be combined to be outputted or sequentially outputted.

Besides vibration, the haptic module 155 may generate various other tactile effects such as an effect by stimulation such as a pin arrangement vertically moving with respect to a contact skin, a spray force or suction force of air through a jet orifice or a suction opening, a contact on the skin, a contact of an electrode, electrostatic force, etc., an effect by reproducing the sense of cold and warmth using an element that can absorb or generate heat.

The haptic module 155 may be implemented to allow the user to feel a tactile effect through a muscle sensation such as fingers or arm of the user, as well as transferring the tactile effect through a direct contact. Two or more haptic modules 155 may be provided according to the configuration of the mobile terminal 100.

The memory 160 may store software programs used for the processing and controlling operations performed by the controller 180, or may temporarily store data (e.g., a phonebook, messages, still images, video, etc.) that are inputted or outputted. In addition, the memory 160 may store data regarding various patterns of vibrations and audio signals outputted when a touch is inputted to the touch screen.

The memory 160 may include at least one type of storage medium including a Flash memory, a hard disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, and an optical disk. Also, the mobile terminal 100 may be operated in relation to a web storage device that performs the storage function of the memory 160 over the internet.

The interface unit 170 serves as an interface with an external device connected with the mobile terminal 100. For example, the external devices may transmit data to an external device, receives and transmits power to elements of the mobile terminal 100, or transmits internal data of the mobile terminal 100 to an external device. For example, the interface unit 170 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating the authority of using the mobile terminal 100 and may include a user identity module (UIM), a subscriber identity module (SIM) a universal subscriber identity module (USIM), and the like. In addition, the device having the identification module (referred to as 'identifying device', hereinafter) may take the form of a smart card. Accordingly, the identifying device may be connected with the terminal 100 via the interface unit 170.

When the mobile terminal 100 is connected with an external cradle, the interface unit 170 may serve as a passage to allow power from the cradle to be supplied there through to the mobile terminal 100 or may serve as a passage to allow various command signals inputted by the user from the cradle to be transferred to the mobile terminal there through. Various command signals or power inputted from the cradle may operate as signals for recognizing that the mobile terminal is properly mounted on the cradle.

The controller 180 typically controls the general operations of the mobile terminal. For example, the controller 180 performs controlling and processing associated with voice calls, data communications, video calls, and the like. The controller 180 may include a multimedia module 181 for reproducing multimedia data. The multimedia module 181 may be configured within the controller 180 or may be configured to be separated from the controller 180.

The controller 180 may perform a pattern recognition processing to recognize a handwriting input or a picture drawing input performed on the touch screen as characters or images, respectively.

Also, the controller 180 may execute a lock state to restrict a user from inputting control commands for applications when a state of the mobile terminal meets a preset condition. Also, the controller 180 may control a lock screen displayed in the lock state based on a touch input sensed on the display unit 151 in the lock state of the mobile terminal.

The power supply unit 190 receives external power or internal power and supplies appropriate power for operating respective elements and components under the control of the controller 180.

Various implementations described herein may be implemented in a computer-readable or its similar medium using, for example, software, hardware, or any combination thereof.

For hardware implementation, the implementations described herein may be implemented by using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic units designed to perform the functions described herein. In some cases, such implementations may be implemented by the controller 180 itself.

For software implementation, procedures or functions described herein may be implemented by separate software modules. Each software module may perform one or more functions or operations described herein.

Software codes can be implemented by a software application written in any suitable programming language. The software codes may be stored in the memory 160 and executed by the controller 180.

Hereinafter, a communication system which is operable with the mobile terminal 100 according to the present disclosure will be described.

Figure 2A:
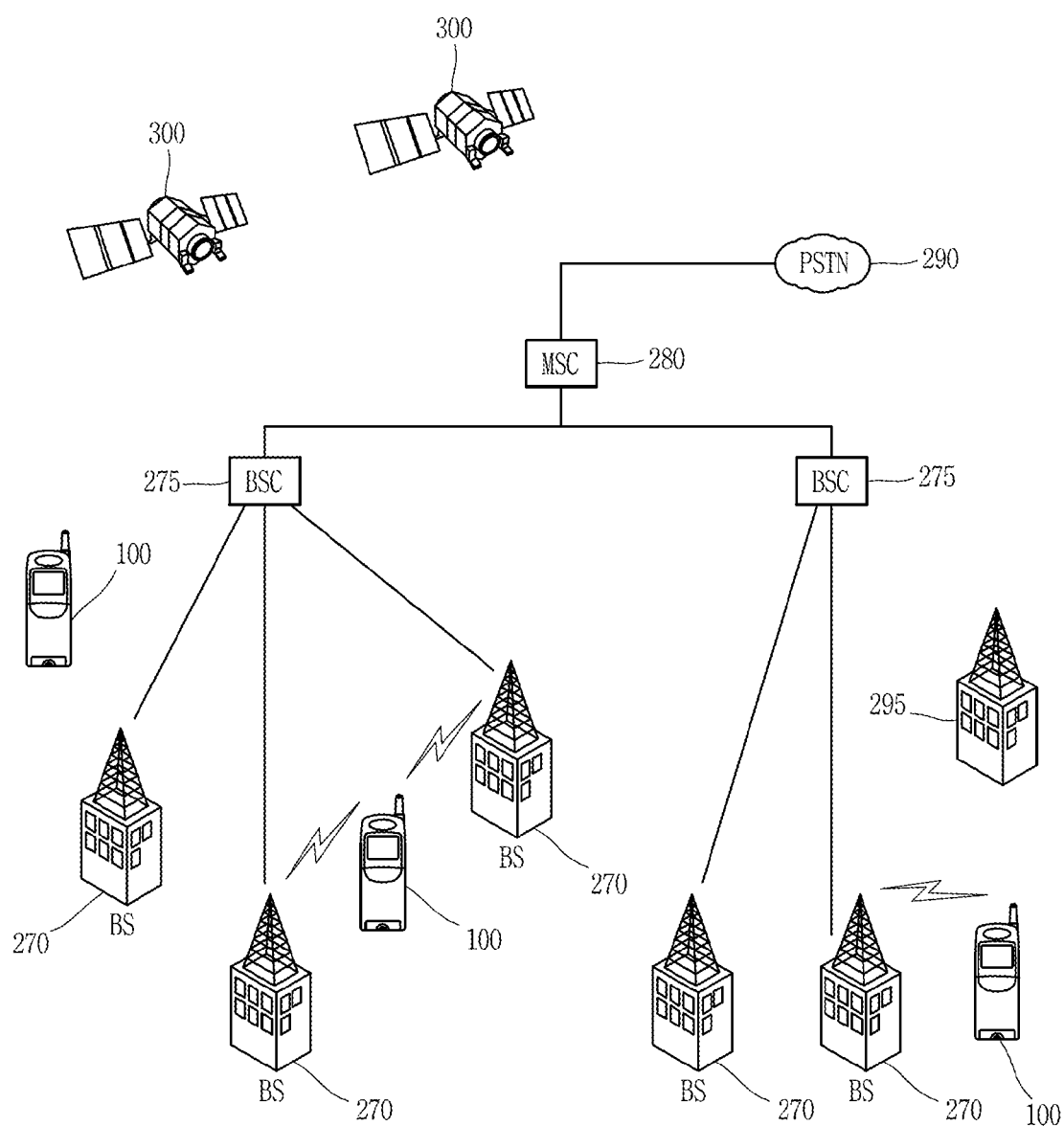
FIGS. 2A and 2B are diagrams illustrating a communication system in which a mobile terminal is operable.
Figure 2B:
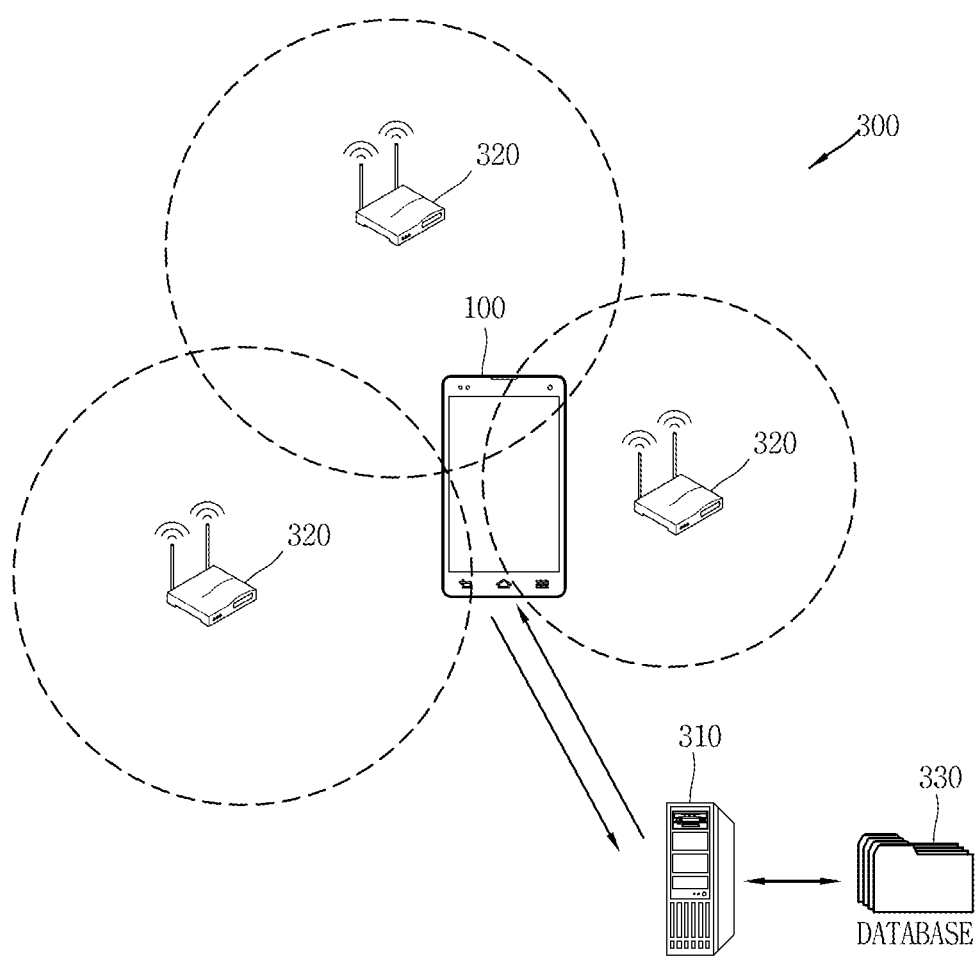

FIGS. 2A and 2B are conceptual views of a communication system operable with a mobile terminal 100 in accordance with the present disclosure.

First, referring to FIG. 2A, such communication systems utilize different air interfaces and/or physical layers.

Examples of such air interfaces utilized by the communication systems include Frequency Division Multiple Access (FDMA), Time Division Multiple Access (TDMA), Code Division Multiple Access (CDMA), and Universal Mobile Telecommunications System (UMTS), the Long Term Evolution (LTE) of the UMTS, the Global System for Mobile Communications (GSM), and the like.

By way of non-limiting example only, further description will relate to a CDMA communication system, but such teachings apply equally to other system types including the CDMA wireless communication system.

Referring now to FIG. 2A, a CDMA wireless communication system is shown having a plurality of mobile terminal s 100, a plurality of base stations (BSs) 270, base station controllers (BSCs) 275, and a mobile switching center (MSC) 280. The MSC 280 is configured to interface with a conventional Public Switch Telephone Network (PSTN) 290. The MSC 280 is also configured to interface with the BSCs 275. The BSCs 275 are coupled to the base stations 270 via backhaul lines. The backhaul lines may be configured in accordance with any of several interfaces including, for example, E1/T1, ATM, IP, PPP, Frame Relay, HDSL, ADSL, or xDSL. Hence, the plurality of BSCs 275 can be included in the system as shown in FIG. 2A.

The base station 270 may include one or more sectors, the sector having an omni-directional antenna or an antenna pointed in a particular direction radially away from the base station 270. Alternatively, the sector may include two or more different antennas. The base station 270 may be configured to support a plurality of frequency assignments, with the frequency assignment having a particular spectrum (e.g., 1.25 MHz, 5 MHz, etc.).

The intersection of sector and frequency assignment may be referred to as a CDMA channel. The base stations 270 may also be referred to as Base Station Transceiver Subsystems (BTSs). In some cases, the term "base station" may be used to refer collectively to a BSC 275, and one or more base stations 270. The base stations may also be denoted as "cell sites." Alternatively, individual sectors of a given base station 270 may be referred to as cell sites.

A broadcasting transmitter (BT) 295, as shown in FIG. 2A, transmits a broadcast signal to the mobile terminal s 100 operating within the system. The broadcast receiving module 111 (FIG. 1) is typically configured inside the mobile terminal 100 to receive broadcast signals transmitted by the BT 295.

FIG. 2A further depicts several Global Positioning System (GPS) satellites 300. Such satellites 300 facilitate locating the position of at least one of plural mobile terminal s 100. Two satellites are depicted in FIG. 2, but it is understood that useful position information may be obtained with greater or fewer satellites than two satellites. The GPS module 115 (FIG. 1) is typically configured to cooperate with the satellites 300 to obtain desired position information. It is to be appreciated that other types of position detection technology, (i.e., location technology that may be used in addition to or instead of GPS location technology) may alternatively be implemented. If desired, at least one of the GPS satellites 300 may alternatively or additionally be configured to provide satellite DMB transmissions.

During typical operation of the wireless communication system, the base stations 270 receive sets of reverse-link signals from various mobile terminals 100. The mobile terminals 100 are engaging in calls, messaging, and executing other communications. The reverse-link signal received by a given base station 270 is processed within that base station 270. The resulting data is forwarded to an associated BSC 275. The BSC 275 provides call resource allocation and mobility management functionality including the orchestration of soft handoffs between base stations 270. The BSCs 275 also route the received data to the MSC 280, which then provides additional routing services for interfacing with the PSTN 290. Similarly, the PSTN 290 interfaces with the MSC 280, and the MSC 280 interfaces with the BSCs 275, which in turn control the base stations 270 to transmit sets of forward-link signals to the mobile terminal s 100.

Hereinafter, description will be given of a method for acquiring location information of a mobile terminal using a wireless fidelity (WiFi) positioning system (WPS), with reference to FIG. 2B.

The WiFi positioning system (WPS) 300 refers to a location determination technology based on a wireless local area network (WLAN) using WiFi as a technology for tracking the location of the mobile terminal 100 using a WiFi module provided in the mobile terminal 100 and a wireless access point 320 for transmitting and receiving to and from the WiFi module.

The WiFi positioning system 300 may include a WiFi location determination server 310, a mobile terminal 100, a wireless access point (AP) 320 connected to the mobile terminal 100, and a database 330 stored with any wireless AP information.

The WiFi location determination server 310 extracts the information of the wireless AP 320 connected to the mobile terminal 100 based on a location information request message (or signal) of the mobile terminal 100. The information of the wireless AP 320 may be transmitted to the WiFi location determination server 310 through the mobile terminal 100 or transmitted to the WiFi location determination server 310 from the wireless AP 320.

The information of the wireless AP extracted based on the location information request message of the mobile terminal 100 may be at least one of MAC address, SSID, RSSI, channel information, privacy, network type, signal strength and noise strength.

The WiFi location determination server 310 receives the information of the wireless AP 320 connected to the mobile terminal 100 as described above, and compares the received wireless AP 320 information with information contained in the pre-established database 330 to extract (or analyze) the location information of the mobile terminal 100.

In some implementations, referring to FIG. 2B, as an example, the wireless AP connected to the mobile terminal 100 is illustrated as a first, a second, and a third wireless AP 320. However, the number of wireless APs connected to the mobile terminal 100 may be changed in various ways according to a wireless communication environment in which the mobile terminal 100 is located. When the mobile terminal 100 is connected to at least one of wireless APs, the WiFi positioning system 300 can track the location of the mobile terminal 100.

Next, considering the database 330 stored with any wireless AP information in more detail, various information of any wireless APs disposed at different locations may be stored in the database 330.

The information of any wireless APs stored in the database 330 may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like.

In this manner, any wireless AP information and location information corresponding to the any wireless AP are stored together in the database 330, and thus the WiFi location determination server 310 may retrieve wireless AP information corresponding to the information of the wireless AP 320 connected to the mobile terminal 100 from the database 330 to extract the location information matched to the searched wireless AP, thereby extracting the location information of the mobile terminal 100.

Furthermore, the extracted location information of the display device 100 may be transmitted to the display device 100 through the WiFi location determination server 310, thereby acquiring the location information of the display device 100.

Types of realization of the mobile terminal, disclosed in the present specification, according to some implementations, are described below referring to FIGS. 3A, 3B (describing a smart watch implementation of a mobile terminal), and FIGS. 4A, 4B (describing a wearable glasses implementation of a mobile terminal), and FIGS. 5A, 5B (describing another implementation of a mobile terminal).

Figure 3A:
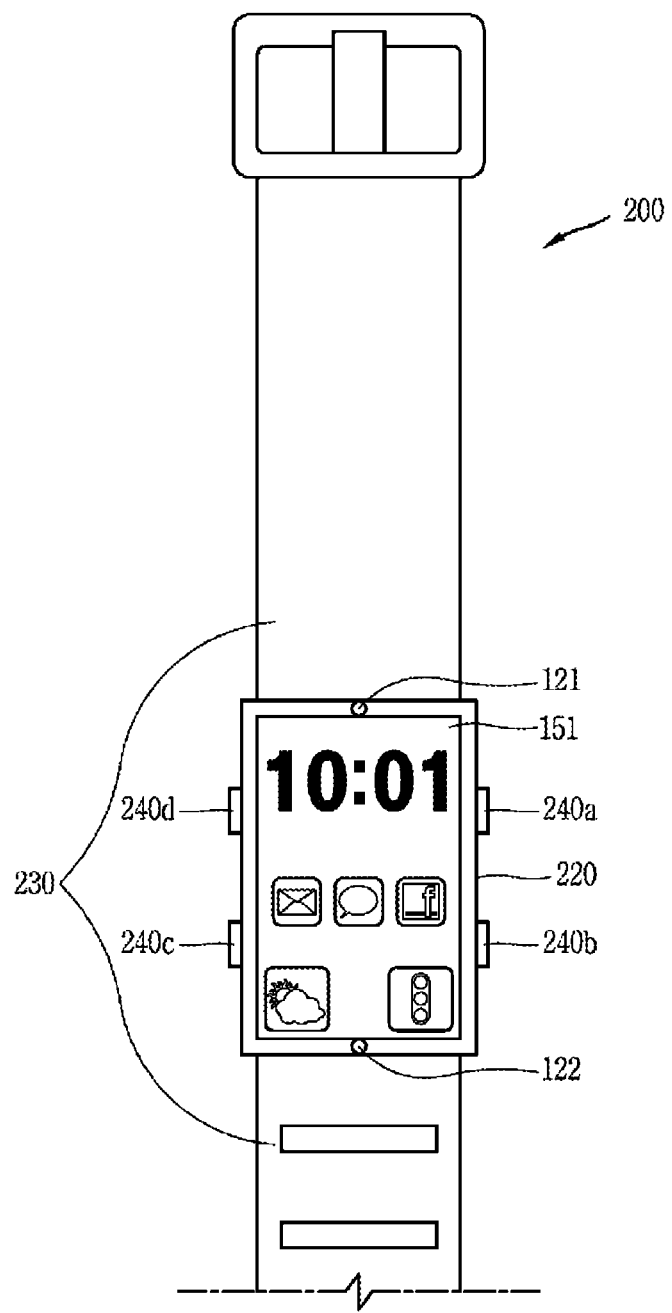
FIGS. 3A and 3B are diagrams illustrating examples of a front and rear of a smart watch type of mobile terminal.
Figure 3B:
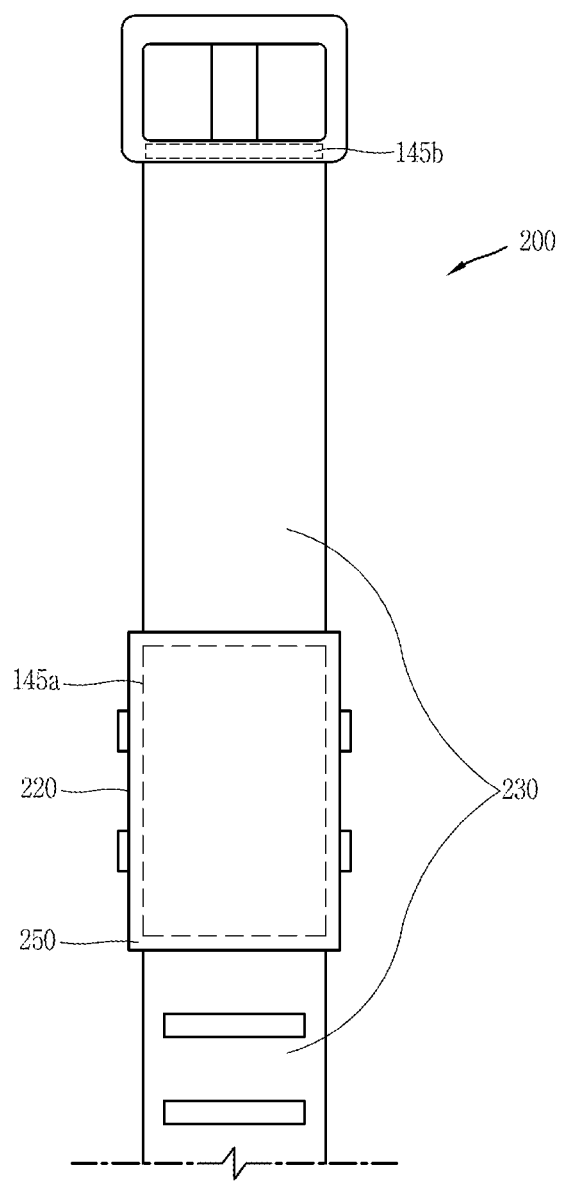

FIGS. 3A and 3B are diagrams illustrating a front side and a rear side of a smart watch according to some implementations.

That is, FIGS. 3A and 3B illustrate a case where the mobile terminal 100 takes the form of a smart watch, which is a watch-type mobile terminal, among wearable devices.

A smart watch 200 that is disclosed in the present specification has rectangular construction. However, implementations are not limited to this, and may be applied to a smart watch having various types of constructions in the shape of a circle, a triangle, or the like.

The smart watch 200 includes a band 230 and a body 220. A case forming an appearance of the body 220 may include a front case 210 and a rear case 250. A space formed by the front case 210 and the rear case 250 may accommodate various components therein. At least one intermediate case may further be disposed between the front case 210 and the rear case 250. Such cases may be formed by injection-molded synthetic resin, or may be formed using a metallic material such as stainless steel (STS) or titanium (Ti).

Referring to FIG. 3A, a display unit 151, a camera 121, a microphone 122, and the like are arranged in the front case 210.

The display 151 occupies most parts of a main surface of the front case 210. A camera 121 and a microphone 122 may be arranged at two ends of the display unit 151.

Various types of visual information may be displayed on the display unit 151. Such information may be displayed in the form of texts, numbers, signs, graphics or icons.

For input of such information, at least one of the texts, numbers, signs, graphics or icons may be arranged in the form of a keypad. Such keypad may be called 'soft key'.

The display unit 151 may be operated as an entire region, or as a plurality of divided regions. In the latter case, the plurality of regions may be associated with each other.

In addition, a wire/wireless headset port (not illustrated) and a wire/wireless data port (not illustrated) are arranged on one lateral face of a main body of the smart watch 200. These ports are configured as one example of an interface 170 (refer to FIG. 1).

Referring to FIG. 3B, a first sensor 145*a* is arranged on a rear face of the main body 220, that is, a rear case 250. The first sensor 145*a* is a sensor that senses a state of a user's skin or a signal of a user' living body. In addition, a second sensor 145*b* that senses a movement of a user's muscle and the like is arranged on a band 230 of a smart watch.

An antenna for receiving broadcast signals may be disposed on a side surface of the body 220. The antenna, part of the broadcast receiving module 11*l* (refer to FIG. 1) may be provided in the body 220 in a retractable manner.

Then, an audio output module (not illustrated), an interface, and the like are arranged in the main body 220 of the smart watch 200. In addition, a user input unit 240, a connection port, and the like are arranged lateral faces of the front case 210 and the rear case 250.

The user input unit 240 is operated to receive a command for controlling the operation of the smart watch 200, which may include at least one of manipulation units 240*a*, 240*b*, 240*c* and 240*d*. The manipulation units may be referred to as manipulating portions, and may include any type of ones that can be manipulated in a user's tactile manner.

Commands inputted through the manipulation units may be variously set. For instance, the manipulation units may be configured to input commands such as START, END, SCROLL or the like, and configured to input commands for controlling a level of sound outputted from the audio output unit 153, or commands for converting the current mode of the display 151 to a touch recognition mode.

A connection port may be configured to receive data from an external device or to receive power, thereby transmitting it to components inside the smart watch 200. Alternatively, the connection port may be configured to allow data inside the smart watch 200 to be transmitted to an external device. The connection port may be configured as one example of the interface unit 170 (refer to FIG. 1).

A power supply unit (not illustrated) that supplies electric power to the smart watch 200 is installed in the main body 220 of the smart watch 200. The power supply unit is configured to be in the form suitable to be built into the main body 220.

Figure 4A:
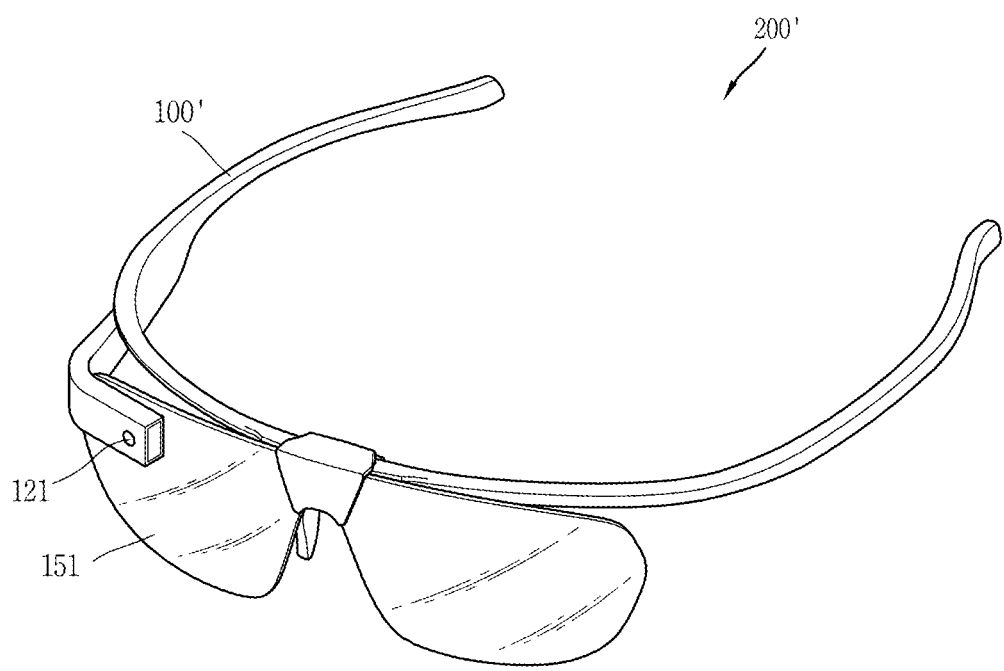
FIGS. 4A and 4B are diagram illustrating examples of a wearable glasses-type mobile terminal.
Figure 4B:
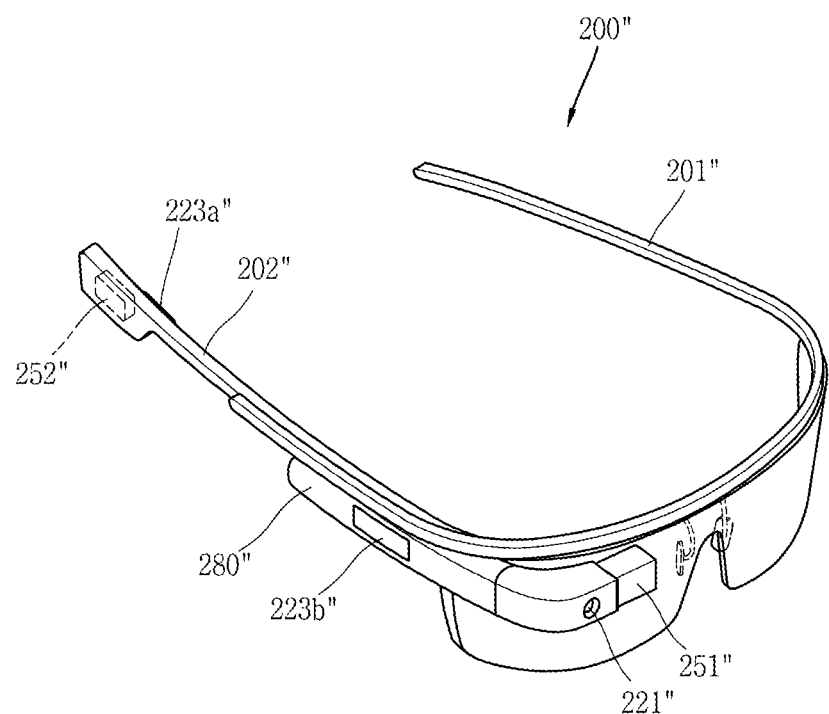

FIGS. 4A and 4B are diagrams of examples of a wearable glasses-type mobile terminal.

FIGS. 4A and 4B illustrate a mobile terminal 100 realized as digital eye glasses (e.g., smart glasses), which is an eye-glass-type mobile terminal, among wearable devices.

Referring to FIG. 4A, a wearable glasses-type terminal 200', according to some implementations, is configured to include a main body 100', a display unit 151, a controller 180.

The wearable glasses-type terminal 200', according to some implementations may further include a user input unit, a voice recognition unit, and a motion sensing unit.

The wearable glasses-type terminal 200', according to some implementations, is realized as a head-mounted display (HMD). As a specific example, the wearable glasses-type terminal 200' is realized as smart glasses.

The main body 100' is formed in such a manner that it is mountable on the human head. For example, the main body 100' is realized as a frame of smart glasses worn over a user's eyes.

In the example of FIG. 4A, the display units 151, coupled with the main body 100', are arranged in positions that correspond to both eyes, respectively.

In addition, the display unit 151 has optical transparency, and visual information is output to the display unit 151.

The visual information is generated in the wearable glasses-type terminal 200', or may be based on a virtual object that is input from an external device. For example, the virtual object may be based on an application, an icon corresponding to the application, content, a UI for a communication mode or the like. The virtual object may be generated by the controller 180 or input from the mobile terminal or any other device, such as a smart phone.

In some implementations, if the display unit 151 has optical transparency, the user can view an external environment through the display unit 151.

In addition, according to some implementations, the external environment may be viewed through the display unit 151 and at the same time, information regarding object in the external environment may be output to the display unit 151. For example, the external object may be a business card, a human being, or an external device with which mutual communication is possible.

As described above, the controller 180 controls the wearable glasses-type terminal 200'. Specifically, the controller 180 outputs information on the external device, which is sensed in a wireless communication unit 110, to the display unit 151.

For example, the controller 180 may identify a position of the sensed external device. In some implementations, the controller 180 determines whether or not the sensed external device is positioned within a user's sight and based on a result of this determination, determines whether or not the information on the sensed external device will be output.

The controller 180 may be mounted on the main body 100' of the wearable glasses-type terminal 200' or the controller 180 and the main body 100 may be integrally formed into one piece. According to some implementations, the controller 180 may be arranged away from the main body 100'.

The camera 121 may be arranged in front of at least one of the left-eye and right-eye display units 151. Alternatively, the camera 121 may be arranged on one side or both sides of the frame 100' and thus may photograph an object that is out of the wearer's line of sight.

The user input unit 130 may be realized as a separate touch panel that is provided on one side or both sides of the frame 100' Alternatively, the user input unit 130 may be realized as a physical input key. For example, an ON/OFF switch for a power source may be realized in such a manner that it is provided on one side of the frame 100'.

According to some implementations, the user input unit 130 may be realized as a separate external device that is connected to the main body 100'. Accordingly, the user can input a specific command into the separate external device. Alternatively, the display unit 151 may be realized as a touch screen, and thus the user can input a control command directly into the display unit 151.

According to some implementations, the user input unit 130 may be realized as a module that recognizes a user's voice command. Accordingly, the user can input a specific voice command into the main body 100'.

In addition to the functions described above, the wearable glasses-type terminal maybe configured to execute any suitable function that can be executed in other types of mobile terminals.

In some implementations, the external environment that is seen through the display unit 151 and the visual information being output are displayed together on the display unit 151 of the smart glasses (this is referred to as an augmented reality). Accordingly, the user can more easily grasp the information on the arbitrary object that makes up the external environment.

In addition, the smart glasses performs wireless communication with other different smart glasses or with the external device that is capable of communicating with the smart glasses. As such, various types of information relating to external devices may be output to the display unit 151.

FIG. 4B is a perspective view illustrating an example of a wearable device in which an eye-proximity display can be mounted.

Referring to FIG. 4B, the wearable device is a glass-type mobile terminal 200'', which can be wearable on a head of a human body and be provided with a frame (case, housing, etc.). In some implementations, the frame may be made of a flexible material to be easily worn. The frame of mobile terminal 200'' is shown having a first frame 201'' and a second frame 202'', which can be made of the same or different materials.

The frame may be supported on the head and defines a space for mounting various components. As illustrated, electronic components, such as a control module 280'', an audio output module 252'', and the like, may be mounted to the frame part. Also, a display unit 251'' for covering either or both of the left and right eyes may be detachably coupled to the frame part.

The control module 280'' controls various electronic components disposed in the mobile terminal 200''. The control module 280'' may be understood as a component corresponding to the aforementioned controller 180 (refer to FIG. 1). FIG. 4B illustrates that the control module 280'' is installed in the frame part on one side of the head, although other locations are possible.

The display unit 251'' may be implemented as a head mounted display (HMD). The HMD refers to display techniques by which a display is mounted to a head to show an image directly in front of a user's eyes. In order to provide an image directly in front of the user's eyes when the user wears the glass-type mobile terminal 200'', the display unit 251'' may be located to correspond to either or both of the left and right eyes. FIG. 4B illustrates that the display unit 251'' is located on a portion corresponding to the right eye to output an image viewable by the user's right eye.

In some implementations, the display unit 251'' may project an image into the user's eye using a prism. Also, the prism may be formed from optically transparent material such that the user can view both the projected image and a general visual field (a range that the user views through the eyes) in front of the user.

In such a manner, the image output through the display unit 251'' may be viewed while overlapping with the general visual field of the user. The mobile terminal 200'' may provide an augmented reality (AR) by overlaying a virtual image on a realistic image or background using the display.

The camera 221'' may be located adjacent to either or both of the left and right eyes to capture an image, and the camera 221'' can acquire a scene that the user is currently viewing.

In the drawings, the camera 221'' is provided at the control module 280''. However, the camera 221'' may be positioned at any suitable location of the mobile terminal. In some implementations, multiple cameras 221'' may be utilized. Such multiple cameras 221'' may be used, for example, to acquire a stereoscopic image, or for other purposes.

The glass-type mobile terminal 200'' may include user input units 223a'' and 223b'', which can be manipulated by the user to provide an input. The user input units 223a'' and 223b'' may employ techniques which permit input via a tactile input. Tactile inputs can include a touch, push, or the like. The user input units 223a'' and 223b'' are shown operable in a pushing manner and a touching manner as they are located on the frame part and the control module 280'', respectively.

If desired, the mobile terminal 200'' may include a microphone which processes input sound into electric audio data, and an audio output module 252'' for outputting audio. The audio output module 252" may be configured to produce audio in a general audio output manner or an osteoconductive manner. When the audio output module 252" is implemented in the osteoconductive manner, the audio output module 252" may be closely adhered to the head when the user wears the mobile terminal 200" and vibrate the user's skull to transfer sounds.

Hereinafter, a structure of the mobile terminal of FIG. 1 according to some implementations will be explained with reference to FIGS. 5A and 5B.

Figure 5A:
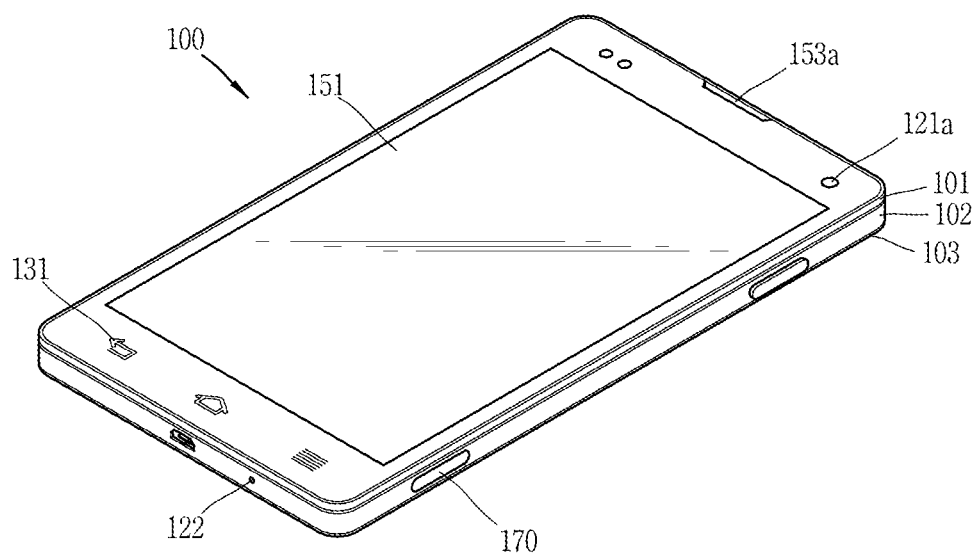
FIGS. 5A and 5B are perspective diagrams illustrating examples of a mobile terminal.

FIG. 5A is a front perspective view of an example of a mobile terminal according to some implementations.

In this example, the mobile terminal 100 is a bar type mobile terminal. However, the present disclosure is not limited to this, but may be applied to a watch type, a clip type, a glasses-type, or a slide type in which two or more bodies are coupled to each other so as to perform a relative motion, a folder type motion, a swing type motion, a swivel type motion and the like.

A body of the mobile terminal 100 includes a case (casing, housing, cover, etc.) forming an outer appearance. The case may include a front case 101 and a rear case 102. A space formed by the front case 101 and the rear case 102 may accommodate various components therein. At least one intermediate case may further be disposed between the front case 101 and the rear case 102. A battery cover 103 for covering a battery 191 may be detachably mounted to the rear case 102.

Such cases may be formed by injection-molded synthetic resin, or may be formed using a metallic material such as stainless steel (STS) or titanium (Ti).

A display 151, a first audio output module 153a, a first camera 121a, a first manipulation unit 131, etc. may be disposed on a front surface of the body. A microphone 122, an interface unit 170, a second manipulation unit 132, etc. may be provided on a side surface of the body.

The display unit 151 may output information processed in the mobile terminal 100. The display unit 151 may be implemented using, for example, at least one of a Liquid Crystal Display (LCD), a Thin Film Transistor-Liquid Crystal Display (TFT-LCD), an Organic Light-Emitting Diode (OLED), a flexible display, a three-dimensional (3D) display and an e-ink display.

The display unit 151 may include a touch sensing means for inputting information in a touch manner. Once part on the display unit 151 is touched, the content corresponding to the touched position is input. The content input in a touch manner, may be characters, or numbers, or menu items which can be set in each mode.

The touch sensing means may be transmissive so that visual information output from the display unit 151 can be viewed, and may include a structure for enhancing visibility of the touch screen at a bright place. Referring to FIG. 5A, the display unit 151 occupies most of the front surface of the front case 101.

The first audio output module 153a and a first camera 121 are arranged at a region adjacent to one end of the display unit 151, and the first manipulation unit 131 and the microphone 122 are arranged at a region adjacent to another end of the display unit 151. The second manipulation unit 132 (refer to FIG. 5B), the interface unit 170, etc. may be arranged on side surfaces of the body.

The first audio output module 153a may be implemented as a receiver for transmitting a call sound to a user's ear, or a loud speaker for outputting each type of alarm sound or a playback sound of multimedia.

A sound generated from the first audio output module 153 may be configured to be emitted through an assembly gap between structures. In this case, a hole independently formed to output audio sounds may not be seen or is otherwise hidden in terms of appearance, thereby further simplifying the appearance and manufacturing of the mobile terminal 100. Implementations are not limited to this. The hole for outputting audio sounds may be formed at a window.

The first camera 121a processes image frames such as still images or moving images, obtained by an image sensor in a video call mode or a capturing mode. The processed image frames may be displayed on the display unit 151.

The user input unit 130 is manipulated to receive a command for controlling the operation of the mobile terminal 100, and may include a first manipulation unit 131 and a second manipulation unit 132. The input keys may be referred to as manipulation portions, and may include any type of ones that can be manipulated in a user's tactile manner.

In the present drawing, it is illustrated on the basis that the first manipulation unit 131 is a touch key, but the present disclosure may not be necessarily limited to this. For example, the first manipulation unit 131 may be configured with a mechanical key, or a combination of a touch key and a mechanical key.

The content received by the first and/or second manipulation units 131, 132 may be set in various ways. For example, the first manipulation unit 131 may be used to receive a command such as menu, home key, cancel, search, or the like, and the second manipulation unit 132 may receive a command, such as controlling a volume level being outputted from the first audio output module 153a, or switching into a touch recognition mode of the display unit 151.

The microphone 122 may be formed to receive the user's voice, other sounds, or the like. The microphone 122 may be provided at a plurality of places, and configured to receive stereo sounds.

The interface unit 170 serves as a path allowing the mobile terminal 100 to exchange data with external devices. For example, the interface unit 170 may be at least one of a connection terminal for connecting to an earphone in a wired or wireless manner, a port for near field communication (for example, an Infrared Data Association (IrDA) port, a Bluetooth port, a wireless LAN port, and the like), and a power supply terminal for supplying power to the mobile terminal 100. The interface unit 170 may be implemented in the form of a socket for accommodating an external card such as Subscriber Identification Module (SIM) or User Identity Module (UIM), and a memory card for information storage.

Figure 5B:
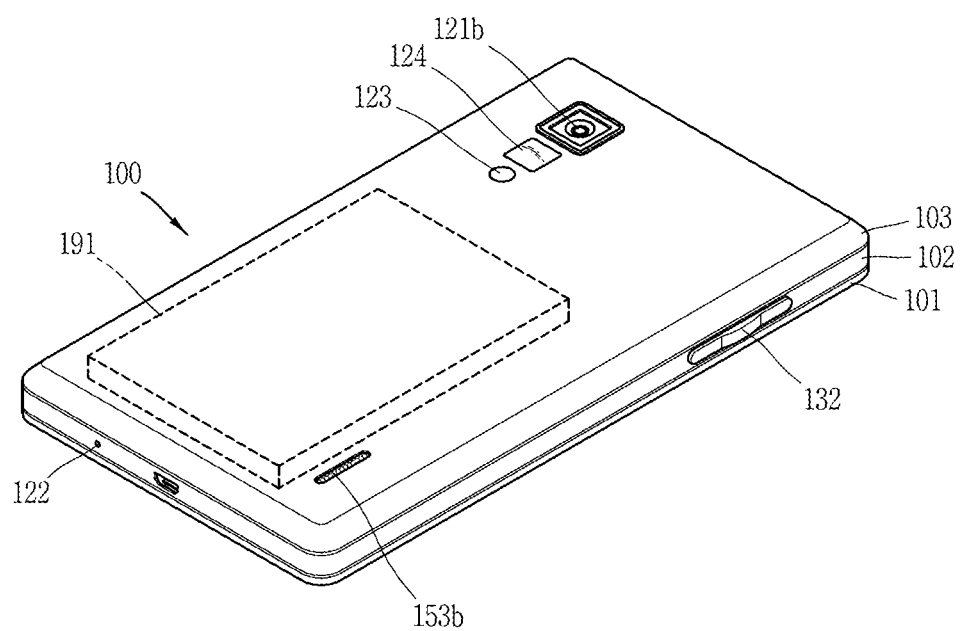

FIG. 5B is a rear perspective view of an example of a mobile terminal.

Referring to FIG. 5B, a second camera 121b may be additionally mounted at a rear surface of the terminal body, namely, the rear case 102. The second camera 121b has an image capturing direction, which is substantially opposite to the direction of the first camera unit 121a (e.g., in FIG. 5A), and may have a different number of pixels from that of the first camera unit 121a.

For example, the first camera 121a may have a relatively small number of pixels enough not to cause difficulty when the user captures his or her own face and sends it to the other party during a video call or the like, and the second camera 121b has a relatively large number of pixels since the user often captures a general object that is not sent immediately.

The first and the second camera 121*a*, 121*b* may be provided in the terminal body in a rotatable and pop-upable manner.

Furthermore, a flash 123 and a mirror 124 may be additionally disposed adjacent to the second camera 121*b*. The flash 123 illuminates light toward an object when capturing the object with the second camera 121*b*. The mirror 124 allows the user to look at his or her own face, or the like, in a reflected way when capturing himself or herself (in a self-portrait mode) by using the second camera 121*b*.

A second audio output unit 153*b* may be additionally disposed at a rear surface of the terminal body. The second audio output unit 153*b* together with the first audio output unit 153*a* (e.g., in FIG. 5A) can implement a stereo function, and may be also used to implement a speaker phone mode during a phone call.

An antenna for receiving broadcast signals may be additionally disposed at a lateral surface of the terminal body in addition to an antenna for making a phone call or the like. The antenna constituting part of the broadcast receiving module 111 (e.g., in FIG. 1) may be provided in the terminal body in a retractable manner.

A power supply unit 190 (e.g., in FIG. 1) for supplying power to the mobile terminal 100 may be mounted on the terminal body. The power supply unit 190 may be incorporated into the terminal body, or may include a battery 191 configured in a detachable manner on the outside of the terminal body. According to the drawing, it is illustrated that the battery cover 103 is combined with the rear case 102 to cover the battery 191, thereby restricting the battery 191 from being released and protecting the battery 191 from external shocks and foreign substances.

Vehicle Control Apparatus

The vehicle control apparatus disclosed in the present specification is described below referring to FIGS. 6A to 8C.

Figure 6A:
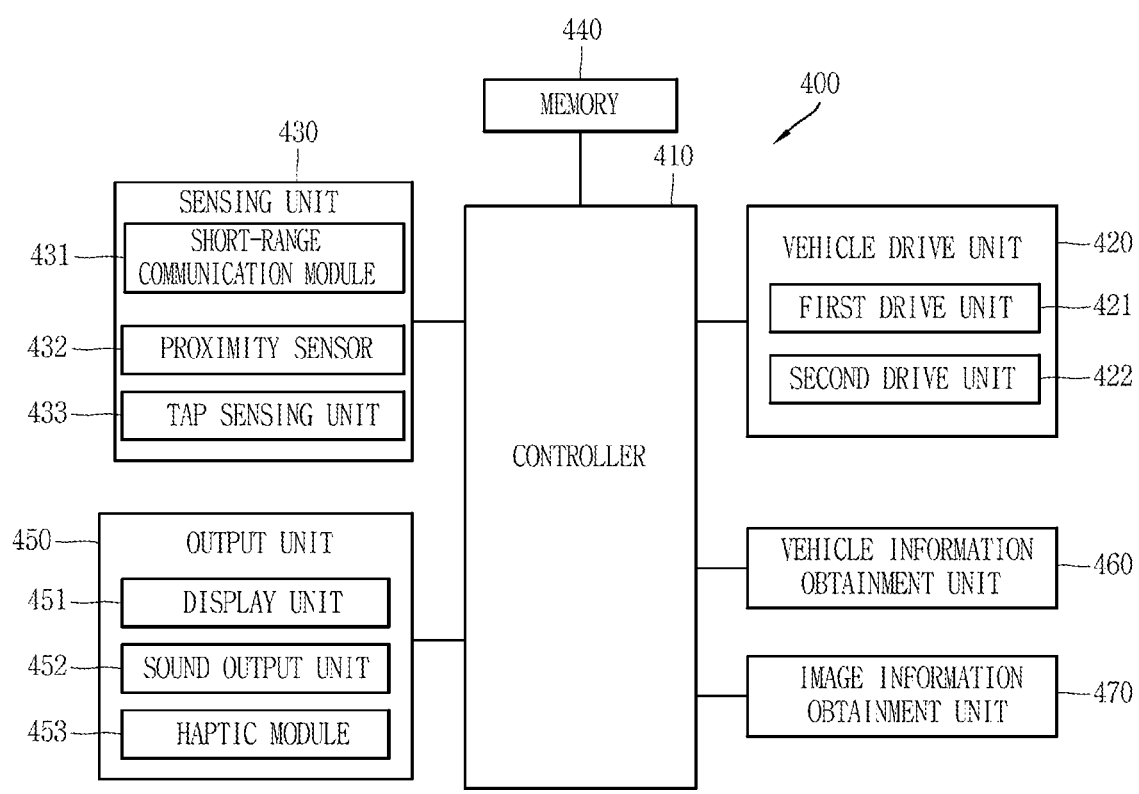
FIG. 6A is a block diagram illustrating an example of a vehicle control apparatus.

FIG. 6A is a block diagram of an example of a vehicle control apparatus according to some implementations.

Figure 6B:
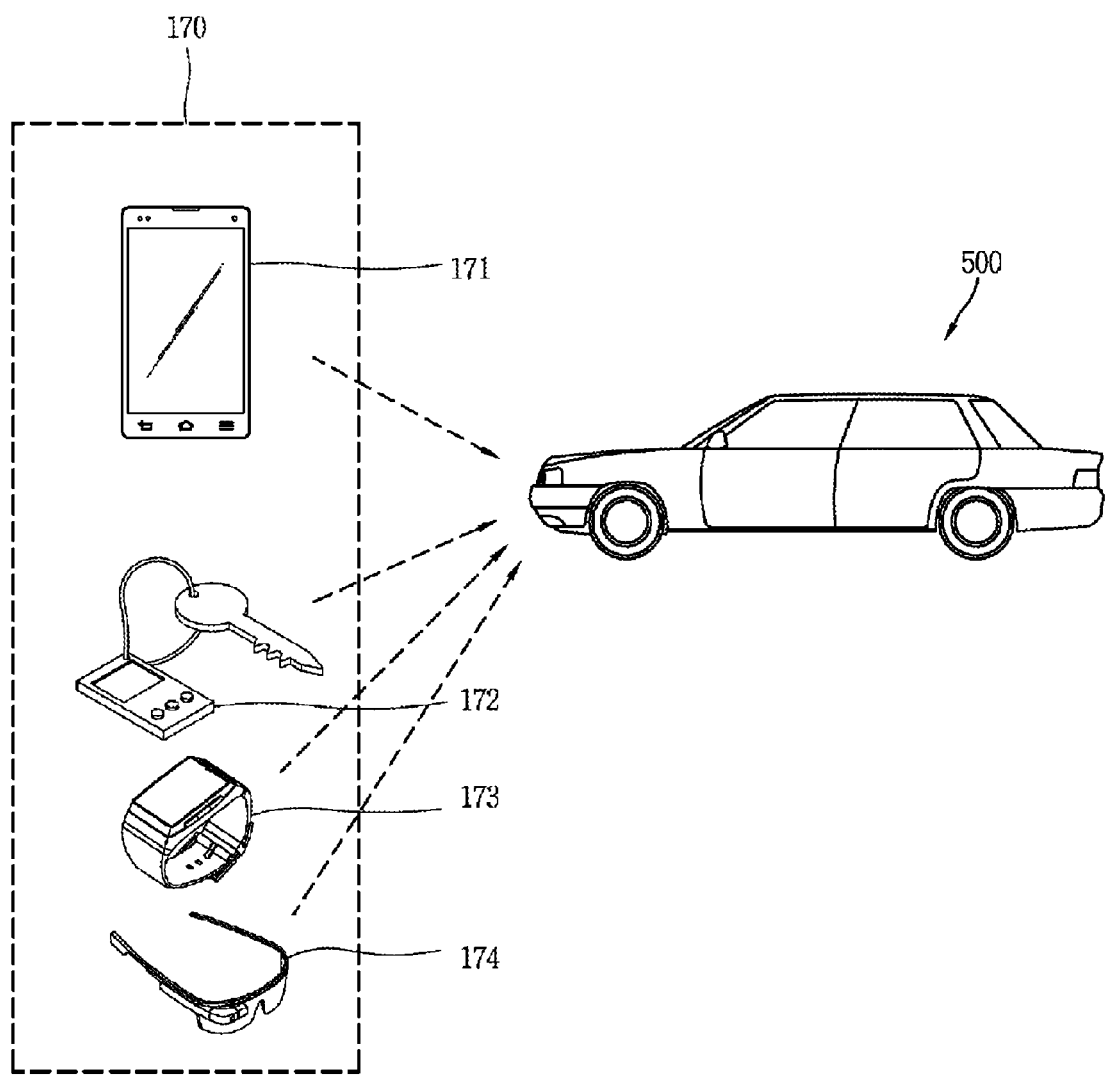
FIG. 6B is a diagram illustrating an example of an external device that is connected to the vehicle control apparatus.

FIG. 6B is a diagram illustrating one example of an external device that is connected to the vehicle control apparatus according to some implementations.

FIG. 6A is a block diagram for describing the vehicle control apparatus, disclosed in the present specification, according to some implementations. FIG. 6B is a diagram illustrating an example of the external device that is capable of being connected to the vehicle control apparatus, disclosed in the present specification, according to some implementations.

First, as illustrated in FIG. 6A, a vehicle control apparatus 400, disclosed in the present specification, according to some implementations, is configured to include a controller 410, a sensing unit 430 connected to the controller 410, a vehicle drive unit 420, and a memory 440. The vehicle control apparatus 400 may further include an output unit 450. Then, the vehicle control apparatus 400 is formed in a body of a vehicle that is configured to include an external frame that makes up an external appearance of the vehicle, a window, and an internal frame which is formed in such a manner that the user rides in. At this point, the constituent elements illustrated in FIG. 6A are not essential in realizing the vehicle control apparatus 400 according to some implementations, and thus the vehicle control apparatus 400 described in the present specification may include one or more constituent elements in addition to the constituent elements described above and may omit one or more constituent elements.

The sensing unit 430 is typically implemented using one or more sensors configured to sense internal information of the vehicle control apparatus 400, the surrounding environment of the vehicle control apparatus 400, user information, and the like. For example, the sensing unit 430 is shown having a proximity sensor 432 and an illumination sensor. If desired, the sensing unit 430 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor, a microphone 122, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The vehicle control apparatus 400 may be configured to utilize information obtained from sensing unit 430, and in particular, information obtained from one or more sensors of the sensing unit 430, and combinations thereof.

The sensing unit 430 may further include a short-range communication module 431. The short-range communication module 431 for short-range communication may support short-range communication using at least one of Bluetooth™, Radio Frequency Identification (RFID), Infrared Data Association (IrDA), Ultra Wideband (UWB), ZigBee, Near Field Communication (NFC), Wireless-Fidelity (Wi-Fi), Wi-Fi Direct, Wireless Universal Serial Bus (Wireless USB). The short-range communication module 431 may support wireless communication between the vehicle control apparatus 400 and an external device 170 (refer to FIG. 6B) through wireless area networks.

The external device may be the mobile terminal 100 described above. Particularly, the external device may be in the form of the wearable device 200 or 200', which is one type of the mobile terminal described above.

The vehicle drive unit 420 cancels a locked state of the vehicle or switches the vehicle to the locked state. At this point, the locked state of the vehicle is a state where one or more of or all of the functions of the vehicle are limited, the vehicle does not start, or a door of the vehicle does not open. As opposed to the locked state, the canceling of the locked state makes the vehicle return to a state where, at least one among a driver seat, a front passenger seat, rear passenger seats, and a trunk can open, functions of the vehicle can be performed, that is, the vehicle can start, or various functions, such as a navigation function and a ventilation function, can be performed.

In addition, the vehicle drive unit 420 changes various settings and enables a function to be automatically performed. For example, the vehicle drive unit 420 controls constituent elements of the vehicle under the control of the controller 410, for example, controls the extent to which a window of the front driver seat or the front passenger seat is opened or controls an angle of a rear view mirror. The vehicle drive unit 420 adjusts a height or a horizontal position (for example, a distance between the seats) of at least one among the front driver seat or the front passenger seat and the rear seats. The vehicle drive unit 420 may set a steering wheel in the driver seat, for example, may set a height of the steering wheel and a sensitivity of the steering wheel and the like under the control of the controller 410. In addition, under the control of the controller 410, the vehicle drive unit 420 may enable a gear to operate in an automatic transmission or in a manual transmission, and in a case of a hybrid vehicle, may enable any one, among a mode of operation of a combustion engine and a mode of operation of an electric motor mode, to be preferentially selected.

In addition, under the control of the controller 410, the vehicle drive unit 420 may change not only a hardware setting state of the vehicle, but also a software setting state of the vehicle. For example, under the control of the controller 410, the vehicle drive unit 420 may enable a predetermined music play list to be displayed or may enable one music item on the predetermined music play list to be automatically reproduced. In addition, the vehicle drive unit 420 may automatically set a predetermined specific destination point and may enable a path to the specific destination point to be automatically displayed though a navigation apparatus. In addition, under the control of the controller 410, the vehicle drive unit 420 may enable a distance from a preceding or following vehicle or a speed of the vehicle to be automatically set at the time of cruise driving of the vehicle.

To do this, the vehicle drive unit 420 is configured to include different sub-drive units, and the sub-drive units change hardware or software setting states of the vehicle, respectively. The sub-drive unit that changes the hardware setting state of the vehicle is referred to as a first drive unit 421, and the sub-drive unit that changes the software setting state of the vehicle is referred to as a second drive unit 422.

At this point, in order to change the hardware setting of the vehicle, the first drive unit 421 is configured to include different constituent elements that change the external frame or the internal frame of the vehicle. For example, the first drive unit 421 may further include a hardware drive unit for adjusting a height of the seat or an angle of the back of the seat, and may further include a unit for adjusting the height of the steering wheel, which is configured to include an elastic member or a pressure member, such as a coil or a spring for elevating or lowering the height of the steering wheel.

In some implementations, the second drive unit 422 is realized as at least one or more application programs or applications. For example, the second drive unit 422 is realized as being in the form that includes any one among application programs for driving the navigation apparatus or an application program for reproducing already-stored medium data (for example, MP3) and the like. These application programs or applications may be those for one among types of drive control of the vehicle.

The output unit 450 is for generating an output associated with a sense of sight, an auditory sense, or a tactual sense, and is configured to include at least one among a display unit 451, a sound output unit 452, a haptic module 453, and an optical output unit 454. The touch sensor is configured to be layered into, or is integrally formed into the display unit 451 on which various pieces of image information is displayed, or is integrally formed into the display unit 451, thereby realizing a touch screen. The touch screen functions as a user input unit 423 that provides an input interface between the vehicle control apparatus 400 and the user, and provides an output interface between the vehicle control apparatus 400 and the user.

The touch screen is realized as on various portions of the vehicle. For example, the touch screen is realized on entire windshield glass in the vehicle or one portion of the windshield glass, and may be realized anywhere on the external surface (surface exposed to outside of the vehicle) or an internal surface (a surface that faces the inside of the vehicle). In addition, the touch screen may be realized on an external or internal surface of a side window in the driver seat, a side window in the front passenger seat, or a window in the rear seat of the vehicle. The touch screen may be realized on a rear view mirror or a sunroof of the vehicle.

In addition, the touch screen may be realized not only on glass such as the window or sunroof of the vehicle, but also on the external or internal frame of the vehicle. For example, the touch screen may be realized on a surface of the external frame of the vehicle, that is, the external frame between the windshield and the window, or between the windows, such as an A-pillar, a B-pillar, or a C-pillar. In addition, the touch screen may be realized on at least one portion (for example, one portion in the vicinity of a door knob of a vehicle door) of the external surface of the vehicle door. The touch screen may be formed also on a surface of a cover of a gear box within the vehicle or on one portion of a cover of a console box. In addition, two or more of the touch screens may be formed on at least one or more different portions of the vehicle.

Data available to various functions of the vehicle control apparatus 400 is stored in the memory 440. Multiple application programs or applications that run on the vehicle control apparatus 400, data and commands for the vehicle control apparatus 400 are stored in the memory 440. At least one or more of these application programs are downloaded from an external server over a wireless communication network. In addition, for basic functions (for example, a vehicle starting function, a navigation function, and vehicle locking and unlocking functions), at least one or more of these application programs are pre-installed on the vehicle control apparatus 400 before shipping. In some implementations, the application program is stored in the memory 440 and is installed on the vehicle control apparatus 400. The controller 410 runs the application program in order that the application program performs operation (or a function) of the vehicle control apparatus.

According to some implementations, the application program may be a navigation program that performs a navigation function.

Pieces of information relating to at least one or more users are stored in the memory 440. At this point, the information relating to the user is authentication information on the user and information relating to various setting conditions of the vehicle that are set by the user himself/herself or are set properly based on the biological information on the user. The information relating to the user is, for example, setting information relating to indoor temperature or humidity in the vehicle, which is set by the user himself/herself, setting information that depends on a driving habit of the user, or the like. In addition, the information relating to the user may be a record of driving paths along which the user drove. In addition, the authentication information may be information on a password or a pattern that is predetermined by the user, or may be information that is based on the biological information on the user, such as recognition information on user's fingerprints or irises. In addition, the authentication information may be information relating to a user's gesture.

According to some implementations, the biological information on the user is obtained by the mobile terminal 100 (or the wearable device 200 or 200').

In this case, the wearable device may further include a communication unit that performs communication with the vehicle control apparatus which is installed in the vehicle and a biological information obtainment unit that obtains the biological information on the user from the specific body portion (for example, a wrist portion).

At this point, the communication unit transmits the obtained biological information on the user to the vehicle control apparatus 400, and the biological information on the user is stored in the memory 440.

The biological information is at least one piece of information, among pieces of information on a user's heart rate, user's body fat, user's blood pressure, user's blood sugar, user's lineaments, user's fingerprints, a user's brain wave, and user's irises.

In addition, a program for operation of the controller 410 is stored in the memory 440, pieces of data, (for example, user authentication information, or driving environment setting information) that are input or output may be temporarily stored in the memory 440. Pieces of data on various patterns of vibration and sound that are output when a touch input is applied to the touch screen are stored in the memory 440.

The memories 440 include storage media, such as a flash memory, a hard disk, a solid state disk (SDD), a silicon disk drive (SDD), a multimedia card micro type, a card memory (for example, an SD, a XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The vehicle control apparatus 400 may operate in association with a web storage apparatus that, like the memory 440, performs a storage function over the Internet.

In some implementations, the controller 410 normally controls entire operation of the vehicle control apparatus 400 in addition to the operation associated with the application programs described above. The controller 410 processes the signal, the data, the information, and the like that are input or output through the constituent elements described above, or controls driving of the vehicle by running the application program that is stored in the memory 440. In addition, the controller 410 controls at least one or more, among the constituent elements that are described referring FIG. 1A, in order to run the application program stored in the memory 440. Furthermore, the controller 410 controls the constituent elements that are included in the vehicle control apparatus 400, in combination of at least two or more of them, in order to run the application program.

In some implementations, the user inputs the authentication information into the controller 410, and the controller 410 determines whether or not the user is an authenticated user, based on the authentication information. The authentication information is recognition information on the user's finger or on a predetermined pattern. In addition, the authentication information is recognition information on user's irises, or information relating to a user's specific gesture. For example, pattern recognition information or finger recognition information is input, as the authentication information, into the controller 410. The pattern recognition information is on multiple-times tapping (for example, multiple taps or multiple knocks) that are applied by the user to one portion of the external or internal surface of the vehicle. The finger recognition information is input through one portion of the external or internal surface of the vehicle, or through a touch screen region that is formed on the window and the window shield glass and the like in the driver seat or the passenger seat. In addition, the controller 410 may recognize the user's gesture that is made inside of or outside of the vehicle, or may recognize the iris information on the user, using the photo sensor or the camera that is provided in the sensing unit 430.

Then, the controller 410 cancels the locked state of the vehicle when the user is an authenticated user. Then, the vehicle control apparatus 400 enables the user to open the door of the vehicle, the trunk, and the like without having to use the key to them. In addition, the controller 410 may make the vehicle start using predetermined authentication information on the user. In addition, the controller 410 may switch the state of the vehicle to the locked state. That is, based on the selection by the authenticated user, the controller 410 may maintain the locked state of the vehicle until the authentication information on the authenticated user is input again. In some implementations, when the authentication information on the user is input from outside of the vehicle in the state where the vehicle is unlocked, based on this, the controller 410 switches the state of the vehicle to the locked state. Then, when the same authentication information is input again in a state where the vehicle is switched to the locked state, the vehicle may be switched back to the unlocked state.

The touch screen is formed on one portion of the vehicle in order that the authentication information on the user is input into the controller 410. Information on user's fingers or information on the user-set pattern is input into the controller 410 through the formed touch screen. Alternatively, a predetermined password may be input into the controller 410. To do this, the controller 410 performs pattern recognition processing that recognizes writing input or picture-drawing input that is applied to the touch screen, as text or an image, respectively. Furthermore, the controller 410 controls one among the constituent elements described above, or a combination of two or more of them in order to realize the vehicle control apparatus 400 according to some implementations, which are described below.

In addition, the controller 410 may display various pieces of image information on the touch screen that is formed on one portion of the vehicle. For example, the controller 410 may display a finger input region for authenticating the user or graphic objects for applying a pattern input on the touch screen, and may display a result of the user authentication, information relating to the currently-authenticated user, or the like.

Then, when the user is an authenticated user, the controller 410 changes the setting state of the vehicle using the user-related information that corresponds to the corresponding user. For example, by controlling the first drive unit 421, the controller 410 adjusts the height of the driver seat or the like, the angle of the back of the seat, or the like and may adjust the indoor temperature or humidity in the vehicle, based on the authenticated information on the user. In addition, based on information that corresponds to the authenticated user, the controller 410 adjusts the extent to which the window of the driver seat and the front passenger seat are opened or controls the angle of the rear view mirror and the like. The controller 410 may adjust the height of the steering wheel and the like.

The controller 410 may change a vehicle operation mode as well according to the authenticated user. For example, the controller 410 may switch a power steering wheel operation mode to a specific mode (for example, a normal mode or a sports mode) according to a preference of the authenticated user. In addition, the controller 410 may switch a gear transmission mode to a manual transmission mode or an automatic transmission mode according to a preference of the authenticated user.

In addition, the controller 410 may change not only such hardware settings, but also software settings. For example, if the authenticated user rides in the vehicle, the controller 410 automatically selects his/her favorite music item or a list containing a music item that he/she previously listens to. In addition, the controller 410 may automatically select a channel of a radio broadcasting system that the authenticated user frequently tunes in and listens to.

In addition, the controller 410 may change various settings of the vehicle, based on the time at which the authenticated user rides in the vehicle. For example, based on the time at which the user is authenticated and on the record of the authenticated driver's driving, the controller 410 searches for a destination point where the authenticated user frequently goes at the corresponding time. That is, if the user has a habit of regularly going "home" after work at between 8:00 pm and 9:00 pm, when the user rides in the vehicle at between 8:00 pm to 9:00 pm, the controller 410 may automatically set the destination point to "home" and display the corresponding path on a display unit of the navigation apparatus, based on the record of the driving.

In this manner, the controller 410 of the vehicle control apparatus 400 according to some implementations enables the user to control the vehicle using the authentication information. As a result, the user can ride in the vehicle and control the vehicle in an easier and more convenient manner. When the user is authenticated, the controller 410 of the vehicle control apparatus 400 according to some implementations adjusts various driving environment settings of the vehicle as well, based on the fact that the user is authenticated, thereby automatically providing his/her favorite driving environment.

In addition, whether or not the user rides in the vehicle, the controller 410 may change the hardware or software settings of the vehicle in a convenient manner, based on the user's selection. For example, the controller 410 may change at least one hardware or software setting, based on the multiple-times tapping on the inside of the vehicle, for example, the console box, the gear box, or the windows in the driver seat or the front passenger seat. As one example, if the user applies the tapping multiple times to the steering wheel of the vehicle, the controller 410 recognizes this and thus may adjust the height of the steering wheel or may change the power steering wheel operation mode from one mode to another.

In some implementations, the controller 410 changes the hardware or software setting state, based not only on the multiple taps, but also on the user's gesture. For example, the controller 410 makes it possible for a camera, a photo sensor, a laser sensor, or an infrared sensor to sense movements of the driver or the passenger who rides in the vehicle. Then, based on the movements of the driver and the passenger, the controller 410 may perform a specific function and adjust a currently-set state. As one example, if the passenger sitting on the front passenger seat make a hand-lowering gesture toward the window in the front passenger seat, the extent to which the window in the front passenger seat is opened is adjusted based on the passenger's gesture. In addition, if a specific gesture (for example, a fingers-flicking gesture or a hands-clapping gesture) is sensed, the controller 410 may reproduce predetermined specific music data, based on the driver's or passenger's gesture.

In some implementations, at least one or more among the constituent elements described above, operate in cooperation with one another to realize operation or control of the vehicle control apparatus 400, or a method of controlling the vehicle control apparatus 400, which are described above, according to various implementations. In addition, the operation or the control of the vehicle control apparatus 400, or the method of controlling the vehicle control apparatus 400 is realized on the vehicle control apparatus 400 by running at least one application program that is stored in the memory 440.

The constituent elements enumerated above are described in more detail below referring to FIG. 6A, before describing the vehicle control apparatus 400 according to the various implementations.

The sensing unit 430 senses at least one among information on the inside of the vehicle control apparatus, information on an surrounding environment of the vehicle control apparatus, and information on the user, and generates a sensing signal corresponding to the sensed information. Based on the sensing signal, the controller 410 controls driving of or operation of the vehicle control apparatus 400, or performs data processing, a function, or an operation associated with the application program that is stored on the vehicle control apparatus 400. Typical sensors among various sensors that can be included in the sensing unit 430 are described in more detail.

The proximity sensor 432 may include a sensor to sense presence or absence of an object approaching a surface, or an object located near a surface, by using an electromagnetic field, infrared rays, or the like without a mechanical contact. The proximity sensor 432 may be arranged at an inner region of the mobile terminal covered by the touch screen, or near the touch screen.

The proximity sensor 432, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 432 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 432 senses a proximity touch and a proximity touch pattern (for example, a proximity touch distance, a proximity touch direction, a proximity touch speed, proximity touch time, a proximity touch position, a proximity touch movement state, and the like). In some implementations, the controller 410 processes data (or information) that corresponds to the proximity touch operation and the proximity touch pattern that are sensed through the proximity sensor 432, and further outputs visual information that corresponds to the processed data, on the touch screen. Furthermore, the controller 410 may control the vehicle control apparatus 400 in such a manner that different operations are performed or different pieces of data (or different pieces of information) are processed depending on whether the touch applied to the same point on the touch screen is a proximity touch or a contact touch.

A touch sensor can sense a touch applied to the touch screen, such as the display unit 451, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 451, or convert capacitance occurring at a specific part of the display unit 451, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 410. Accordingly, the controller 410 may sense which region of the display unit 451 has been touched. In some implementations, the touch controller may be a component separate from the controller 410, the controller 410, and combinations thereof.

In some implementations, the controller 410 may execute the same or different controls according to a type of touch object that touches the touch screen or a touch key provided in addition to the touch screen. Whether to execute the same or different control according to the object which provides a touch input may be decided based on a current operating state of the vehicle control apparatus 400 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 410, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The sensing unit 430 typically includes at least one a camera sensor (CCD, CMOS etc.), a photo sensor (or image sensors), and a laser sensor.

Implementing a camera 421 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

As described above, various pieces of image information relating to inputting of the authentication information on the user are displayed on the display unit 451. For example, a graphic object that indicates a region for inputting a user's fingerprint or a graphic object for inputting the pattern information are displayed on the display unit 451 that is formed, as the touch screen, on one portion of the vehicle. In addition, if user authentication is ended, a result of the user authentication and information relating to the currently-authenticated user may be displayed on the display unit 451. These pieces of image information are displayed on at least one portion of the windshield glass of the vehicle, the window in the front passenger seat, or the like. To do this, at least one portion of the window of the vehicle or at least one portion of the windshield glass of the vehicle that is equipped with the vehicle control apparatus 400 according to some implementations is designed in such a manner that the touch input by the user is sensed.

In addition, the display unit 451 is formed on not only the external surface of the windshield glasses and of the window, but also on the internal surface. Then, information that is processed in the vehicle control apparatus 400 may be displayed (or output) on the display unit 451 that is formed on the internal surface.

For example, screen information that is displayed on the display unit 451 that is formed on the internal surface is execution screen information on an application program that is run on the vehicle control apparatus 400, or information on a user interface (UI) and a graphic user interface (GUI) that depend on the execution screen information.

In addition, the display unit 451 may be realized as included in the sensing unit 430. In this case, a result of the sensing by the sensing unit 430, and a result of matching the user authentication information or at least one portion (for example, a name of the user and like) of the authentication information inherent to the user may be displayed on the display unit 451.

Audio data that is stored in the memory 440 is output through the sound output unit 452. A sound signal associated with a function (for example, a user authentication confirmation sound and a user authentication guidance sound) that is performed in the vehicle control apparatus 400 may be output through the sound output unit 452. The sound output unit 452 is configured to include a speaker, a buzzer, and the like.

In some implementations, the output unit 450 of the vehicle control apparatus 400, disclosed in the present specification, according to some implementations, is configured to include the haptic module 453. The haptic module 453 generates various haptic effects that the user can feel. A typical example of the haptic effect that is generated by the haptic module 453 is vibration. If it is sensed that the touch input by the user is applied to the touch screen realized on the external frame of the internal frame of the vehicle, the widow in the form of glass, or the like, the controller 410 outputs haptic information using the haptic module 453. Accordingly, using the haptic information, the user can confirm whether he/she properly input the authentication information.

The strength, pattern and the like of the vibration generated by the haptic module 453 can be controlled by user selection or setting by the controller. For example, the haptic module 453 may output different vibrations in a combining manner or a sequential manner.

Besides vibration, the haptic module 453 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 453 can also be implemented to allow the user to feel a tactile effect through a muscle sensation such as the user's fingers or arm, as well as transferring the tactile effect through direct contact. Two or more haptic modules 453 may be provided according to the particular configuration of the vehicle control apparatus 400.

Various implementations to be explained later may be implemented in a computer or a computer-readable recording medium, by software, hardware, or a combination thereof.

In some implementations, the sensing unit 430 of the vehicle control apparatus 400, disclosed in the present specification, according to some implementations may further include a main body that is configured to be mounted on the body and to come into contact with one portion of a user's body, and a tap sensing unit 433 for sensing a tap on the main body or a tap gesture. At this point, the tap that is sensed in the tap sensing unit 433 of the vehicle control apparatus 400 is a means for inputting the authentication information on the user. In addition, if the user rides in the vehicle, the tap is used as a means for controlling various functions of the vehicle control apparatus 400. Then, the tap is construed to mean a motion of lightly hitting the main body of the vehicle control apparatus 400 or an object, with a tapping tool such as a finger, or a motion of lightly bringing the tapping tool into contact with the main body of the vehicle control apparatus 400 or the object. At this point, the main body of the sensing unit 430 is formed on the body of the vehicle that is configured to include the external frame and the internal frame of the vehicle and the window or the windshield glass.

In some implementations, the tapping tool with which the tap is applied is a thing that applies an external force to the main body of the vehicle control apparatus 400 or the object, such as a finger, a stylus pen, a pen, a pointer, and a fist. In some implementations, the tipping tool is not necessarily limited to the thing that can be applied to the vehicle control apparatus 400 according to some implementations, and any type of thing may be possible as long as it can apply the external force to the main body of the vehicle control apparatus 400 or the object.

In some implementations, the objects to which the tap gesture is applied is at least one among the main body of the vehicle control apparatus 400 and the object that is placed on and on the vehicle control apparatus 400.

In some implementations, the tap or the tap gesture is sensed by at least one among an acceleration sensor and a touch sensor that are included in the tap sensing unit 433. At this point, the acceleration sensor is a sensor that is capable of measuring dynamic forces, such as acceleration, vibration, and impact, which are applied to the main body of the vehicle control apparatus 400.

That is, the acceleration sensor senses vibration (or a movement) of the main body of the vehicle control apparatus 400, which occurs due to the tap gesture, and thus senses whether the tap is applied to the object. Therefore, the acceleration sensor senses the tap on the main body of the vehicle control apparatus 400 or senses that an object that is positioned close to the main body of the vehicle control apparatus 400 to such an extent that it can be sensed whether the movement or the vibration occurs in the main body of the vehicle control apparatus 400 is tapped on.

In this manner, as long as the sensing of the movement or the vibration of the main body of the vehicle control apparatus 400 is possible, the acceleration sensor senses not only the application of the tap to the main body of the vehicle control apparatus 400, but also senses the application of the tap to points other than the main body.

In the vehicle control apparatus 400 according to some implementations, in order to sense the tap on the vehicle control apparatus, one among the acceleration sensor and the touch sensor is used, the acceleration sensor and the touch sensor are sequentially used, or the acceleration sensor and the touch sensor are used at the same time. In some implementations, a mode in which the acceleration sensor is used to sense the tap is referred to as a first mode, a mode in which the touch sensor is used to sense the tap is referred to as a second mode, and a mode in which the acceleration sensor and the touch sensor are all utilized (at the same time or sequentially) to sense the tap is referred to as a third mode or a hybrid mode.

In some implementations, if the tap is sensed through the touch sensor, it is possible to more accurately recognize a position at which the tap is sensed.

In some implementations, in the vehicle control apparatus 400 according to some implementations, in order to sense the tap through the acceleration sensor or the touch sensor, the display unit 451 of the vehicle control apparatus 400 also operates in an inactivated state in a specific mode in which a minimum amount of current or electric power is consumed. The specific mode is referred to as a doze mode.

For example, in the dose mode, a light-emitting element for outputting a screen is turned off and the touch sensor is turned on in the display unit 451 in a touch screen structure in which the touch sensor is layered into the display unit 451. In addition, the dose mode is a mode in which the display unit 451 is turned off and the acceleration sensor is turned on. In addition, the dose mode is a mode in which the display unit 451 is turned off and the touch sensor and the acceleration sensor are all turned on.

Therefore, in the dose mode, that is, in a state where the display unit 451 is turned off (in a state where the display unit 451 is inactivated), if the user applies the tap to at least one point on the touch screen that is formed on one portion of the vehicle, or to a specific point on the main body of the vehicle control apparatus 400, it is sensed that the tap is applied from the user, through at least one among the touch sensor or the acceleration sensor that is turned on.

In addition, in order to distinguish between a tap as a means for inputting the authentication information on the user or a tap as a means for controlling a function of the vehicle control apparatus 400, and a simple collision of an outside arbitrary object with the touch screen, if the tap is applied two or more times within a reference time to the touch screen formed on one portion of the vehicle, it is determined that the "tap" is sensed for inputting the authentication information on the user and controlling the vehicle control apparatus 400. For example, if it is determined that as a result of the sensing by the tap sensing unit 433, the tap is applied one time to the touch screen formed on one portion of the vehicle, the controller 410 may recognize that the outside arbitrary object or an human body collides with the touch screen, without recognizing that the one-time tap is for inputting the authentication information on the user.

Therefore, if the tap sensing unit 433 senses that the tap is applied at least two or more times (or multiple times) consecutively within the reference time, it is determined that the "tap" as the means for inputting the authentication information on the user or as the mean of controlling the function of the vehicle control apparatus 400 is sensed.

That is, the tap gestures mean that the tap gesture is to be sensed at least two or more times consecutively within the reference time. Therefore, the sensing of the "tap" hereinafter means that it is sensed that a user's finger or an object such as a touch pen is lightly hit substantially multiple times on the main body of the main body of the vehicle control apparatus 400.

Furthermore, the controller 410 may make it possible not only to sense the tap within the reference time, but also to determine whether the taps applied using user's different fingers are sensed or the taps applied using one finger of the user are sensed. For example, if it is sensed that the taps are applied to one predetermined portion of the vehicle, that is, one portion of the window of the vehicle or one portion of the window shield glass, an A-pillar, a B-pillar, a C-pillar, a sunroof, one portion of a vehicle door, or a console box or a gear box in the vehicle, the controller 410 makes it possible to sense whether the taps are applied using one finger or using different fingers, using fingerprints that are sensed from the portion to which the taps are applied. In addition, the controller 410 recognizes a position on the display unit 451, at which the taps are sensed, or acceleration that is generated due to the taps, through at least one, among the touch sensor and the acceleration sensor that are provided in the tap sensing unit 433. Thus, the controller 410 makes it possible to sense whether the taps are applied using one finger or using different fingers.

Furthermore, considering additionally an angle at which the tap is applied and a distance between points to which the tap is applied or a direction in which the fingerprint is recognized, the controller 410 determines whether the taps are applied using one finger or using both hands or at least two fingers.

In some implementations, the taps mean multiple-times tapping that are sensed consecutively within the reference time. At this point, the reference time is a very short time, for example, a time in a range of 300 ms to 2 s.

To do this, when the tap sensing unit 433 senses that the main body of the vehicle control apparatus 400 is tapped on, the tap sensing unit 433 senses whether the next tapping is applied consecutively within the reference time after the first tapping is sensed. Then, if the next tapping is sensed within the reference time, the tap sensing unit 433 or the controller 410 determines that the tap is sensed for inputting the authentication information on the user or for controlling a specific function of the vehicle control apparatus 400 according to some implementations. In this manner, if a second tap is sensed within a predetermined time after a first tap is sensed, the controller 410 recognizes the first and second taps as "effective taps." Thus, the controller distinguishes between the tap that is applied to input the authentication information on the user or to control the vehicle control apparatus 400 and the collision of an object with the inside or outside of the vehicle, which occurs unintentionally or due to a user mistake.

There are various method of recognizing the "effective tap." For example, when it is sensed that the second tap is applied a second reference number of times or greater to the main body within a predetermined time after sensing the first tap that is applied a first reference number of times or greater, the controller 410 may recognizes the first and second taps as the "effective taps." At this point, the first reference number of times and the second reference number of times may be the same or be different. For example, the first reference number of times may be 1, and the second reference number of times may be 2. As another example, the first reference number of times and the second reference number of times may be all 1.

In addition, if the tap is applied to within a "predetermined region," it is determined that the "taps" are sensed.

That is, when it is determined that the main body of the vehicle control apparatus 400 is first tapped on, the controller 410 calculates a predetermined region from a point at which the tapping is first sensed. Then, if the tapping is consecutively sensed the first or second reference number of times or greater at the "predetermined region" within the reference time after the first tapping is sensed, the controller 410 determines that the first tap or the second tap is applied.

In some implementations, the reference time and the predetermined region that are described above can be variably modified according to some implementations.

In some implementations, the first tap and the second tap may be sensed as a separate tap according to not only the reference time and the predetermined region, but also a position at which each tap is sensed. That is, if the second tap is sensed in a position that is a predetermined distance or above away from the position in which the first tap is sensed, the controller 410 determines that the first tap and the second tap are applied. Then, if the first tap and the second tap are recognized based the position in which the tap is sensed, the first tap and the second tap may both be sensed.

In addition, if the first tap and the second tap are configured from multiple touches, that is, from multiple-times tapping, the multiple touches that make up each of the first tap and the second tap are both sensed. For example, if the first touch that makes up the first tap is sensed and additionally the first touch that makes up the second tap is sensed in a position that is a predetermined distance or above from a position in which the first touch that makes up the first tap is also sensed, the controller 410 makes it possible to enable the first touch that makes up each of the first tap and the second tap. Then, the controller 410 makes it possible to enable an additional touch input, which is sensed in each position. If the touch is sensed the first reference number of times or greater or the second reference number of times or greater, the controller 410 determines that the first tap and the second tap are applied.

In some implementations, when the tap sensing unit 433 senses multiple times that the tap is applied to the main body of the vehicle control apparatus 400, the controller 410 controls not only the user authentication, but also at least one among functions that is executable on the vehicle control apparatus 400. At this point, the functions that is executable on the vehicle control apparatus 400 can include various types of functions executable or runnable on the vehicle control apparatus 400. At this point, one among the executable functions is a function of an application that is installed on the vehicle control apparatus 400. Then, "an arbitrary function is executed" means "an arbitrary application program is executed or is run on the vehicle control apparatus 400." For example, based on the user's multiple taps that are sensed in the console box, the controller 410 reproduces a music file or controls the navigation apparatus in such a manner that a path to a predetermined destination point is automatically set.

As another example, a function that is executable in the vehicle control apparatus 400 is a function that is necessary for basic driving of the vehicle control apparatus 400. For example, the function necessary for the basic driving is a function of turning on/off an air conditioner or a warm-air circulator provided in the vehicle, a function of starting the vehicle, a function of switching between the locked state and the unlocked state, or the like. In addition, the function necessary for the basic driving is a function of turning a cruise control function of the vehicle on or off.

In some implementations, the controller 410 forms a position for inputting the authentication information on the user, based on a point on the main body or the touch screen at which the tapping by the user is sensed. For example, the controller 410 forms a region for inputting the pattern information, or forms a region for inputting the biological information on the user, for example, the user's fingerprint, in such a manner that the point at which the tapping by the user is first applied serves the center of the region for inputting the pattern information or the biological information. In this case, even though the user applies the tap to a different point on the main body or the touch screen each time he/she applies the tap, the point at which the information on the user-set pattern or the biological information on the user varies each time the user applies the tap. Accordingly, the user can minimize exposure of the authentication information, and this is a safeguard against an illegal act, such as when the vehicle is stolen.

In some implementations, the user authentication information may be also input into the vehicle control apparatus 400 through an external device that is predetermined based on the user's selection. For example, the sensing unit 430 is connected to a predetermined external device outside of the vehicle using a short-range communication module 431. The authentication information on the user may be input into the sensing unit 430 through the short-range communication module 431 and may be authenticated by the controller 410.

The vehicle control apparatus 400 obtains vehicle information from the vehicle.

According to some implementations, the vehicle information is obtained through the sensing unit 430 described above.

According to some implementations, the vehicle control apparatus 400 separately is configured to include a vehicle information obtainment unit 460 that obtains the vehicle information.

At this point, the vehicle information is information relating to at least one, among an air conditioning function of the vehicle, a function of checking whether doors (including a hood, a trunk, a fuel intake) are opened or closed, a function of checking whether the windows are opened or closed, a function of checking whether the sunroof is opened or closed, a charged state of a battery of the vehicle, a place where the vehicle is parked, a function of the navigation apparatus provided in the vehicle, a function of checking whether the vehicle is stolen, an amount of fuel in the vehicle, and the like.

In addition, the vehicle information is configured to further include at least information relating to at least one, among current driving speed of the vehicle, current driving acceleration, mileage, the number of times that the vehicle gains sudden acceleration, the number of times that the vehicle stops suddenly.

To that end, the vehicle information obtainment unit 460 communicates with various sensors provided in the vehicle.

For example, the vehicle information obtainment unit 460 is installed in the vehicle, communicates with an acceleration sensor that measures acceleration of the vehicle, and gathers acceleration information on the vehicle.

In addition, for example, the vehicle information obtainment unit 460 performs communication with a black box provided in the vehicle, and obtains when a vehicle accident occurs. In this case, images associated with the vehicle accident are stored in the memory 440.

An image information obtainment unit 470 obtains image information on the user from an image obtainment apparatus 900.

Like a camera, the image obtainment apparatus 900 is a means for processing image frames for a static image and a moving image, which are captured by an image sensor, and obtains an image of the user.

The number of the image obtainment apparatuses 900 is 1 or greater. The image information obtainment unit 470 obtains the image information from various communication means.

FIG. 6B illustrates an example in which an external device that is predetermined in this manner is connected to the vehicle control apparatus according to some implementations.

Referring to FIG. 6B, the predetermined external device 170 is a mobile terminal, such a phone 171 or a smart key 172 that is carried by the user. In this case, the controller 410 recognizes a serial number of the external device 170. If the external device 170 is positioned within a given distance from the controller 410, the controller 410 automatically recognizes a specific user. Then, the controller 410 receives the authentication information that is input through the external device 170. The authentication information that is input from the external device 170 is transferred to the vehicle control apparatus 400 through a communication module provided in the external device 170 and through the short-range communication module 431 of the sensing unit 430.

In some implementations, the authentication information is the biological information on the user.

According to some implementations, the biological information is obtained by the mobile terminal 100 (or the wearable device 200 or 200').

At this point, the biological information is at least one piece of information, among pieces of information on a user's heart rate, user's body fat, user's blood pressure, user's blood sugar, user's lineaments, user's fingerprints, a user's brain wave, and user's irises.

For example, the authentication information is information on the user's heart rate or fingerprints, recognition information on the user's irises, information on the predetermined password of the user, or information on the pattern that is set by the user. In addition, the authentication information may be information relating to a user's specific gesture.

The authentication of the user is done based on multiple pieces of biological information or multiple pieces of authentication information.

For example, the user's heart rate and the user's gesture are checked, and then the authentication of the user is done.

To do this, the external device 170 may additionally have a configuration for the user inputting the authentication information, that is, a configuration for executing the same functions as those of at least one or more among the sensors provided in the sensing unit 430 of the vehicle control apparatus 400 according to some implementations or the same functions as those of additional sensors.

For example, the external device 170, such as the smart key 172 or the smart phone 171, may further include a sensing unit that is the same as, is similar to, corresponds to the touch screen into which the user can input the pattern information, or the tap sensing unit 433 which is provided in the sensing unit 430 of the vehicle control apparatus 400. In addition, the external device 170 may further include a fingerprint recognition unit for recognizing the user's fingerprints. In some implementations, the external device 170 may further include an inertial sensor, a gyro sensor, an acceleration sensor, or the like.

In addition, for example, a smart watch 173, which is a watch-type mobile terminal, is configured to include a sensor that obtains the user' heartbeat. In addition, smart glasses 174, which is an glasses-type mobile terminal, is configured to include an iris recognition camera for recognizing the user's irises.

In this case, the user can input the authentication information on him/her using at least one piece of information among the information on the fingerprints, the predetermined pattern information, and the iris recognition information. In addition, the user may input the authentication information on him/her into the external device 170 by making a specific gesture while wearing the external device 170. In this case, according to the user's gesture, the controller 410 of the external device 170 recognizes the user's gesture using information on a change in a position of the external device 170, that is, an acceleration measurement value, an amount of change in gravity, or a value that is obtained by measuring an amount of change in inertia. Thus, the controller 410 makes use of such information as the authentication information. In addition, the external device 170 may recognize that the position is changed, using an image of the user that is input through the camera and the like, and may measure a value that is changed.

In some implementations, if the authentication information is input in this manner, the controller 410 of the vehicle control apparatus 400 controls the driving of the vehicle using the authentication information that is input. For example, the controller 410 may recognize the current user according to the authentication information, and may cancel the locked state of the vehicle and set an internal environment of the vehicle that corresponds to the recognized user. In addition, if the locked state of the vehicle is canceled and the authentication information is input back in a state where the vehicle stops, the controller 410 may return the unlocked state of the vehicle to the locked state.

In some implementations, the vehicle may be controlled immediately using the authentication information on the user, which is input through the external device 170, but the controller 410 may request the user to go through an authentication process one more time. In this case, if the external device 170 is positioned within a given distance from the controller 410 or the authentication information is input through the external device 170, the controller 410 switches the state of the vehicle to a wake up state and prepares for starting the vehicle according to the authentication information that is input from the authenticated user. If in a state where the vehicle switches to the wake up state, the user inputs the authentication information one more time into a predetermined region (for example, the window in the driver seat or in the front passenger seat, the A- or B-, or C-pillar, or the like), the controller 410 authenticates the user according to the input and thus starts the vehicle.

In addition, the example is described above in which an authentication procedure is one more time is performed, but in some implementations, other authentication procedures may be performed without limitation. In addition, the example is described above in which if the authentication information on the user is input through external device 170, the multiple authentication procedures are performed, but in some implementations, the multiple authentication procedure may be applied also to a case where the user inputs the authentication information on him/her directly into the touch screen region that is formed on one portion of the vehicle.

Figure 7:
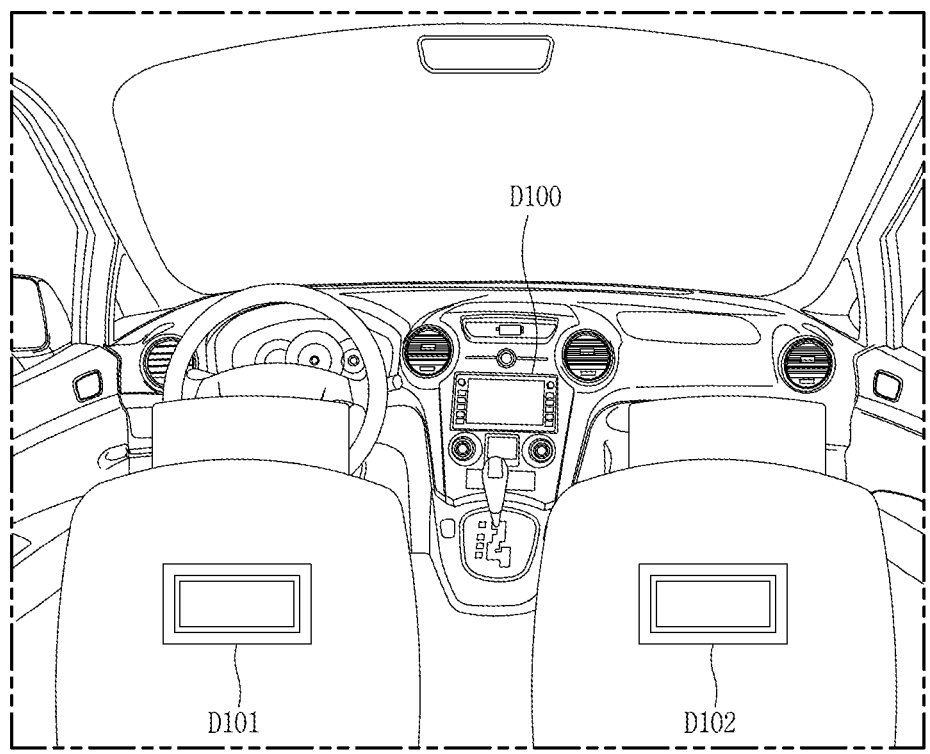
FIG. 7 is a diagram illustrating an example of a display unit of the vehicle control apparatus.

FIG. 7 is a diagram for describing the display unit of the vehicle control apparatus, disclosed in the present specification, according to some implementations.

FIG. 7 illustrates a case where the vehicle control apparatus 400 is realized as in the form of a head unit of the vehicle.

The vehicle control apparatus 400 is configured to include multiple display units D100 to D102.

For example, as illustrated in FIG. 7, the vehicle control apparatus 400 is configured to include one first display unit D100 in front of the driver seat, and two second display units D101 and D102 in front of the rear seats.

At this time, generally, the first display unit D100 is subject to regulations for safe driving.

Therefore, the first display unit D100 is subject to vehicle content display regulations, and content is displayed on the second display units D101 and D102 with any limitation.

Figure 8A:
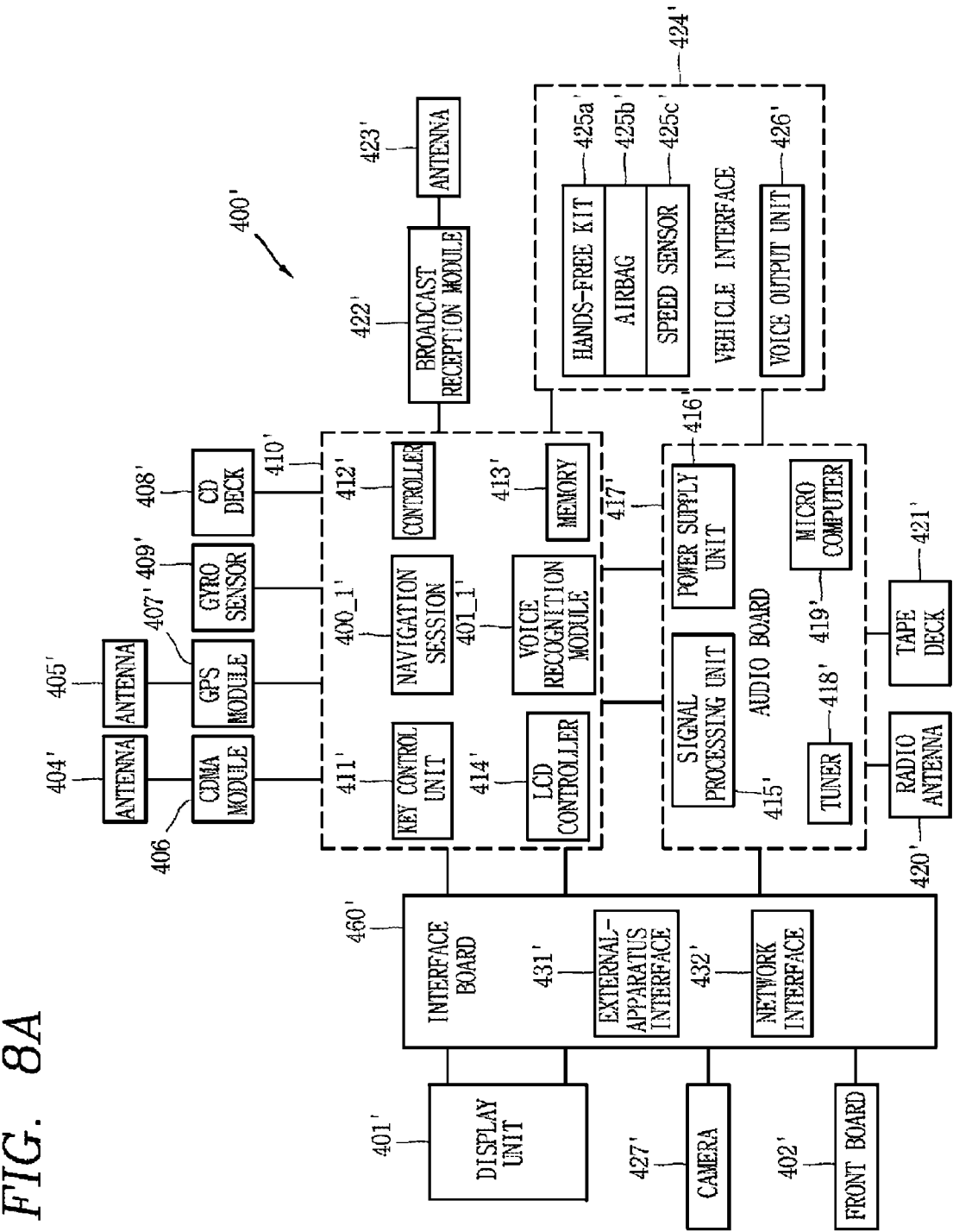
FIGS. 8A and 8B are block diagrams illustrating examples of a vehicle control apparatus.

FIG. 8A is a block diagram illustrating a configuration of the vehicle control apparatus, disclosed in the present specification, according to some implementations.

FIG. 8A illustrates a case where the vehicle control apparatus 400 is realized as in the form of an image display apparatus, a head unit of the vehicle, or a telematics terminal.

As illustrated in FIG. 8A, a vehicle control apparatus 400' is configured to include a main board 410'. A controller (for example, a central processing unit (CPU) 412' that controls operations of the vehicle control apparatus 400', a program for processing or controlling the controller 412', a key controller 411' that controls various key signals, and an LCD controller 414' that controls a liquid crystal display (LCD) are built into the main board 410'.

Map information (map data) for displaying directions-suggestion information on a digital map is stored in the memory 413'. In addition, a traffic information collection/control algorithm for inputting the traffic information according to a condition of a road along which the vehicle moves currently, and information for controlling the algorithm are stored in the memory 413'.

The main board 410' is configured to include a code division multiple access (CDMA) module 406' that is assigned a serial number and is built into the vehicle, a global positioning system (GPS) module 207 that receives GPS signals for identifying a vehicle position, tracking a driving path from a departure point to a destination point, and so forth, transmits traffic information collected by the user, a CD deck 408' for reproducing signals recorded on a compact disk (CD), a gyro sensor 409' and the like. The CDMA module 406' and the GPS module 407' transmit/receive a signal to/from antennas 404' and 405', respectively.

In addition, a broadcast reception module 422' is connected to the main board 410' and receives a broadcast signal through an antenna 423'. A display unit (LCD) 401' that controlled by the LCD controller 414' through an interface board 430', a front board 402' that is controlled by the key controller 411', and a camera 427' that captures an image of a scene inside of and/or outside of the vehicle are connected to the main board 410'. Various video signals and text signals are displayed on the display unit 401'. Buttons for inputting various key signals are provided on the front board 402'. The front board 410' provides the key signal corresponding to the button selected by the user. In addition, the display unit 401' is configured to include a proximity sensor and a touch sensor (touch screen).

A menu key for directly inputting the traffic information is provided on the front board 402'. The menu key is configured in such a manner that the menu key is controlled by the key controller 411'.

The audio board 417' is connected to the main board 410' and processes various audio signals. The audio board 417' is configured to include a microcomputer 419' for controlling the audio board 417', a tuner 418' that receives a radio signal, a power supply unit 416' that supplies electric power to the microcomputer 419', and a signal processing unit 415' that processes various voice signals.

In addition, the audio board 417' is configured to include a radio antenna 420' for receiving the radio signal and a tape deck 421' for reproducing an audio tape. The audio board 417' may be configured to further include a voice output unit (for example, an amplifier) 426' for outputting the voice signal that is signal-processed in the audio board 417'.

The voice output unit (amplifier) 426' is connected to a vehicle interface 424'. That is, the audio board 417' and the main board 410' are connected to the vehicle interface 424'.

A hands-free kit 425a' for inputting the voice signal, an air bag 425b' for driver's or passenger's safety, a speed sensor 425c' for detecting a vehicle speed, and so on may be connected to the vehicle interface 424'. The speed sensor 425c' calculates the vehicle speed and provides information on the calculated vehicle speed to the central processing unit 412'.

A navigation session 400_1' applied to the vehicle control apparatus 400' generates the directions-suggestion information, based on the map data and current position information on the vehicle, and notifies the user of the generated directions-suggestion information.

The display unit 401' senses a proximity touch within a display window through the proximity sensor. For example, when a pointer (for example, a finger or a stylus pen) comes into proximity touch with the display unit 401', the display unit 401' detects a position of the proximity touch and outputs positional information corresponding to the detected position to the controller 412'.

A voice recognition device (or a voice recognition module) 401_1' recognizes a voice generated by the user and performs a corresponding function according to the signal of the recognized voice.

The navigation session 400_1' applied to the vehicle control apparatus 400' displays the driving path on the map data. When the position of the mobile communication terminal 100 is within a predetermined distance from a blind spot included in the driving path, the navigation session 400_1' automatically sets up a connection to a terminal (for example, a vehicle navigation apparatus) mounted in the vehicle in the vicinity and/or to a mobile terminal being carried by a pedestrian in the vicinity over a wireless network (for example, a short-range wireless communication network). Thus, the navigation session 400_1' receives the positional information on the vehicle in the vicinity from the terminal mounted in the vehicle in the vicinity and receives the positional information on the pedestrian from the mobile terminal being carried by the pedestrian in the vicinity.

In some implementations, the main board 410' is connected to an interface unit (not illustrated) 430', and the interface unit 430' (not illustrated) is configured to include an external-apparatus interface unit 431' and a network interface unit 432'.

The external-apparatus interface unit 431' connects an external device and the vehicle control apparatus 400'. To do this, the external-apparatus interface unit 431' is configured to include an A/V input/output unit (not illustrated) or a wireless communication unit (not illustrated).

The external-apparatus interface unit 431' is connected, for example, to an external device, such as a digital versatile disk (DVD) player, a Blu-ray disk player, a game apparatus, a camera, a camcorder, or a computer (notebook computer) in a cable or wireless manner. The external-apparatus interface unit 431' transfers to the controller 412' of the vehicle control apparatus 400' an image, a voice, or data signal that is input from outside through the connected external device. In addition, the image, the voice, or the data signal that is processed in the controller 412' is output to the connected external device. To do this, the external-apparatus interface unit 431' is configured to include an A/V input/output unit (not illustrated) or a wireless communication unit (not illustrated).

The A/V input and output unit is configured to include a USB port, a Composite Video Banking Sync (CVBS) port, a composite port, a S-video port (analog), a Digital Visual Interface (DVI) port, a High Definition Multimedia interface (HDMI) port, a RGB port, a D-SUB port, and the like in order to input an image and a voice signal from the external device to the vehicle control apparatus 400'.

The wireless communication unit performs short-range communication with a different electronic apparatus. The vehicle control apparatus 400' is connected to the different electronic apparatus in accordance with telecommunication standards, such as Bluetooth, Radio Frequency Identification (RFID), Infrared Data Association (IrDA), Ultra Wideband, and ZigBee over the network.

In addition, the external-apparatus interface unit 431' may be connected to various set-top boxes through at least one among the various ports, and may perform an input/output operation while in connection to the set-top box.

In some implementations, the external-apparatus interface unit 431' receives an application or an application list that is present in the adjacent external device, and transfers the application or the application list to the memory 413'.

The network interface unit 432' provides an interface for connecting the vehicle control apparatus 400' to a wire/wireless network, such as the Internet. The network interface unit 432' is configured to include, for example, an Ethernet port for the connection to the wire network. For the connection to the wireless network, telecommunication standards are used such as Wireless LAN (WLAN) (Wi-Fi), Wireless broadband (Wibro), World Interoperability for Microwave Access (Wimax), and High Speed Downlink Packet Access (HSDPA).

The network interface unit 432' transmits or receives data to and from the different user or the different electronic apparatus over a connected network, or a different network linked to the connected network. Particularly, one or more pieces among pieces of content data stored in the vehicle control apparatus 400' are transmitted to the user or the electronic apparatus selected from among other users or other electronic apparatuses that are pre-registered with the vehicle control apparatus 400'.

In some implementations, the network interface unit 432' is connected to a predetermined web page over a connected network or a different network linked to the connected network. That is, the network interface unit is connected to the predetermined web page to transmit or receive data to or from a corresponding server. In addition, items of content or pieces of data are received that are provided by a content provider or a network administrator. That is, content, such as a movie, an advertisement, a game, VOD, and a broadcast signal, and information relating to these, which are provided from the content provide or the network administrator, are received. In addition, update information on firmware and an update file, which are provided by the network administrator, are received. In addition, pieces of data are transmitted to the content provider and the network administrator over the network such as the Internet.

In addition, the network interface unit 432' selects a desired application from applications in the public domain, and receives the selected application, over the network.

Figure 8B:
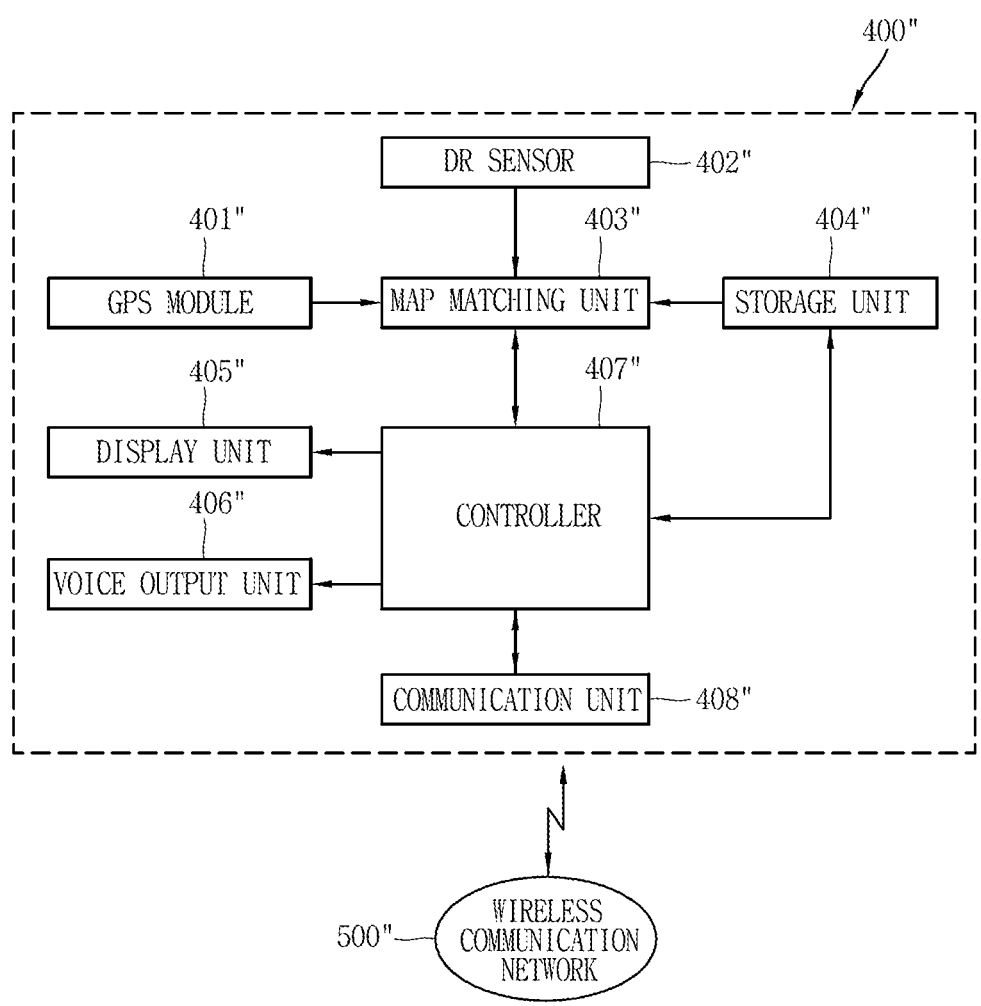

FIG. 8B is a block diagram illustrating a configuration of the vehicle control apparatus, disclosed in the present specification, according to some implementations.

FIG. 8B is a configuration diagram illustrating the vehicle control apparatus 400', focusing on a function of the vehicle navigation apparatus.

If a vehicle control device 400" is realized as the vehicle navigation apparatus, the vehicle control device 400" is categorized into an in-ash type and an on-dash type according to how the vehicle navigation apparatus is installed. The in-dash type navigation (vehicle navigation) apparatus is inserted into a given space secured within a dashboard of the vehicle, and is held in place there. The on-dash type navigation (vehicle navigation) apparatus is held in place on the dashboard of the vehicle, or is held in place in the vicinity of the dashboard using a given support, in a manner that can be attached to and be detached from the dashboard. Thus, in some implementations, the on-dash type navigation apparatus may be portable.

The vehicle control apparatuses 400" according to some implementations include the in-dash type of navigation (vehicle navigation) apparatus and the on-dash type of navigation (vehicle navigation) apparatus. In addition, the navigation (vehicle navigation) apparatuses include information processing apparatuses that are capable of receiving and/or processing the traffic information, such as various types of portable terminals that are capable of performing a navigation function in cooperation with a GPS receiver within the vehicle, which receives a navigation message that is transmitted from a global positioning system (GPS) satellite.

As illustrated in FIG. 8B, the vehicle control apparatus 400" is configured to include a GPS module 401", a dead-reckoning sensor (DR) sensor 402", a storage unit (or memory) 404", a map mapping unit 403", a communication unit 408", a controller 407", a display unit 405", and a voice output unit 406". The GPS module 401" receives a global positioning system (GPS) signal from the satellite and generates first vehicle position data on the navigation apparatus (whose position is defined as being the same as that of the mobile communication terminal 100), based on the received GPS signal. The dead-reckoning sensor (DR) sensor 402" generates second vehicle position data, based on a driving direction of a vehicle and a speed of the vehicle. The map data and various pieces of information are stored in the storage unit 404" (or memory). The map mapping unit 403" generates a vehicle estimation position, based on the first vehicle position data and the second vehicle position data, matches the generated vehicle estimation position with a link (or a map match link, or a map match road) within the map data stored in the storage unit 404", and outputs the matching-caused map information (the result of map matching). The communication unit 408" receives real time traffic information from an information provision center and/or from the vehicle in the vicinity over a wireless communication network 500", receives traffic light-signal information, and performs telephone communication. The controller 407" generates the directions-suggestion information, based on the matching-caused map information method (the result of map matching). The directions-suggestion map (including information on the point of interest) included in the directions-suggestion information and the traffic signal-light information are displayed on the display unit 405". The voice output unit 406" outputs directions-suggestion voice information (a directions-suggestion voice message) included in the directions-suggestion information and a voice signal corresponding to the traffic light-signal information.

At this point, the communication unit 408" may further include a hands-free kit including a Bluetooth module and may receive a broadcast signal including the traffic information in a TPEG format from the broadcasting station through an antenna. The broadcast signal includes not only audio and video data in accordance with various types of specifications, such as ground wave or satellite Digital Multimedia Broadcasting (DMB), Digital Audio broadcasting (DAB), digital Video Broadcasting (DVB-T and DVB-H), but also additional information, such as traffic information and various types of additional data, which is provided through traffic information (TPEG) service and Binary Format for Scene (BIFS) data service. In addition, the communication unit 408" performs synchronizing on a signal band in which the traffic information is provided, demodulates the synchronized signal, and outputs the demodulated signal to a TPEG decoder (which is included in a controller 407).

The TPEG decoder decodes the traffic information in the TPEG format and provides to the controller 407" various type of information that include the light signal information included in the traffic information.

The directions-suggestion information includes not only the map data, but also various types of information relating to driving, such as traffic lane information, speed limit information, turn-by-turn information, traffic safety information, traffic condition information, vehicle information, path-finding information, and the like.

The signal that is received through the GPS module 401" may be configured in such a manner as to provide the position information on the terminal to the vehicle control apparatus 400" using wireless communication methods proposed by the Institute of Electrical and Electronics Engineers (IEEE), such as IEEE 802.11, IEEE 802.15, IEEE 802.16, and IEEE 802.20. IEEE 802.11 is a set of standard specifications for wireless networks, such as wireless LAN and wireless LAN including one portion of Infrared Communication and so on. IEEE 802.15 is a set of standard specifications for wireless Personal Area Network (PAN) including Bluetooth, UWB, ZigBee, and so on. IEEE 802.16 is a set of standard specifications for wireless Metropolitan Area Network (MAN) (Broadband Wireless Access (BWA)) including Fixed Wireless Access (FWA) and so on. IEEE 802.20 is a set of mobile Internet standard specifications for wireless MAN (Mobile Broadband Wireless Access (MBWA)).

The vehicle control apparatus 400" may be configured to further include an input unit. The input unit is used when the user selects a function that is wanted by the user or inputs information. Various devices, such as a keypad, a touch screen, a jog shuttle, and a microphone, are used as the input unit.

The map matching unit 403" generates the vehicle estimation position, based on the first vehicle position data and the second vehicle position data, and reads the map data corresponding to the driving path from the storage unit 404".

The map matching unit 403" matches the vehicle estimation position with a link (road) included in the map data and outputs the matching-caused map information (the result of map matching) to the controller 407". For example, the map matching unit 403" generates the vehicle estimation position, based on the first vehicle position data and the second vehicle position data. The map matching unit 403" matches the generated vehicle estimation position with the links within the map data stored in the storage unit 404", in the linking order, and outputs the matching-caused map information (the result of map matching) to the controller 407". The map matching unit 403" may output information on characteristics of roads, included in the matching-caused map information (the result of map matching), such as one-story road and multi-story road, to the controller 407". In addition, a function of the map matching unit 403" may be realized in the controller 407".

The map data is stored in the storage unit 404". At this point, the map data being stored is included to include geographic coordinates (or latitude and longitude coordinates) indicating latitude and longitude in a unit of degree-minute-second (in a DMS unit). At this point, in addition to the geographic coordinates, the map data being stored may include Universal Transverse Mercator (UTM) coordinates, Universal Polar System (UPS) coordinates, and Transverse Mercator (TM) coordinates.

Various types of information, such as various types of menu screens, points of interest (POI) (hereinafter referred to as "POI"), and information on function characteristics according to a specific position on the map data are stored in the storage unit 404".

Various user interfaces (UI) and/or various graphic user interfaces (GUI) are stored in the storage unit 404".

Data, programs, and so on necessary to operate the vehicle navigation apparatus 400 are stored in the storage 404".

Destination information that is input from the user through the input unit is stored in the storage unit 404". At this point, the destination information is on the destination point, or on any one among the destination point and the departure point.

The image information (or directions-suggestion map) included in the direction-suggestion information generated by the controller 407 is displayed on the display unit 405". At this point, the display unit 405 is configured to include the touch sensor (touch screen) and the proximity sensor for the display unit. In addition, the directions-suggestion information includes not only the map data, but also the various types of information relating to driving, such as the traffic lane information, the speed limit information, the turn-by-turn (TBT) information, the traffic safety information, the traffic condition information, the vehicle information, the path-finding information and the like.

When the image information is displayed, various menu screens and various items of content, such as the directions-suggestion information, are displayed on the display unit 405", using a user interface and/or a graphic user interface that are included in the storage unit 404". At this point, the content that is displayed on the display unit 405" includes the menus screen including various pieces of text or image data (including the map data or various types of information data), a menu screen including icons, a list menus, a combo box, and the like, and the like.

The voice output unit 406" outputs voice information (or a voice message for the directions-suggestion information) included in the directions-suggestion information generated by the controller 407". At this point, the voice output unit 406" may be an amplifier or a speaker.

The controller 407" generates the directions-suggestion information, based on the matching-caused map information, and outputs the generated directions-suggestion information to the display unit 405" and the voice output unit 406". At this point, the directions-suggestion information is displayed on the display unit 405".

The controller 407" receives the real-time traffic information from the information provision center and/or the terminal (vehicle navigation device) mounted in the vehicle in the vicinity and generates the directions-suggestion information.

The controller 407" establishes a connection to a call center through the communication unit 408" and thus makes a telephone call or transmits/receives information between the vehicle control apparatus 400" and the call center. At this point, the communication unit 408" may further include a hand-free module that has a Bluetooth function which uses a short-range wireless communication method.

When a POI search menu is selected by the user, the controller 407" searches for the POI positioned on a path from a current position to the destination point, and displays the resulting POI to the display unit 405". At this point, the controller 407" searches for the POI (a path to the POI does not need to be changed (to be researched for), in which case the POI is positioned to the left or to the right of a driving road) positioned on the path from the current position to the destination point and for the POI (a path to the POI needs to be changed, in which case a predetermined path has to be changed in order to drive by way of the POI in the vicinity) positioned in the vicinity of the path from the current position to the destination point, and displays the resulting POI on the display unit 405".

Figure 8C:
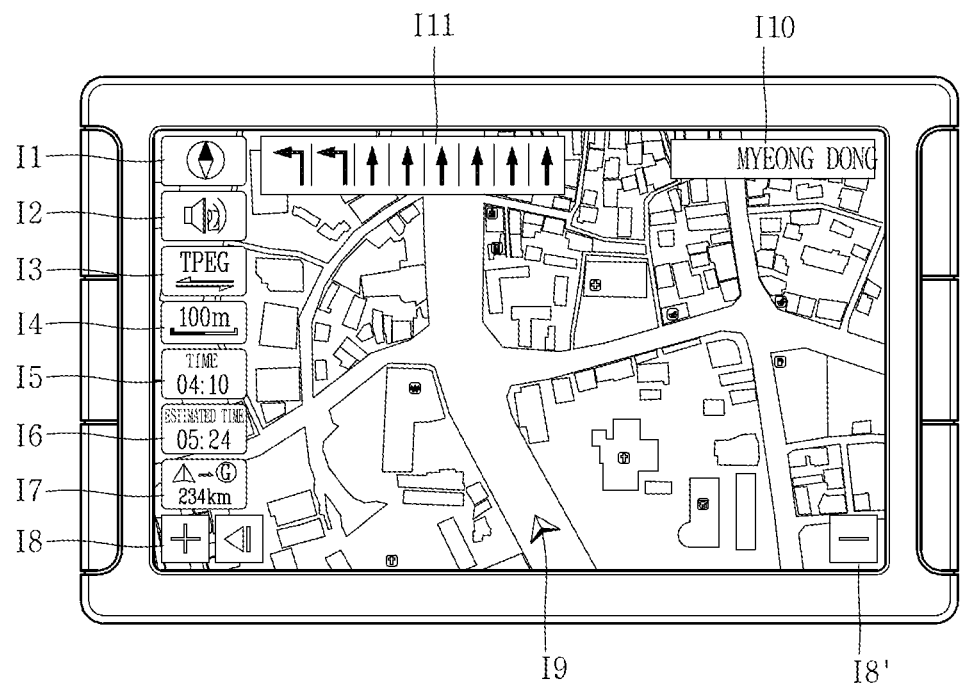
FIG. 8C is a sketch illustrating an example of a screen associated with a navigation function.

FIG. 8C is a diagram illustrating a screen associated with a navigation function, disclosed in the present specification, according to some implementations.

The screen illustrated in FIG. 8C is a screen that is displayed by the mobile terminal 100, the wearable device 200 or 200', or the vehicle control apparatus 400.

If the mobile terminal 100 is realized as in the form of a mobile terminal, a smart phone, a laptop computer, a digital broadcast terminal, a personal digital assistant (PDA), a portable multimedia player (PMP), a wearable device, and the like, one or more among constituent elements illustrated in FIG. 8C may be displayed or none of the constituent elements may be displayed.

As illustrated in FIG. 8C, an icon 11 indicating a compass direction of the map is displayed on one region of the screen on the display unit to which a screen associated with the navigation function is provided. The map is displayed on the display unit to which the screen associated with the navigation function is provided, in such a manner that a specific direction (for example, the true north direction of the Earth), a moving direction of a moving object, a direction of the destination point, and the like are displayed fixed to an upper portion of the screen.

An icon 12 indicating whether or not a sound output module 162 is activated and a volume setting is displayed on one region of the screen on the display unit to which the screen associated with the navigation function is provided. The user can activate or inactivate the sound output module 162 or adjust the volume by applying the touch input to the icon 12.

An icon 13 indicating whether or not a path search function is activated that is in accordance with Transport Portal Experts Group (TPEG) specifications for transmission of traffic information is displayed on one region of the screen on the display unit. Transport Portal Experts Group (TPEG) was found in 1997 by the European Broadcasting Unit for the purpose of establishing protocols for traffic information. In a navigation system, a path suggestion function that uses real time traffic situation information is in accordance with TPEG.

An icon 14 indicating a scale of the map data is displayed on one region of the screen on the display unit.

An icon 15 indicating present time is displayed on one region of the screen in the display unit. In addition, an icon 16 indicating estimated time at which the moving object arrives at a predetermined destination point is displayed on one region of the screen on the display unit. Furthermore, an icon indication estimated time that it takes the moving object to arrive at the predetermined destination point is displayed on one region of the screen on the display unit.

An icon 17 indicating a distance to the predetermined destination point is displayed on one region of the screen on the display unit.

An icon 18 or an icon 18' for increasing or decreasing a size of the displayed map, respectively, is displayed on one region of the screen on the display unit.

An icon 19 indicating a position and a moving direction of the moving object is displayed on one region of the screen on the display unit. The icon 19 may be displayed on a point on the map, which corresponds to the current position of the moving object. In addition, the moving direction of the moving object is displayed as a direction of a sharp point of an arrow in the icon 19, and the like.

An icon 110 indicating a name of a place in which the moving object is located is displayed on one region of the screen on the display unit.

If the vehicle drives down a street, an icon 111 indicating lanes of the street is displayed on one region of the screen on the display unit.

A path to the predetermined destination point 112 (refer to FIG. 8C) is displayed on the display unit. If the destination point of the moving object is not set, the path may not be displayed.

The functions (for example, including the navigation function) that are performed by the vehicle 400 described above are performed the mobile terminal 100 or the wearable device 200 or 200' that is connected to the vehicle control device 400 in a wired or wireless manner.

In addition, the vehicle control device 400 and the mobile terminal 100 may perform functions in cooperation with each other or in conjunction with each other.

To do this, the mobile terminal 100 or the wearable device 200 is configured to include a constituent element that is the same as, is similar to, and corresponds to that included in the vehicle control apparatus 400.

For example, the acceleration sensor provided in the mobile terminal 100 or the wearable device 200 or 200' plays a role of the acceleration sensor included in the vehicle control apparatus 400.

For the cooperation or conjunction between the vehicle control apparatus 400 and the mobile terminal 100, a virtual network computing (VNC) method is applied.

The virtual network computing (VNC) means a graphic desktop sharing system that remotely controls a different computer (or a different terminal) using a RFB protocol in an computer environment.

The VNC transmits keyboard and mouse events or a touch event from one terminal to another, and thus provides a method of updating a graphic screen over the network.

In addition, the functions that are performed by the vehicle control device 400 described above are shared between the vehicle control device 400 and the mobile terminal 100 or the wearable device 200 or 200' and thus are performed.

That is, when it comes to performing a specific function, among the functions that are performed by the vehicle control apparatus 400 described above, one portion of the specific function is performed by the vehicle control apparatus 400, the other portions of the specific function are performed by the mobile terminal 100 or the wearable device 200 or 200'.

For example, in a case of the air conditioning function for the vehicle, a setting temperature is input into an air conditioner that is provided within the vehicle, by the mobile terminal 100 or the wearable device 200 or 200'. The vehicle control apparatus 400 performs control in such a manner that the air conditioner operates to maintain the setting temperature that is input.

It is apparent to a person of ordinary skill in the art that the technology relating to the vehicle control apparatus, disclosed in the present specification, can be realized in a different form within a range that does not deviate from the technological idea disclosed in the present specification.

System that Determines Whether the Driver Drives in a Dangerous State

Referring to FIGS. 9A to 13, some examples of mobile terminals and vehicle control apparatuses that are configured to determine whether the driver is in a dangerous driving state, according to some implementations, are described in detail below.

The mobile terminal that determines whether the driver drives in a dangerous state, disclosed in the present specification, according to some implementations, is described in detail below, and among the same constituent elements, the description of the preceding one substitutes for a description of the following one in order to avoid the redundant descriptions.

As described with reference to FIG. 1, above, a mobile terminal (e.g., mobile terminal 100 in FIG. 1), according to some implementations, may be configured to include a communication unit 110, a biological information obtainment unit 145, and a controller 180.

The biological information obtainment unit 145, as described above, obtains the biological information through a specific portion of the user's body (the terms user and "driver" are interchangeably used in the present specification).

According to some implementations, the biological information obtainment unit 145 measures a bio-signal that is generated due to a physiological potential difference in the human body, and as one example, is configured to include at least one among PPG, ECG, GSR, EEG, EMG, and EGO sensors.

Figure 9A:
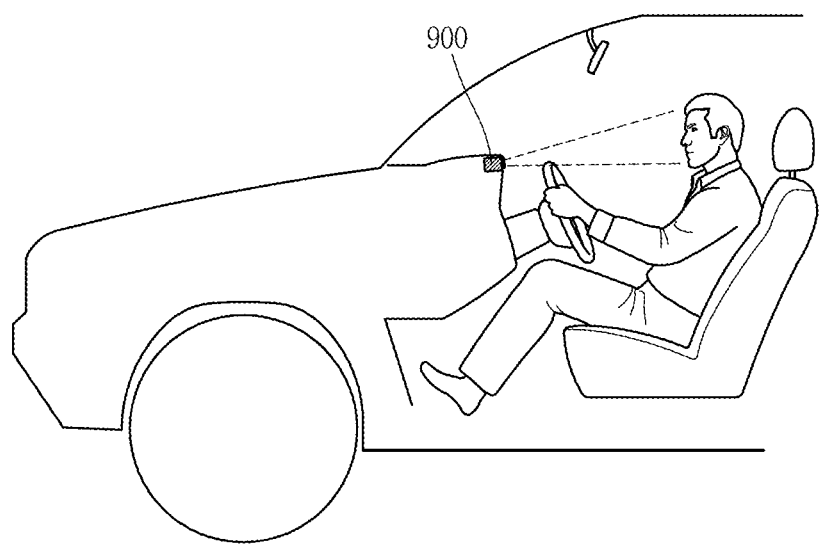
FIGS. 9A and 9B are sketches illustrating examples of an image obtainment apparatus.
Figure 9B:
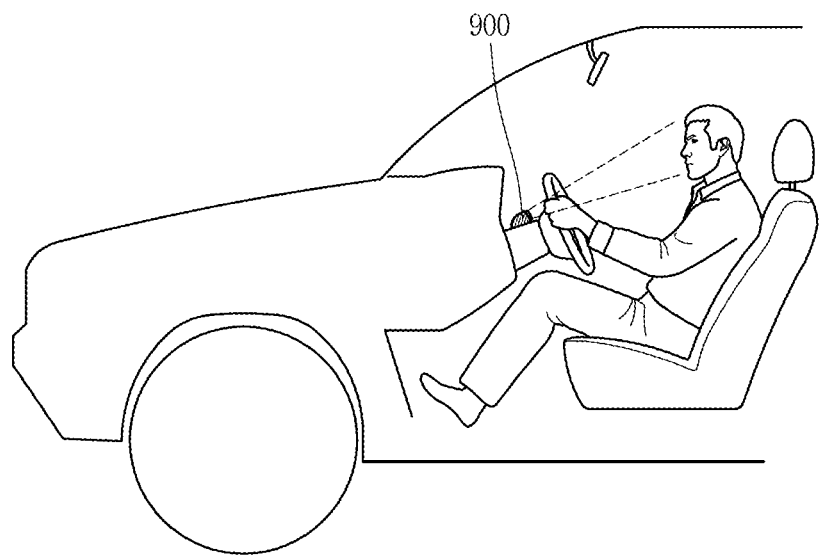

FIGS. 9A and 9B are diagrams illustrating examples of an image obtainment apparatus, disclosed in the present specification, according to some implementations, installed in a vehicle.

The image obtainment apparatus 900 performs processing of image frames for a static image and a moving image, which are captured by an image sensor, and obtains an image of the user (e.g., like a camera).

In some implementations, the image obtainment apparatus 900 may be installed toward the user in order to obtain the image of the user. However, the image obtainment apparatus 900 may be positioned inside of or outside of the vehicle.

As described below, the determining of whether the user is drowsy, distracted, stressful, or in a like state, according to some implementations is based on a user's facial expression and features in addition to the biological information on the user. Because of this, as one example, as illustrated in FIGS. 9A and 9B, the image obtainment apparatus 900 is installed within the vehicle, and in some implementations the image obtainment apparatus 900 may be installed on a dashboard or in the vicinity of the dashboard, or installed to be in a straight line with a rotation axis (e.g., in FIG. 9B) of the steering wheel.

In some implementations, the image obtainment apparatus 900 is held in place by a stand that is attachable to one internal surface of the vehicle, and the image obtainment apparatus 900 being held in place by the stand is installed fixedly toward the user.

There may be one or more image obtainment apparatuses 900 that obtain the image of the user. If there are multiple image obtainment apparatuses 900, then the controller 180 may, in some implementations, obtain a three-dimensional image of the user using the image information that is obtained by the multiple image obtainment apparatuses 900.

In order to obtain the three-dimensional image of the user, the multiple image obtainment apparatuses 900 may be installed toward the user, but from different directions toward the user.

As described below, the controller 180 may use the multiple pieces of image information in order to recognize a user's facial expression, the time for which user's eyes open, user's blinking, a direction of a user's face, a direction of a user' gaze, and the like. In some implementations, the controller 180 calculates coordinates of a position at which the user's face (or the user's head) is positioned in space, from the multiple image obtainment apparatuses 900, selects one that has a highest rate of recognition of the user' face, from among the multiple image obtainment apparatuses 900, and uses the image information that is obtained by the selected image obtainment apparatus 900 in order to recognize the user's facial expression, the time for which the user's eyes open, the user's blinking, the direction of the user's face, the direction of the user' gaze, and the like.

In addition, in order to obtain an image of a region of interest (ROI) according to coordinates of a point at which the user gazes, the multiple image obtainment apparatuses 900 may, in some implementations, be installed toward multiple regions inside of and outside of the vehicle in such a manner as to obtain image information on the multiple regions inside of and outside of the vehicle.

In addition, the image obtainment apparatus 900 may be configured to include at least one motor for moving a lens or the image obtainment apparatus 900 itself in upward, downward, leftward, and rightward directions or for rotating the lens and the image obtainment apparatus 900, in order that the image information on the regions inside of and outside of the vehicle is obtained or the rate of recognition of the user's face is increased using as few image obtainment apparatuses as possible.

If the image obtainment apparatus 900 does not face toward the ROI or does not recognize the user's face, the lens or the image obtainment apparatus 900 itself may be tiltable so that the user's face is extracted from the obtained image information.

The communication unit 110 receives image information on the user from the image obtainment apparatus 900.

The image obtainment apparatus 900 transmits the image information directly to the mobile terminal 100 or the vehicle control apparatus 400 through the built-in or outer-mounted cable or wireless communication unit. Alternatively, the mobile terminal 100 or the vehicle control apparatus 400 receives the image information, and transfers the received image information to the vehicle control apparatus 400 or the mobile terminal 100.

The controller 180 detects whether the user drives in a dangerous state, based on information received from one or more sensors, such as at least one of the image information received through the communication unit 110 or the biological information obtained through the biological information obtainment unit 145.

As examples, a dangerous driving-state in which the user drives includes at least one among a drowsy driving-state, a distracted driving-state, or a stressful driving-state.

In some implementations, controller 180 determines whether the user drives in the drowsy state and/or in the distracted state, based on the image information.

In addition, the controller 180 determines whether the user drives in the drowsy state and/or in the stressful state, based on the biological information.

Therefore, the controller 180 determines whether the user drives in the drowsy state, in the distracted state, or in the stressful state, or generates information on a danger level of a dangerous driving-state for each of the drowsy driving-state, the distracted driving-state, and the stressful driving-state.

Particularly, in some implementations, the controller may use both the image information and the biological information, synthesize the two types of information, and determine whether the user drives in a dangerous state (e.g., the drowsy state). By utilizing both types of information (or more), improved precision may be achieved to determine the level of danger that the dangerous driving state evaluated for the user corresponds to.

For example, the controller 180 may determine that the image information or the biological information alone do not indicate a dangerous driving state, but the controller 180 may analyze the combination of both the image information and the biological information and determine that the combined analysis indicates a dangerous driving state.

In some implementations, based on results of one type of sensor, the controller 180 may control other sensors (e.g., to collect more detailed or greater amounts of information). As such, the controller 180 may refine and combine information from different sensors to make a determination of dangerous driving state.

In some implementations, the controller 180 may adjust an initial value of the image information and/or an initial value of the biological information (e.g., when the user first drives the vehicle) for a certain amount of time before the controller 180 makes the determination of the dangerous driving-state or a danger level. In some implementations, the image information and/or the biological information may be determined based on the adjusted initial value.

Drowsy Driving-State

Some examples of classifying a drowsiness state of a user is shown in Table 1, below. In this example, three different drowsiness scales are shown, the Human Fatigue Scale (HFC), the Karolineska Sleepiness Scale (KSS), and the Stanford Sleepiness Scale (SSS), although in general other drowsiness classifications may be used. In this example, each scale has a certain number of total levels for evaluation of drowsy driving-state, such as 7 levels for the HFC and SSS, and 9 levels for the SSS, as shown in Table 1.

TABLE 1

| Level | | HFC (Human Fatigue-Scale) | KSS (Karolineska Sleepiness Scale) | SSS (Stanford Sleepiness Scale) |
|---|---|---|---|---|
| Activated | 1 | Wide awake, active attention | Extremely alery | Feeling active, vital, alert, wide awake |
| | 2 | | Very alert | |
| | 3 | Fresh and concentrate but focused attention | Alert | Functioning at a high level but not at peak, able to concentrate |
| | 4 | Neither activated nor tired, reactivity without notable tendency | Rether alert | Relaxed, awake but not fully alert, responsive |
| | 5 | | Neither alert nor sleey | |
| Tired | 6 | First sign from tiredness but effortless awake | Some signs of sleepiness | A little foggy, let down |
| | 7 | Tired but mainly on the actions aligned | Sleepy, no effort to stay awake | Foggy beginning to lose track, difficulty staying awake. |
| | 8 | Struggle against the sleep, actions falls heavy but widely receptable | Sleepy, some effort to stay awake | Sleepy, prefer to lie down, woozy |
| | 9 | Absently, impassive, long chapter without activity, Second sleep peobable or appears | Very sleep, great sffort to keep awake, fighting sleep | Almost in reverie, cannot stay awake, sleep onset appears imminent |

In some implementations, when determining whether the user drives in a drowsy state (e.g., using the image information), the controller 180 determines whether the user drives in the drowsy state using various features of the user's image, such as the user's facial expression, a time during which the user's eyes are open, the user's blinking, the direction of the user's face, or a combination of such features.

As one example, the controller 180 may determine whether the user drives in the drowsy state based on eyelid open/closed states. For example, the controller 180 may determine a ratio of the time during which an eyelid is open to the time during which the eyelid is closed (e.g., over a particular period of time), and determine a drowsiness condition based on the ratio of open-to-closed times.

For example, the closed state of the eyelid closes may be a state in which the eyelid closes by a particular amount (e.g., the eyelid closes to approximately 70% or 80% of a difference between maximum and minimum sizes of the user's eye). The time during which the eyelid is determined to be closed may then be estimated as the time during which the eyelid is closed by this particular amount.

As another example, the controller 180 may determine whether the user drives in the drowsy state, based on the user's blinking.

A number of techniques may be used to determine drowsiness based on a user's blinking. For example, the controller 180 may determine the time it takes for the user to blink (i.e., a time it takes for the user to close and open an eyelid), and may generally determine that a longer time required to blink (i.e., a slower blinking rate or closure rate) indicates a more drowsy condition. The blink rate may be used in a number of ways to determine drowsiness.

As a specific example, the average of squared blinking rates may be computed by taking a sum of square values of closure rates and dividing the sum by the number of times that the user blinks, in order to obtain an average value of squares (e.g., related to root-mean-square value). According to such an average value, it is determined whether the user drives in the drowsy state. Alternatively, the average of closure rates may be computed by taking a sum of the closure rates of the eyelid by which it is determined that the user blinks and dividing the sum by the number of times that the user blinks, in order to obtain an average value. According to such an average value, it is determined whether the user drives in the drowsy state.

In some implementations, the closure rate of the eyelid by which it is determined that the user blinks is the closure rate of the left eyelid or the right eyelid, whichever is greater in value. Alternatively, the closure rate of the eyelid is an average value of the closure rate of the left eyelid and the closure rate of the right eyelid.

In some implementations, the controller 180 may determine drowsiness based on the time for the user to blink one time (closure time) exceeding a threshold time. As an example, the controller 180 determines whether the user drives in the drowsy state based on how often the user's closure time equals or exceeds a threshold time (e.g., approximately 0.5 second or 1 second).

As another example, when the closure time equals to or exceeds the threshold time even just once, then based on this, the controller 180 may determine whether the user drives in the drowsy state.

As another example, the controller 180 may determine whether the user drives in the drowsy state based on a value that results from determining the number of times that the closure time equals to or exceeds a threshold time (e.g., approximately 2 seconds), and dividing this number by the number of times that the closure times equals to or exceeds a threshold time in successive occurrences (e.g., the number of times that two closures in a row exceeds the threshold time, or three closures in a row exceeds the threshold time, etc.).

As a specific example, a determination that a user's eyelid closure time equals to or exceeds a threshold time (approximately 2 seconds) may be expressed as a "1", and otherwise a blinking event may be expressed with a "0," so that a sequence of detecting a user's blinking closure times over a period of time may be expressed as 00001100001111100001110000. This sequence of 0's and 1's may be translated into an expression (2+4+3)/3=3, using the technique of detecting successive occurrences of closure times that satisfy a threshold, describe above. In this example, a value of 3 is used for determining whether the user drives in the drowsy state. That is, the controller 180 evaluates the drowsy state in which the user drives according to the value that is calculated in this manner. It is determined that the greater the obtained value, the higher the level for the evaluation of the drowsy state in which the user drives.

As another example, based on a frequency with which the user blinks, the controller 180 may determine whether the user drives in a drowsy state. Specifically, the controller 180 may determine drowsiness based on determining that the number of times that the eyelid closure time equals to or exceeds a threshold time (e.g., approximately 2 seconds) is a particular number n, and determining whether the user drives in the drowsy state based on the frequency of n.

As another example, the controller 180 may determine whether the user drives in the drowsy state based on a speed at which the user blinks.

Specifically, in this example, the speed of the user's eyelid from a point where the eyelid opens to a point where the eyelid closes is measured and an average value, or the average eye closure speed (AECS), is obtained by dividing a sum of the measured speeds by the number of times that the user blinks. Then, it is determined whether the user drives in the drowsy state, based on the average value (AECS). Alternatively, another type of average value, the ratio between the amplitude and peak closing velocity (APCV), is obtained by dividing the amplitude of blinking by a value of the maximum speed from the point where the eyelid opens to the point where the eyelid closes. Then it is determined whether the user drives in the drowsy state, based on the average value (APCV).

In some implementations, the APCV may be based on the most recent value, or based on an average value of the APCV's that are calculated multiple times.

As another example, the controller 180 may determine whether the user drives in the drowsy state based on whether or not the pupil of the user's eye contracts (or whether or not the iris of the user's eye slackens).

As another example, if the direction of the user' face changes to upward and downward directions over time, then the controller 180 determines that the user lowers his/her head repeatedly (e.g., nodding his/her head) and thus may determine whether the user drives in the drowsy state.

As another example, the controller 180 may determine based on the user's facial expression that the user yawns, and thus may determine whether the user drives in the drowsy state.

As described above, the controller 180 determines whether the user drives in the drowsy state, based on one or more of various features extracted from a captured image, such as among the user's facial expression, the time for which the user's eye opens, the user's blinking, and the direction of the user's face. In some implementations the controller 180 may determine whether the user drives in the drowsy state based on a combination of the determination bases described above (e.g., to improve accuracy of drowsiness determination), and may combine different types of features in suitable ways to make a drowsiness determination.

For example, if based on the combination of multiple determination bases, the controller 180 may determine whether the user drives in the drowsy state, or determine the level of a drowsy state in which the user drives, by applying a weight to each of the multiple determination bases (for example, a weight to the user's facial expression, a weight to the time for which the user's eye opens, a weight to the user's blinking, and/or a weight to the direction of the user's face).

The weights may be determined using various techniques. In some implementations, the weights may be determined through a learning model based on a database of the determination bases.

For example, a learning model may be generated based on a database of image information and biological information for the user, or based on other people (which may or may not include the user). Based on the generated learning model, the controller 180 may determine the dangerous driving-state or the danger level for the user's particular measurements.

In addition to the various techniques of determining drowsiness based on image information, described above, the controller 180 may additionally or alternatively use information from other sensors, such as biological information.

In some implementations, as described above, the controller 180 determines whether the user drives in the drowsy state based on the biological information that is obtained through the biological information obtainment unit 145.

For example, the controller 180 may determine whether the user drives in the drowsy state based on signals from various sensors, such as a bio-signal for an electromyogram measured through an EMG sensor, or based on a galvanic skin reflex signal measured through a GSR sensor, etc.

In some implementations, the controller 180 may use multiple pieces of biological information, and apply weights to the multiple pieces of biological information, to determine drowsiness.

The weights may be determined using any suitable technique. For example, when using multiple determination bases, such as the values measured by the EMG and GSR sensors and the like, the controller 180 the weights may be set through a learning model based on a database of the determination bases.

In some implementations, the learning model may be based on a database of information that may include the particular user and/or other persons. Based on the generated learning model, the controller 180 determines the dangerous driving-state or the danger level for the user.

In some implementations, if the controller 180 determines drowsiness based only on the image information, or based only on the biological information, precision may be limited (e.g., the number of the levels for the evaluation of the drowsy state in which the user drives may be limited), and it may be difficult to precisely determine to the user's drowsy condition.

In some implementations, the controller 180 may determine whether the user drives in the drowsy state, based on the biological information in addition to the image information.

When determining drowsiness based on both the image information and the biological information, the controller 180 may determine drowsiness by applying a weight to each of the image information and the biological information.

For example, when the controller 180 evaluates the level of the drowsy state in which the user drives, a relationship between a weight of the image information and a weight of the biological information may be related in any suitable way. As a specific example, in some implementations, the weight assigned to the image information may be greater than the weight assigned to the biological information.

The relationship between the weight assigned to the image information and the weight assigned to the biological information may be different depending on whether the controller 180 is measuring a drowsy driving-state, a distracted driving-state, or a stressful driving state. Accordingly, in some implementations, the weights may be differently applied to the image information and the biological information, depending on whether the controller 180 is determining a drowsy driving-state, a distracted driving-state, or a stressful driving-state, Thus, in some implementations, the controller 180 may determine which one of the drowsy driving-state, the distracted driving-state, and the stressful driving-state the dangerous state in which the user drives corresponds to, or may determine the level for the evaluation of a specific dangerous driving-state.

Figure 13:
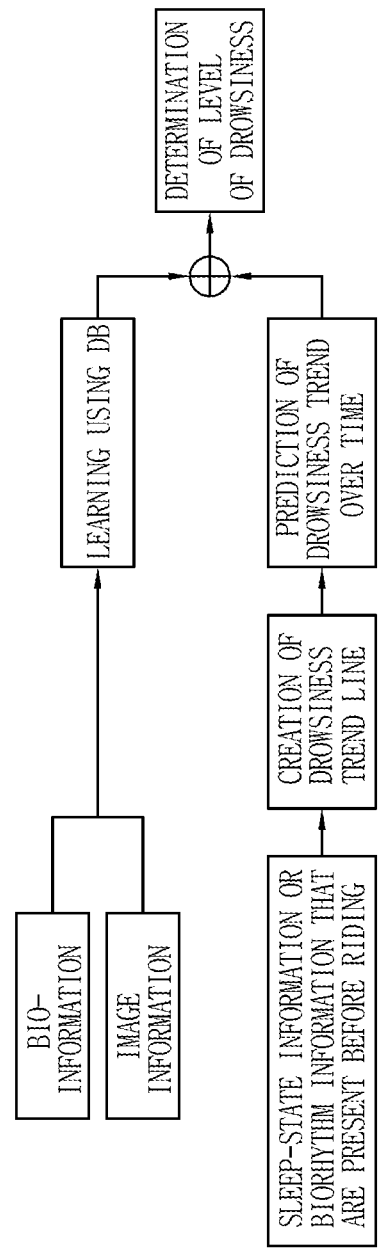
FIG. 13 is a flow chart illustrating an example of determining whether a user drives in a drowsy state and a level of the drowsy state in which the user drives.

In some implementations, when the controller 180 determines whether the user drives in the drowsy state, or the level for the evaluation of the drowsy state in which the user drives, as described above, the image information and the biological information may both be considered, and in some implementations additional consideration may be given to a drowsiness trend line created using at least one among sleep-state information and biorhythm information for the user, which may be available before the user drives in the vehicle (e.g., refer to FIG. 13).

Figure 10:
FIG. 10 is a diagram illustrating an example of a drowsiness trend line for a user.

FIG. 10 is a diagram illustrating an example of a drowsiness level trend line for a user. FIG. 13 is a flow chart illustrating an example of a process for determining whether the user drives in the drowsy state and the level of the drowsy state in which the user drives. The description below will be in reference to both FIGS. 10 and 13.

As illustrated in the example of FIG. 10, the level of drowsiness that is determined by the controller 180 can change over time.

While the user wears the mobile terminal 100, the mobile terminal 100 may obtain various types of information (e.g., biological information) about the user continuously or periodically.

The mobile terminal 100 may, in some implementations, also analyze a sleep pattern of the user before the user rides in the vehicle, and create the drowsiness trend line.

For example, the mobile terminal 100 may analyze at least one among sleep-state information or biorhythm information for the user, based on various sensor information, such as information on a user's movement measured using an acceleration sensor, a G-sensor, a gyroscope sensor, a motion sensor and the like included in the sensing unit 140, and/or based on information on user's breath, a change in a user's pulse rate, a user's electromyogram and the like that are measured using the PPG, EMG, GSR sensors included in the biological information obtainment unit 145.

As a specific example, the controller 180 may analyze a period of time from when the user's sleep starts and to when the user's sleep ends, a movement frequency during the sleep, movement extent, sleep stages (from a stage between sleep and wakefulness to a deep sleep state), a sleep rhythm, a sleep pattern, and the like, using the information that is measured continuously or periodically for a given time as described above, and calculates the drowsiness trend line as illustrated in FIG. 10, based on the analyzed information.

The drowsiness trend line is a graph illustrating levels of drowsiness over time that depend on whether or not the user rides in the vehicle or whether or not the user drives the vehicle. As in FIG. 10, the drowsiness trend line illustrates an initial level of the drowsy state in which the user drives immediately after the user rides in the vehicle or immediately after the user starts to drive the vehicle, the time for which the initial level of the drowsy state in which the user drives is maintained until the level of the drowsy state in which the user drives is changed, and a change rate over time of the level of the drowsy state in which the user drives.

The controller 180 predicts the level of the drowsy state in which the user drives using the drowsiness trend line that is calculated above.

That is, the mobile terminal 100 analyzes the sleep-state information using the biological information that is obtained before the user rides in the vehicle or before the user drives the vehicle, and by calculating the drowsiness trend line based on the analyzed sleep-state information, predicts the level of the drowsy state over time in which the user drives after the user rides in the vehicle or after the user drives the vehicle.

In this manner, the mobile terminal 100 may predict the level of the drowsy state in which the user drives, and may alert the user to the predicted level of the drowsy state in which the user drives using various means before the driver drives in such a drowsy state (which may result in the driving of the vehicle being disturbed). Thus, a possible traffic accident due to the drowsy driving-state can be prevented.

When the controller 180 determines the level for the evaluation of the drowsy state in which the user drives, the controller 180 combines a first drowsiness level calculated based on the image information and the biological information, and a second drowsiness level calculated based on the drowsiness trend line and thus calculates the precise level of the drowsy state in which the user drives.

In some implementations, weights may be applied to each of the first drowsiness level and the second drowsiness level, and thus the level of the drowsy state in which the user drives may be calculated.

For example, the weight that is applied to each of the first drowsiness level and the second drowsiness level may be predetermined by the user input or may be adaptively changed by applying an input conforming the finally-determined level of the drowsy state in which the user drives.

As a specific example, if the level of the drowsy state in which the user drives, which is finally determined, is a level 3, but the confirming input that is applied through the user input unit 130 is a level 2, then the weight may be changed in such a manner that the finally-determined level of the drowsy state in which the user drives is a level 2.

Distracted Driving-State

In some implementations, based on the image information and the biological information, the controller 180 can determine whether the user drives in a distracted state, in which case a dangerous driving-state may result.

In some implementations, the controller 180 may determine whether the user drives in the distracted state using image information. For example, the controller 180 may determine whether the user drives in the distracted state using one among the direction of the user's face and the direction of the user's gaze, or a combination of them.

As one example, the controller 180 calculates the direction of the user's face and the direction of the user's gaze, based on the image information that is obtained through one or more image obtainment apparatuses 900, As a specific example, the controller 180 may determine a calculated direction of the user's face and a calculated direction of the user's gaze, and determine whether the user drives in the distracted state based on the calculated values.

In some implementations, the controller 180 may determine a level of the distracted state in which the user drives, taking into consideration the direction in which the user gazes, the extent to which the user's gaze changes, the time for which the user's gaze stays, and the like.

In some implementations, if the controller 180 determines whether the user drives in the distracted state using one among the direction of the user's face and the direction of the user's gaze or a combination of them, the controller 180 may select at least one image obtainment apparatus 900 that corresponds to coordinates of a point at which the user gazes, among the one or more image obtainment apparatuses 900.

That is, at least one image obtainment apparatus that faces toward the user's ROI may be selected from among the image obtainment apparatuses 900.

Accordingly, the controller 180 recognizes at least one object from the image information that is obtained by the selected image obtainment apparatus 900. The controller 180 may cause the mobile terminal 100 to execute a control command that corresponds to the recognized object, or transmits the control command to the different mobile terminal 100, the vehicle control apparatus 400, or the like, thereby causing the different terminal 100, the vehicle control apparatus 400, or the like to execute the control command.

Figure 11A:
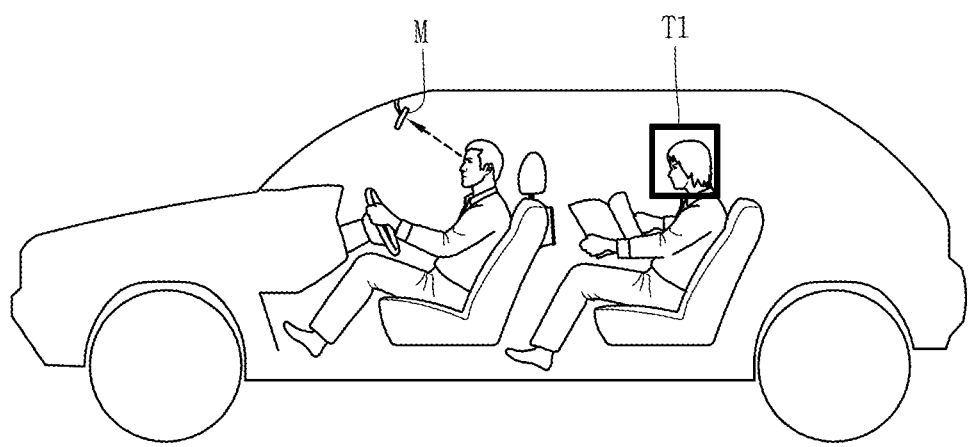
FIGS. 11A and 11B are diagrams illustrating examples of a distracted driving-state in which the user drives.
Figure 11B:
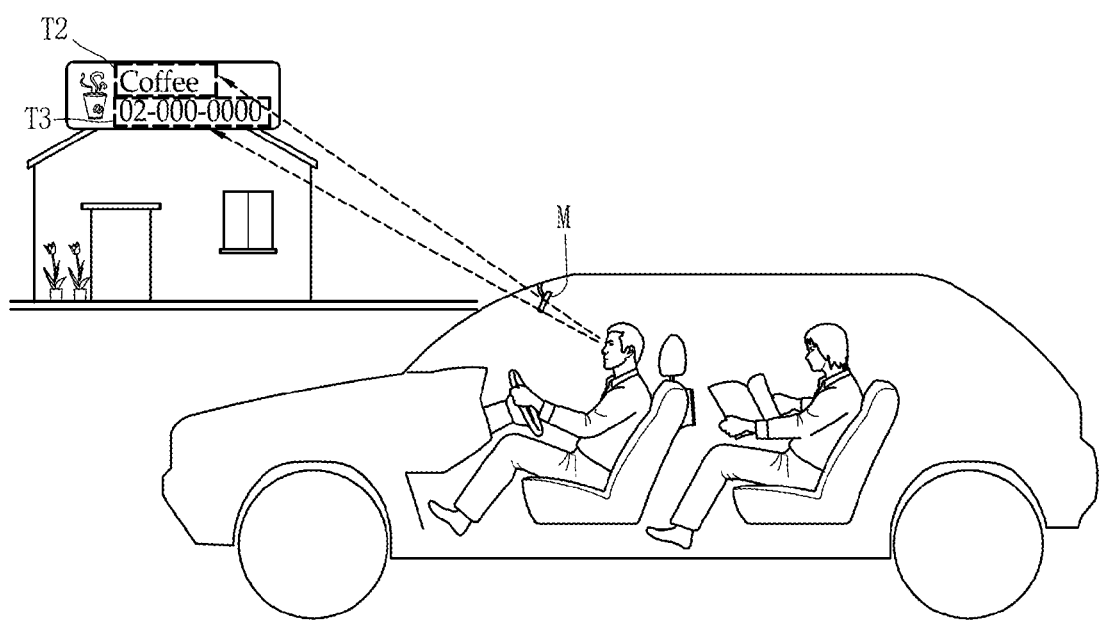

As one example, as illustrated in FIGS. 11A and 11B, if the user gazes at an internal rear view mirror M, the controller 180 may recognize that the user is not gazing forward, and may thus determine that the user drives in a distracted state, in which case a dangerous driving-state may result.

Then, for example, the controller 180 may determine that the coordinates of the point at which the user gazes corresponds to the internal rear view mirror (M), select the backward-direction image obtainment apparatus (not illustrated) that corresponds to the internal rear view mirror M, and obtain the image information from the backward-direction image obtainment apparatus.

Accordingly, the controller 180 may recognize at least one object (T1) from the information obtained from the backward-direction image obtainment apparatus, and if the object T1 is a person, may recognize a face of the person.

If the controller 180 recognizes a face according to the control command that corresponds to the object T1, then because the recognized object is a face, the controller 180 may execute a control command that corresponds to the recognized face. As a specific example, the controller 180 may extract name information and the like that correspond to the recognized face using, for example, a face-related database that is stored in the memory 160.

In addition, the controller 180 may receive the biological information on the object T1 from the mobile terminal that corresponds to the recognized facial expression and/or the recognized face, determine a state of the object TI, and may output a result of the determination through an output unit 150.

For example, the controller 180 may output a voice "Cabin passenger falls asleep," or "Cabin passenger breaths faster than in a normal situation," through the output unit 153, based on the backward-direction image obtainment apparatus, and thus the use can take a prompt action according to the state of the recognition target object.

As another example, as illustrated in FIG. 11B, if the user gazes out of the side window in the driver seat of the vehicle, then the controller 180 may recognize that the user is not gazing forward, and may determine that the user drives in the distracted state, in which case a dangerous driving-state may result.

Then, for example, the controller 180 may determine that the coordinates of the point at which the user gazes, that is, the ROI, is outside of the side window in the driver seat of the vehicle, select the leftward-direction image obtainment apparatus (not illustrated) that corresponds to the outside point at which the user gazes, and obtains the image information from the leftward-direction image obtainment apparatus.

Accordingly, in some implementations, the controller 180 may recognize at least one object T2 or T3 from the image information that is obtained from the leftward-direction image obtainment apparatus. For example, if the object T2 or T3 is a string of characters, the controller 180 recognizes the string of characters, and extracts an Internet address, a telephone number, a company name, or the like.

As a specific example, the controller 180 extracts a company name "Coffee," and a telephone number "02-000-0000," based on the image information that is obtained from the leftward-direction image obtainment apparatus, and stores in a telephone directory the information that is extracted according to the control command that corresponds to the extracted information.

In some implementations, the controller 180 determines whether the user drives in the distracted state, based on the biological information obtained through the biological information obtainment unit 145 including the EOG, EMG sensors and the like, in addition to the image information. When based on both the image information and the biological information, the controller 180 may determine whether the user drives in the distracted state by applying a weight to each of the image information and the biological information.

The controller 180 may assign any suitable relationship between the weight to the image information and the weight to the biological information, and is not particularly limited to being changed according to an environment. However, in some implementations the weight assigned to the image information may be greater than the weight assigned to the biological information.

In some implementations, the relationship between the weight assigned to the image information and the weight assigned to the biological information may be different based on whether the weight relationship is applied in the drowsy driving state or the stressful driving-state.

Stressful Driving-State

In some implementations, based on at least one among the image information and the biological information, the controller 180 can determine that the user drives in a stressful state, in which case a dangerous driving-state may result.

For example, the controller 180 may determine whether the user drives in the stressful state using the image information, and as a specific example, the controller 180 may use the user's facial expression.

As one example, if it is determined that the user's facial expression corresponds to anger, then the controller 180 may determine that the user drives in a stressful state.

In some implementations, the level of stressful state in which the user drives may be determined according to the user's facial expression, based on a database in which different levels of stress according to the user's different facial expression are stored.

In addition or as an alternative to image information, the controller 180 may determine whether the user drives in a stressful state based on biological information that is obtained through the biological information obtainment unit 145.

As one example, the controller 180 determines the extent of the user's stress based on the heart rate and/or heart rate variability measured through a PPG sensor. In some implementations, the heart rate and/or hear rate variability may pass through a predetermined filter to remove noise. Thus, the precision with which the extent of stress is measured may be improved.

In some implementations, the controller 180 may utilize multiple pieces of biological information, and may apply weights to the multiple pieces of biological information. For example, in some implementations, the weights assigned to the multiple determination bases may be weights that are set through a learning model based on a database of the determination bases. This may, for example, help improve accuracy of determining a stressful state.

In some implementations, the learning model may be based on based on a database of image information and biological information for the user and/or for other persons.

Based on the generated learning model, the controller 180 may determine the dangerous driving-state or the danger level.

In some implementations, the controller 180 may determine a driver's stressful state based on both biological information and image information. This may be useful, for example, to improve accuracy of determining a stressful state. For example, if the controller 180 determines whether the user drives in the stressful state, based only on image information or based only on biological information, then accuracy may be limited (e.g., the number of levels for the evaluation of the stressful state in which the user drives may be limited), and it may be difficult to precisely determine which one of the levels for the evaluation of the stressful state the stressful state in which the user drives correspond to.

Therefore, in some implementations, the controller 180 may determine whether the user drives in the stressful state, based on the biological information in addition to the image information.

When determining a stressful state based on both image information and biological information, the controller 180 may determine whether the user drives in the stressful state by applying weights to each of the image information and the biological information.

There may be any suitable relationship between the weight assigned to the image information and the weight assigned to the biological information, and the relationship may not particularly be limited to being changed according to an environment. However, in some implementations, the weight assigned to the bio-image information may be greater than the weight assigned to the image information.

In some implementations, the relationship between the weight assigned to the image information and the weight assigned to the biological information may depend on whether the controller 180 is determining a drowsy driving-state or determining a distracted driving-state, or determining a stressful driving state.

In some implementations, when the controller 180 determines whether the user drives in a stressful state, or the level of the stressful state in which the user drives, as described above, the image information and the biological information may both be considered, and in some implementations additional consideration may be given to the drowsiness trend line created using at least one among the sleep-state information on and biorhythm information on the user that are available before the user drives the vehicle (refer to FIG. 13).

The sleep trend line (e.g., in FIG. 10) that is calculated by the mobile terminal 100 may be used to take into account the sleepiness state of the user in determining whether the user drives in the stressful state and the level of the stressful state in which the user drives For example, when the controller 180 determines the level of the stressful state in which the user drives, the controller 180 may combine a first stress level calculated based on image information and biological information, and a second stress level that corresponds to the level of drowsiness calculated based on the drowsiness trend line, and thus may calculate a more precise level of the stressful state in which the user drives.

In some implementations, a predetermined weight may be applied to each of the first stress level and the second stress level, and thus the level of the stressful state in which the user drives may be calculated.

For example, the weight that is applied to each of the first stress level and the second stress level may be predetermined by a user input or may be adaptively changed according to the finally-determined level of the stressful state in which the user drives.

Determination of the Dangerous Driving-State

As described above, the controller 180 may detect a dangerous driving-state for a user based on at least one piece of information among image information and biological information.

As examples, a dangerous driving-state may include a drowsy driving-state, a distracted driving-state, and a stressful driving state.

In addition, for the dangerous driving-state for each of the drowsy driving-state, the distracted driving-state, and the stressful driving-state, the controller 180 may generate information on the danger level for each of the drowsy driving-state, the distracted driving-state, and the stressful driving-state, which indicates the extent of the drowsiness, the extent of the distraction, and the extent of the stress, respectively.

In some implementations, if the controller 180 determines a dangerous driving level based on both the image information and the biological information, the controller 180 may apply weights to each of the image information and the biological information. The weights may differ among the drowsy driving-state, the distracted driving-state, and the stressful driving-state.

As described above, in some implementations, in the case of the drowsy driving-state and the distracted driving-state, the information on the danger level may be generated by applying a higher weight to the image information than to the biological information, and in the case of the stressful driving-state, the information on the danger level may be generated by applying a higher weight to the biological information than to the image information.

In some implementations, as described above, the relationship between the weight assigned to the image information and the weight assigned to the biological information may depend on the environment, and may also depend on whether the controller 180 is evaluating the drowsy state, in the distracted state, or in the stressful state.

As a specific example, the controller 180 may determine that noise is included in the image information that is obtained from at least one image obtainment apparatus 900 or that an error is present in at least one portion of the image information.

In such scenarios, if the reliability of the image information that is determined by the controller 180 is not sufficient (e.g., falls short of a threshold level), then the weight that is applied to the image information in evaluating whether the user drives in the dangerous state may be lowered gradually or lowered to a particular value. Alternatively or additionally, the user maybe visually and/or aurally notified that something is wrong with the image information (e.g., through the output unit 150, the different mobile terminal 100, the vehicle and/or the vehicle control apparatus 400).

Likewise, the controller 180 may determine that noise is included in the biological information that is obtained through the biological information obtainment apparatus 145 or that an error is present in at least one portion of the biological information.

In such scenarios, if the reliability of the biological information that is determined by the controller 180 is not sufficient (e.g., falls short of a threshold level), then the weight that is applied to the biological information in evaluating whether the user drives in the dangerous state may be lowered gradually or lowered to a particular value. Alternatively or additionally, the user may be visually and/or aurally notified that something is wrong with the biological information (e.g., through the output unit 150, the different mobile terminal 100, the vehicle and/or the vehicle control apparatus 400).

As one example, if the image obtainment apparatus 900 and/or the biological information obtainment unit 145 is out of order, then the corresponding weight maybe lowered in evaluating whether the user drives in the dangerous state. Alternatively or additionally, information on the apparatus or unit that is out of order, among the image obtainment apparatus 900 and the biological information obtainment unit 145, may be output to the user (e.g., through the output unit 150, the different mobile terminal 100, the vehicle and/or the vehicle control apparatus 400).

In some implementations, when the information on the danger level is generated based on the image information and the biological information, the controller 180 generates the information on the danger levels for at least two driving states, among the drowsy driving-state, the distracted driving-state, and the stressful diving-state.

For example, if the controller 180 determines which one of the drowsy driving-state, the distracted driving-state, and the stressful driving-state, the dangerous state in which the user drives corresponds to, the controller 180 may set an order of priority that corresponds to the information on the danger level of the dangerous driving-state for each of the drowsy driving-state, the distracted driving-state, and the stressful driving-state.

Therefore, in some implementations, if the controller 180 generates the pieces of information on the multiple danger levels, the controller 180 may determine which one of the drowsy driving-state, the distracted driving-state, and the stressful driving-state the dangerous driving-state in which the user drives, according to the order of priority that corresponds to the information on each danger level.

Outputting

The output unit 150 outputs information on the dangerous driving-state that is determined by the controller 180, or the information on the danger level of the dangerous driving-state in various forms (e.g., which stimulate a user's five senses).

According to some implementations, the output unit 150 outputs the information on the danger level in the form of a vibration of the main body of the mobile terminal 100 and of a sound, but changes output strength as the information on the danger level changes.

Figure 12:
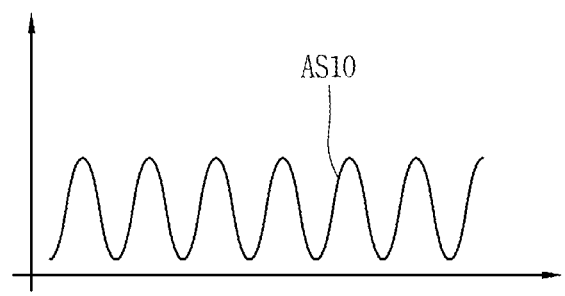
FIG. 12 is a diagram illustrating examples of outputting information regarding a danger level.
Figure 12:
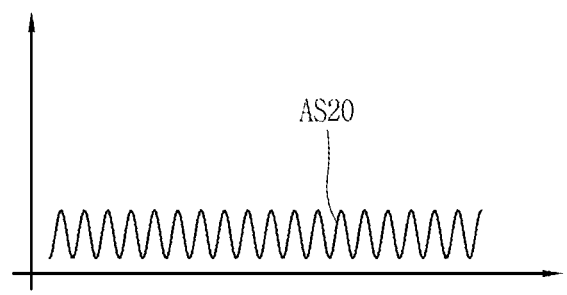
Figure 12:
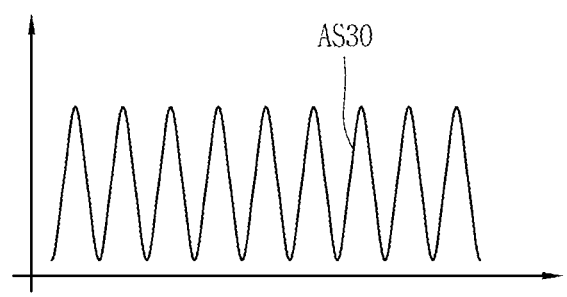
Figure 12:
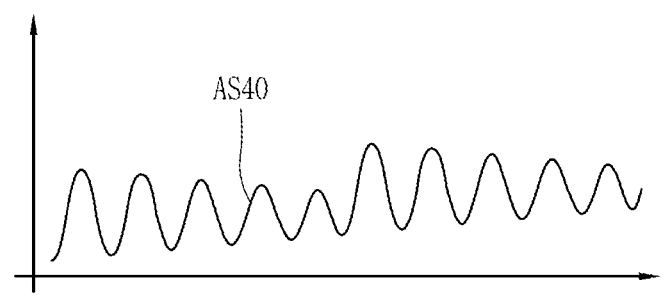

FIG. 12 is a diagram illustrating various methods of outputting the information on the danger level, disclosed in the present specification, according to some implementations.

As one example, as illustrated in FIG. 12, when an alarm AS10 is defined as having a basic amplitude and a basic frequency, the mobile terminal 100 outputs an alarm AS20 of which the vibration frequency increases as the danger level increases, outputs an alarm AS30 of which the vibration amplitude increases as the danger level increases, or output the alarm AS20 or the alarm AS30 of which a vibration output period is shortened.

In addition, when the alarm AS10 is defined as having the basic amplitude and the basic frequency, the mobile terminal 200 may output to the outside an alarm AS40 of which the vibration frequency or the amplitude changes over time according to the information on the danger level.

As described, the alarm of which the vibration frequency and the amplitude vary depending on the information on the danger level may be output. However, according to some implementations, a voice or a sound (for example, "A current drowsy driving-state is at the level 5") of which a frequency, amplitude, and/or an output period varies depending on the information on the danger level may be output.

The mobile terminal 100 outputs the sound that varies depending on the information on the danger level, but the sounds that vary depending on the dangerous driving-state for each of the drowsy driving-state, the distracted driving-state, and the dangerous driving-state are output.

In some implementations, if the drowsy driving-state in which the user drives is determined as the dangerous driving-state, the sound that is output through the output unit 150 may be large in amplitude and high in frequency. However, if the stressful driving-state in which the user drives is determined as the dangerous driving-state, music and the like that calms the user down may be output through the output unit 150.

According to some implementations, the information on the dangerous driving-state and the information on the danger level of the dangerous driving-state are transmitted to the vehicle control apparatus, and thus the vehicle control apparatus 400 outputs the information on the danger level in the form of an image or a voice through the output unit 450 of the vehicle control apparatus 400, or outputs the information on the danger level to the outside through a vehicle output unit (not illustrated) that is installed in the vehicle, using the vehicle drive unit 420.

Like the mobile terminal 100, the output unit 450 of the vehicle control apparatus and the vehicle output unit (not illustrated) also changes an output form or output strength as the dangerous driving-state or the information on the danger level changes, and accordingly outputs to the outside the information on the dangerous driving-state or the information on the danger level.

According to some implementations, if the output unit 450 of the vehicle control apparatus and the vehicle output unit, as described above, output the information on the dangerous driving-state and the information on the danger level in the form of a voice or the sound, the output unit 450 of the vehicle control apparatus and the vehicle output unit change a voice or sound type, a voice or sound frequency, a voice or sound amplitude and/or a voice or sound output period, as the dangerous driving-state or the information on the danger level changes, and accordingly output the information on the dangerous driving-state or the information on the danger level.

In addition, the vehicle output unit is an emergency light, at least one among LEDs that are installed on a dashboard or in the vicinity of the dashboard, or at least one among a vibration seat of the vehicle and a wheel vibration-enabled steering apparatus. The vehicle output unit changes at least one, among an output period of the emergency light, a light color of an LED, an output period of the LED, a vibration frequency of the vibration seat or of the vibration-enabled wheel steering apparatus, vibration amplitude of the vibration seat or of the vibration-enabled wheel steering apparatus, and a vibration period of the vibration seat or of the vibration-enabled wheel steering apparatus, as the information on the dangerous driving-state on the information on the danger level changes, and accordingly outputs the information on the dangerous driving-state on the information on the danger level.

In addition, the vehicle control apparatus 400 directly opens at least one, among windows installed in the vehicle for ventilating the vehicle, or operates an air conditioning unit in order to lower the level of the dangerous driving-state in which the user drives.

In addition, if the level of the dangerous driving-state is higher than a predetermined level, the vehicle control apparatus 400 may directly control the driving of the vehicle.

At this point, after at least one, among the mobile terminal 100, the vehicle control apparatus 400, and the vehicle output unit, takes the measure described above to lower the danger level of the dangerous driving-state in which the user drives, or after a predetermined time elapses, it may be repeatedly determined whether the evaluation of the danger level should be repeatedly performed and thus whether the measure should continue to be taken repeatedly until the danger level falls below a predetermined level.

As a specific example of the measure to lower the danger level, if the controller 180 determines that the dangerous driving-state in which the user drives results from the drowsy driving-state, in a case of the first to third levels of drowsiness, the controller 180 turns on at least one LED into green in color, among the LED in the vicinity of the dashboard of the vehicle, among the vehicle output units.

In addition, in a case of the fourth to fifth levels of drowsiness, the controller 180 turns on the LED into yellow in color, but the output unit 150 outputs in the form of a voice an estimated time (which can be determined from the drowsiness trend line created based on the sleep-state information and/or the biorhythm information) at which the user can drive in a non-drowsy state, which is determined based on the current biological information on the user.

In addition, in a case of the sixth level of drowsiness, the controller 180 turns on the LED into yellow in color, but the outputs 150 outputs in the form of a voice the estimated time at which the user can drive in the non-drowsy state.

In addition, in a case of the seventh level of drowsiness, the controller 180 turns on the LED into red in color. However, the output unit 150 continuously generates the vibration for five seconds at intervals of five seconds using a haptic module 155, gives a warning in the form of a voice using the sound output unit 153, and proposes a method for shaking off drowsiness (for example, "Take a drink of water").

In addition, in a case of the eighth level of drowsiness, the controller 180 turns on the LED into red in color. However, the output unit 150 continuously generates the vibration for three seconds at intervals of three seconds using the haptic module 155, gives the warning in the form of a voice using the sound output unit 153, and the vehicle control apparatus 400 guides the vehicle to a road shoulder or a service area near a current position, as a destination point, or a pass stop.

In addition, in a case of the ninth level of drowsiness, the controller 180 turns on the LED into red in color. However, the controller 180 performs control in such a manner that the vibration is continuously generated for a 0.5 second at intervals of a 0.5 second using the haptic module 155, the vehicle control apparatus 400 enables the emergency light, among the vehicle output units, to flicker, the warning is given in the form of a voice using the sound output unit 153, and the vehicle control apparatus 400 reduces a speed of the vehicle or guides the vehicle to a stop near the current position.

As another example, if the controller 180 determines that the dangerous driving-state in which the user drives results from the stressful driving-state, in a case of the first level of drowsiness, the controller 180 turns on at least one LED into green in color, among the LED in the vicinity of the dashboard of the vehicle, among the vehicle output units.

In addition, in a case of the second level of stress, the controller 180 turns on the LED into yellow in color.

In addition, in a case of the third level of stress, the controller 180 turns on the LED into red in color. However, the output unit 150 outputs in the form of a voice the information on the current stressful driving state in which the user drives, using the sound output unit 153 or outputs in the form of a sound or a voice a breathing method for alleviating the stress.

At this time, the controller 180 determines whether the user breathes according to the breathing method for alleviating the stress, by obtaining the biological information on the user's breathing through the biological information obtainment unit 145. If the use does not breathe according to the breathing method that is output, the controller unit 180 gives a visual warning through the mobile terminal 100, the vehicle control apparatus 400, and/or the vehicle output unit, and thus alerts the user to the fact that the user does not breathe according to the breathing method.

In addition, according to some implementations, the controller 180 transmits to a different mobile terminal the information on the dangerous driving-state in which the user drives and the information on the danger level and thus outputs the information on the danger level in the form of a vibration of a main body or a voice through an output unit of the different mobile terminal. Thus, a person carrying the different mobile terminal helps the drive to get out of the dangerous driving-state.

As one example, when the person carrying the different mobile terminal is near the driver, he/she awakens the driver, recommends the drive to gaze forward, and help the drive to feel less stressful.

If the person carrying the different mobile terminal is far away from the driver, he/she can make a call to the driver or communicate with the driver in order to awaken the driver, recommend the driver to gaze forward, and help the driver to feel less stressful.

Vehicle Control Apparatus that Determines Whether a Driver is in a Dangerous Driving State Some examples of a vehicle control apparatus that determines whether the driver drives in a dangerous state are described in detail below.

In some implementations, the vehicle control apparatus is configured to include a communication unit 431, an image information obtainment unit 470, and a controller 410.

The communication unit 431 is configured to correspond to the short-range communication module 431 described referring to FIG. 6A. The description of the short-range communication module 431 substitutes for a decryption of the communication unit 431 and the detail decryption of the communication unit 431 is omitted.

In addition, the image information obtainment unit 470 obtains the image information on the user from the image obtainment apparatus 900.

The controller 410 controls the communication unit 431 in order to receive the biological information on the user or obtain the image information through the image information obtainment unit 470. Thus, the controller 410 detects the dangerous driving-state in which the user drives, based on at least one among the image information and the biological information.

In some examples, a dangerous driving-state in which the user drives includes at least one among a drowsy driving-state, a distracted driving-state, and a stressful driving-state.

The controller 410 determines which one of the drowsy driving-state, the distracted driving-state, and the stressful driving-state, a state in which the user drives corresponds to, or the information on the danger level for each of the drowsy driving-state, the distracted driving-state, and the stressful driving-state.

The controller 410 applies the weight to the multiple determination bases when making a determination based on the image information and/or the biological information in order to produce the information on the dangerous driving-state in which the user drives, or the information on the danger level.

In some implementations, in order to improve the precision of the determination of the dangerous driving-state or the information on the danger level, in some implementations the weight to the multiple determination bases may be a weight that is set through the learning based on a database.

For example, the learning model is based on based on the database of the image information and the biological information on the user and/or based on other persons. Based on the generated learning model, the controller 180 determines the dangerous driving-state or the danger level.

In addition, when the controller 410 produces the information on the dangerous driving-state in which the user drives and the information on the danger level, the image information and the biological information is used, but the weight is applied to each of the image information and the biological information in order to improve the precision of the determination by the controller 410 of the dangerous driving-state and the information on the danger level.

In some implementations, the weight to be applied differs among the drowsy driving-state, the distracted driving-state, and the stressful driving-state.

In some implementations, when the controller 410 determines whether the user drives in the drowsy state (including the stressful state), or the level of the drowsy state (including the level of the stressful state) in which the user drives, as described above, the image information and the biological information may both be considered, and in some implementations, additional consideration may be given to the drowsiness trend line created using at least one among sleep-state information on and biorhythm information on the user that are available before the user drives in the vehicle (e.g., in FIG. 13).

That is, in some implementations, when the controller 410 determines the level of the drowsy state (including the level of the stressful state) in which the user drives, the controller 180 combines a first drowsiness driving level (including the first stress level) calculated based on the image information and the biological information, and a second drowsiness driving level (including the second stress level) that corresponds to the level of the drowsiness calculated based on the drowsiness trend line, and thus calculates the precise level of the drowsy state (including the precise level of the stressful state) in which the user drives.

Predetermined weights may be applied to each of the first drowsiness driving level (including the first stress level) and the second drowsiness driving level (including the second stress level) to determine the level of the drowsy state (including the level of the stressful state) in which the user drives.

In some implementations, the weight that is applied to each of the first drowsiness driving level (including the first stress level) and the second drowsiness driving level (including the second stress level) may be predetermined by the user input or may be adaptively changed according to the finally-determined level of the drowsy state (including the finally-determined level of the stressful state) in which the user drives.

In some implementations, the output unit 450 outputs information on the dangerous driving-state that is determined by the controller 410, or information on the danger level of the dangerous driving-state in various forms (e.g., which stimulate the user's five senses).

The output unit 450 may output the information on the danger level in the form of an image or a voice. The output unit 450 may change the output forms and the output strength as the information on the danger level changes, and accordingly outputs the information on the danger level.

If the output unit 450 of the vehicle control apparatus, as described above, outputs the information on the dangerous driving-state or the information on the danger level in the form of an image, a voice, or a sound, the output unit 450 of the vehicle control apparatus may change an image or change a voice or sound type, a voice or sound frequency, a voice or sound amplitude voice and/or a voice or sound output period as the dangerous driving-state or the information on the danger level changes, and accordingly outputs the information on the dangerous driving-state or the information on the danger level.

In addition, the controller 410 may output the information on the danger level through the vehicle output unit (not illustrated) installed in the vehicle. The vehicle output unit (not illustrated) may change the output form or the output strength as the dangerous driving-state or the information on the danger level changes, and accordingly outputs to the outside the information on the dangerous driving-state or the information on the danger level.

In some implementations, the vehicle output unit is an emergency light, at least one among LEDs that are installed on a dashboard or in the vicinity of the dashboard, or at least one among a vibration seat of the vehicle and a wheel vibration-enabled steering apparatus. The vehicle output unit changes at least one, among an output period of the emergency light, a light color of an LED, an output period of the LED, a vibration frequency of the vibration seat or of the vibration-enabled wheel steering apparatus, vibration amplitude of the vibration seat or of the vibration-enabled wheel steering apparatus, and a vibration period of the vibration seat or of the vibration-enabled wheel steering apparatus, as the information on the dangerous driving-state or the information on the danger level changes, and accordingly outputs the information on the dangerous driving-state or the information on the danger level.

In addition, in some implementations, the vehicle control apparatus 400 directly opens at least one, among windows installed in the vehicle for ventilating the vehicle, or operates an air conditioning unit in order to lower the level of the dangerous driving-state in which the user drives.

In addition, in some implementations, if the level of the dangerous driving-state is higher than a threshold level, the vehicle control apparatus 400 may directly control the driving of the vehicle.

After at least one, among the mobile terminal 100, the vehicle control apparatus 400, and the vehicle output unit, performs an output operation described above to lower the danger level of the dangerous driving-state in which the user drives, or after a predetermined time has elapsed, the system may determine whether the evaluation of the danger level should be repeatedly performed and thus whether the further output operations should continue to be taken to lower the danger level.

According to some implementations, the dangerous driving-state and the information on the danger level of the dangerous driving-state that are determined by the controller 410 are transmitted to the mobile terminal 100, and thus the mobile terminal 100 outputs the dangerous driving-state and the information on the danger level in the form of a vibration of a main body and a sound, but changes the output strength as the information on the danger level.

As one example, as illustrated in FIG. 12, when the alarm AS10 is defined as having the basic amplitude and the basic frequency, the mobile terminal 100 outputs the alarm AS20 of which the vibration frequency increases as the danger level increases, outputs the alarm AS30 of which the vibration amplitude increases as the danger level increases, or output the alarm AS20 or the alarm AS30 of which the vibration output period is shortened.

In addition, when the alarm AS10 is defined as having the basic amplitude and the basic frequency, the mobile terminal 200 may output to the outside an alarm AS40 of which the vibration frequency or the amplitude changes over time according to the information on the danger level.

As described, the alarm of which the vibration frequency and the amplitude may vary depending on the information on the danger level may be output. However, according to some implementations, a voice or a sound (for example, "A current drowsy driving-state is at the level 5") of which a frequency, an amplitude, and/or an output period varies depending on the information on the danger level may be output.

The mobile terminal 100 may output a sound that varies depending on the information on the danger level, and also that varies depending on the dangerous driving-state for each of the drowsy driving-state, the distracted driving-state, and the dangerous driving-state.

In addition, according to some implementations, the controller 410 transmits to a different mobile terminal the information on the dangerous driving-state in which the user drives or the information on the danger level and thus outputs the information on the danger level in the form of a vibration of a main body or a voice through an output unit of the different mobile terminal. This may, for example, notify a person carrying the different mobile terminal to help the driver to get out of the dangerous driving-state.

As one example, when the person carrying the different mobile terminal is near the driver, he/she may awaken the driver, recommend the driver to gaze forward, or help the driver to feel less stressful, based on the received alert.

In some implementations, if the person carrying the different mobile terminal is far away from the driver, he/she can make a call to the driver or communicate with the driver in order to awaken the driver, recommend the driver to gaze forward, or help the driver to feel less stressful.

Vehicle to which Some Implementations can be Applied

An example of a vehicle to which the technology disclosed in the present specification can be applied is described below referring to FIG. 14.

Figure 14:
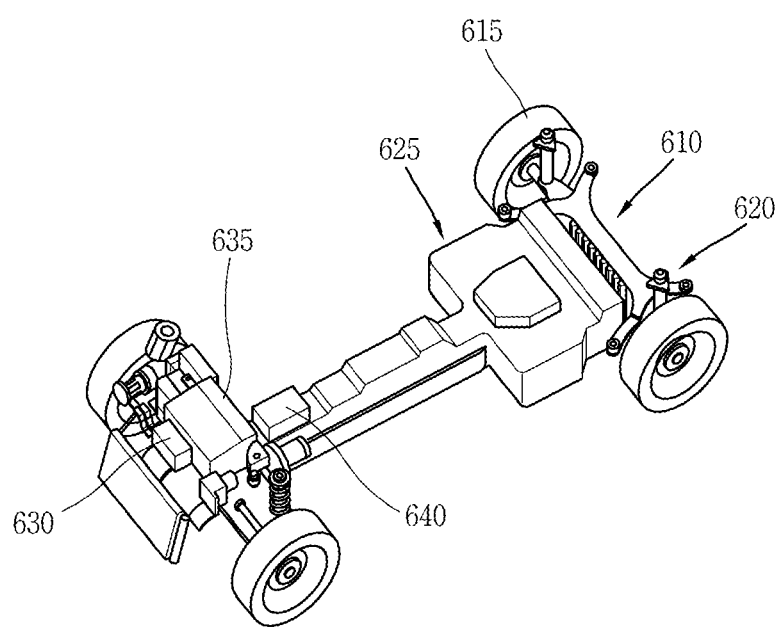
FIG. 14 is a schematic diagram of an example of an electric vehicle that is equipped with a battery charging apparatus.

FIG. 14 illustrates an example of an electric vehicle. Other types of vehicles may be used (for example, vehicles equipped with a gasoline engine, a diesel engine, or an LPG engine) as implementations are not limited to a particular type of vehicle.

FIG. 14 is a schematic configuration diagram of the electric vehicle that is equipped with a battery charging apparatus, according to some implementations.

As illustrated in FIG. 14, an electric vehicle 600 equipped with the battery charging apparatus according to some implementations is configured to include a vehicle body 610, a battery 625 provided in the vehicle body 610, and a battery charging apparatus 640 provided in the vehicle body, which is connected to an external power source to charge the battery 625.

Although not illustrated in the drawings, a riding space where the driver or the passenger is seated is provided in an upper portion of the vehicle body. For example, a cabin where the riding space is formed is provided in the vehicle body 610.

The vehicle body 610 is configured to include multiple wheels 615 that rotate to enable the vehicle to drive. A suspension system 620 is provided between the vehicle body 610 and wheel axles of the wheels 615. The suspension system 629 allows the vehicle to drive over rough surfaces with a minimum of up-and-down movement of the vehicle body 610, absorbing vibration and impact due to bumps and holes in the road.

The wheel 615 is provided to right-front, right-rear, left-front, left-rear sides of the vehicle body 610.

The battery 625 that supplies electric power is provided in the vehicle body 610.

The battery 625 is configured from rechargeable secondary batteries.

A motor 630 that provides driving force to the wheel 615 is provided to one side of the vehicle body 610.

An inverter 635 that provides electric power to the motor 630 is provided in the vehicle body 610. The inverter 635 is connected to each of the battery 625 and the motor 630.

The inverter 635 is connected to the battery 125, and direct current power is supplied to the inverter. The inverter converts the direct power into power suitable for driving the motor 630 and supplies the resulting power to motor 630.

The battery charging apparatus 640 is provided in the vehicle body 610 in order to charge the battery 625. The battery charging apparatus 640 is configured to include a charging circuit 660 that is connected to an external commercial power source (AC), converts commercial power into power suitable for charging the battery 625, and provides the resulting power to the battery 625. At this point, although not specifically illustrated, the charging circuit 660 is configured to include a commercial power input unit that is connected to the commercial power source and into which the commercial power is input, a rectifying unit and a smoothing unit that converts into direct current the commercial power that is input through the commercial power input unit, and an power conversion unit that converts the direct current power, resulting from the conversion, into the power suitable for charging the battery 625 and output the resulting power.

A number of methods, techniques, systems, and apparatuses have been described. Nevertheless, various modifications may be made without departing from the scope of this disclosure.

The methods, techniques, systems, and apparatuses described herein may be implemented in digital electronic circuitry or computer hardware, for example, by executing instructions stored in tangible computer-readable storage media.

Apparatuses implementing these techniques may include appropriate input and output devices, a computer processor, and/or tangible computer-readable storage media storing instructions for execution by a processor.

A process implementing techniques disclosed herein may be performed by a processor executing instructions stored on a tangible computer-readable storage medium for performing desired functions by operating on input data and generating appropriate output. Suitable processors include, by way of example, both general and special purpose microprocessors. Suitable computer-readable storage devices for storing executable instructions include all forms of non-volatile memory, including, by way of example, semiconductor memory devices, such as Erasable Programmable Read-Only Memory (EPROM), Electrically Erasable Programmable Read-Only Memory (EEPROM), and flash memory devices; magnetic disks such as fixed, floppy, and removable disks; other magnetic media including tape; and optical media such as Compact Discs (CDs) or Digital Video Disks (DVDs). Any of the foregoing may be supplemented by, or incorporated in, specially designed application-specific integrated circuits (ASICs).

Although the operations of the disclosed techniques may be described herein as being performed in a certain order and/or in certain combinations, in some implementations, individual operations may be rearranged in a different order, combined with other operations described herein, and/or eliminated, and desired results still may be achieved. Similarly, components in the disclosed systems may be combined in a different manner and/or replaced or supplemented by other components and desired results still may be achieved.

The foregoing implementations and advantages are merely examples and are not to be considered as limiting the present disclosure. The present teachings can be readily applied to other types of apparatuses. This description is intended to be illustrative, and not to limit the scope of the claims. Many alternatives, modifications, and variations will be apparent. The features, structures, methods, and other characteristics of the implementations described herein may be combined in various ways to obtain additional and/or alternative implementations.

What is claimed is:

1. A driver state monitoring (DSM) system comprising:
an image obtainment apparatus configured to obtain image information of a user driving a vehicle;
a biological information obtainment unit configured to be worn on a specific portion of the user's body and to obtain biological information from the specific portion of the user's body; and
a controller configured to detect a dangerous driving-state in which the user drives the vehicle based on a weighted combination of the image information and the biological information of the user.

2. The system of claim 1, wherein the controller is configured to, based on the image information and the biological information, determine whether the dangerous driving-state corresponds to a drowsy driving state, a distracted driving-state, or a stressful driving-state.

3. The system of claim 2, wherein the controller is configured to, based on the image information and the biological information, generate information on a danger level indicating an extent of danger corresponding to the determined dangerous driving-state.

4. The system of claim 3, wherein the controller is configured to generate the information on the determined danger level by applying a weighting factor to at least one of the image information or the biological information.

5. The system of claim 4, wherein the applied weighting factor differs depending on whether the dangerous driving-state corresponds to the drowsy driving state, the distracted driving-state, or the stressful driving-state.

6. The system of claim 3, wherein the controller is configured to output the generated information on the determined danger level through an output unit.

7. The system of claim 6, wherein the controller is configured to adjust an output strength of the information on the danger level as the information on the danger level changes, and wherein the information on the danger level is output according to the adjusted output strength.

8. The system of claim 7, wherein the output unit is provided in a mobile terminal and is configured to output the information on the danger level in the form of a vibration output or an audio output.

9. The system of claim 8, wherein the controller is configured to adjust the output strength by changing at least one of a frequency of the vibration output, an amplitude of the vibration output, an output period of the vibration output, an amplitude of the audio output, contents of the audio output, or an output period of the audio output.

10. The system of claim 6, wherein the output unit is provided in the vehicle, and a vehicle control apparatus provided in the vehicle is configured to control the output unit to output the information on the danger level in the form of an image output or an audio output, and
wherein the output unit is at least one of an emergency light, a light emitting diode (LED) installed in a dashboard of the vehicle, a vibration-enabled seat of the vehicle, or a vibration-enabled wheel steering apparatus of the vehicle.

11. The system of claim 10, wherein the controller is configured to adjust the output strength by changing at least one of an output period of the emergency light, a light color of the LED, an output period of the LED, a vibration frequency of the vibration-enabled seat or of the vibration-enabled wheel steering apparatus, an amplitude of the vibration, or an output period of the vibration.

12. The system of claim 2, wherein the biological information includes at least one of sleep-state information or biorhythm information of the user that is measured before the user drives the vehicle.

13. The system of claim 12, wherein the dangerous driving-state corresponds to a drowsy driving-state, and
wherein the controller is configured to generate a drowsiness trend line over time for the user, based on at least one of the sleep-state information or the biorhythm information, and to detect the dangerous driving-state, based on the generated drowsiness trend line and the image information.

14. The system of claim 2, wherein the controller is configured to generate a driving-state learning model for determining the user's dangerous driving-state based on past image information and past biological information of the user, and to detect the dangerous driving-state based on the image information, the biological information, and the generated driving-state learning model.

15. The system of claim 1, further comprising a mobile terminal configured to be worn on the specific portion of the user's body, wherein the mobile terminal comprises:
the biological information obtainment unit, and
a communication unit that receives the image information from an image obtainment apparatus provided in the vehicle.

16. The system of claim 15, wherein the mobile terminal further comprises the controller.

* * * * *